United States Patent [19]
Prendergast et al.

[11] Patent Number: 6,048,702
[45] Date of Patent: *Apr. 11, 2000

[54] MURINE AND HUMAN BOX-DEPENDENT MYC-INTERACTING PROTEIN (BIN1) AND USES THEREFOR

[75] Inventors: George C. Prendergast, Doylestown; Daitoku Sakamuro, Philadelphia, both of Pa.

[73] Assignee: The Wistar Institute of Anatomy and Biology, Philadelphia, Pa.

[*] Notice: This patent issued on a continued prosecution application filed under 37 CFR 1.53(d), and is subject to the twenty year patent term provisions of 35 U.S.C. 154(a)(2).

[21] Appl. No.: 08/870,126

[22] Filed: Jun. 6, 1997

Related U.S. Application Data

[63] Continuation-in-part of application No. 08/652,972, May 24, 1996, Pat. No. 5,723,581, which is a continuation-in-part of application No. 08/435,454, May 5, 1995, Pat. No. 5,605,830.

[51] Int. Cl.$^7$ .......................... C07K 16/00; C07K 16/42; G01N 33/53

[52] U.S. Cl. .......................... 435/7.1; 530/300; 530/350; 530/387.1; 530/387.2; 530/387.3; 530/387.7; 530/387.9; 530/388.1; 530/388.15; 530/389.1; 536/23.1; 436/501

[58] Field of Search .......................... 536/23.1; 530/300, 530/350, 387.1, 387.2, 387.3, 387.7, 387.9, 388.1, 388.15, 389.1; 435/7.1; 436/501

[56] References Cited

U.S. PATENT DOCUMENTS

| | | | |
|---|---|---|---|
| 4,419,446 | 12/1983 | Howley et al. | 435/68 |
| 5,605,830 | 2/1997 | Prendergast et al. | 435/325 |

FOREIGN PATENT DOCUMENTS

| | | |
|---|---|---|
| WO91/18088 | 11/1991 | WIPO. |
| WO96/31625 | 10/1996 | WIPO. |
| WO 96/34627 | 11/1996 | WIPO. |

OTHER PUBLICATIONS

R. Wechsler–Reya et al., "The Putative Tumor Suppressor BIN1 is Short–Lived Nuclear Phosphoprotein, The Localization of Which is Altered in Malignant Cells", *Cancer Research*, 57:3258–3268 (Aug. 1, 1997).
D. Sakamuro, "BIN1 is a Novel MYC–Interacting Protein with Features of a Tumour Suppressor", *Nature Genetics*, 14:69–77 (Sep. 1996).
D. Sakamuro et al., "The Polyproline Region of P53 is Required to Activate Apoptosis but Not Growth Arrest", *Oncogene*, 15:887–898 (Aug. 21, 1997).
M. Cole, "The myc Oncogene: Its Role in Transformation and Differentiation", *Ann. Rev. Genet.*, 20:361–384 (Dec. 1986).
D. Askew et al., "Constitutive c–myc Expression in an Il–3–dependent Myeloid Cell Line Suppresses Cell Cycle Arrest and Accelerates Apoptosis", *Oncogene*, 6:1915–1922 (Oct., 1991).
G. Evan et al., "Induction of Apoptosis in Fibroblasts by c–myc Protein", *Cell*, 69:119–128 (Apr. 3, 1992).
T. Strohmeyer et al., "Review Article—Proto–Oncogenes and Tumor Suppressor Genes in Human Urological Malignancies", *J. Urol.*, 151:1479–1497 (Jun., 1994).
G. Mark et al., "Humanization of Monoclonal Antibodies", Chapter 4, *The Handbook of Experimental Pharmacology*, vol. 113, The Pharmacology of Monoclonal Antibodies, Springer–Verlag (Jun., 1994).
S. Fields et al., "A Novel Genetic System to Detect Protein–Protein Interactions", *Nature*, 340:245–246 (Jul. 20, 1989).
D. Negorev et al., "The Bin1 Gene Localizes to Human Chromosome 2q14 by PCR Analysis of Somatic Cell Hybrids and Fluorescence in Situ Hybridization", *Genomics*, 33:329–331 (Apr., 1996).
Databases EMBL/genebank/DDBJ on MPSRCH, Accession No. Z24792, Auffray et al., (Jul. 30, 1993).
Database Genexpress on MPSRCH, Accession No. Z28487, Auffray et al., (Dec., 1993).
Databases EMBL/Genebank/DDBj on MPSRCH, Accession No. F00405, Auffray et al. (Mar. 7, 1995).
Database IMAGE Consortium, LLNL on MPSRCH, Accession No. R34418, Hillier et al. (May 2, 1995).
Databases EMBL/Genebank/DDBJ on MPSRCH, Accession No. Z24784, Auffray et al. (Jul. 30, 1993) [Auffray IV].
The Washington–Merck EST Project on MPSRCH, Accession No. R18250, Hillier et al., (Apr. 14, 1995) [Hillier II].
U.S. Patent application No. 08/652,972, filed May 24, 1996.
D. Sheiness et al., "Identification of Nucleotide Sequences which May Encode the Oncogenic Capacity of Avian Retrovirus MC29", *J. Virol..*, 28(2):600–610 (Nov., 1978).
M–J. Gething et al., "Cell–surface Expression of Influenza Haemagglutinin from a Cloned DNA Copy of the RNA Gene", *Nature*, 293:620–625 (Oct. 22, 1981).
R. Kaufman et al., "Coamplification and Coexpression of Human Tissue–Type Plasminogen Activator and Murine Dihydrofolate Reductase Sequences in Chinese Hamster Ovary Cells", *Mol. Cell. Biol.*, 5(7):1750–1759 (Jul., 1985).

(List continued on next page.)

*Primary Examiner*—David Guzo
*Assistant Examiner*—Sean McGarry
*Attorney, Agent, or Firm*—Howson and Howson

[57] ABSTRACT

The present invention provides antibodies raised against a Box-dependent myc-interacting polypeptide termed Bin1 or fragments thereof are provided. Also provided are compositions and methods utilizing these antibodies in the diagnosis and treatment of cancers and hyperplastic disease states. Further provided are oligonucleotides derived from sequences encoding Bin1, as well as compositions and methods utilizing same for diagnostic and therapeutic purposes.

24 Claims, 21 Drawing Sheets

OTHER PUBLICATIONS

M. Kay et al., "In Vivo Hepatic Gene Therapy:Complete Albeit Transient Correction of Factor IX Deficiency in Hemophilia B Dogs", *Proc. Natl. Acad. Sci. USA*, 91:2353–2357 (Mar., 1994).

S. Ishibashi et al., "Hypercholesterolemia in Low Density Lipoprotein Receptor Knockout Mice and Its Reversal by Adenovirus–mediated Gene Delivery", *J.Clin. Invest.*, 92:883–893 (Aug., 1993).

W. Huse et al., "Reserach Article—Generation of a Large Combinatorial Library of the Immunoglobuline Repertoire in Phage Lambda", *Science*, 246:1275–1281 (Dec. 8, 1989).

A. Vojtek et al., "Mammalian Ras Interacts Directly with the Serine/Threon Kinase Raf", *Cell*, 74:205–214 (Jul. 16, 1993).

G. Prendergast et al., "A New Bind of MYC", *Trends in Genet.*, 8(3):91–97 (Mar., 1992).

A. Rustgi et al., "Amino–terminal Domains of c–myc and N–myc Proteins Mediate Binding to the Retinoblastoma Gene Product", *Nature*, 352:541–544 (Aug., 1991).

G. Prendergast et al., "Biphasic Effect of Max on Myc Cotransformation Activity and Dependence on Amino– and Carboxy–terminal Max Functions", *Genes Dev.*, 6:2429–2439 (Dec., 1992).

A. Kelekar et al., "Immortalization by c–myc, H–ras, and E1a Oncogenes Induces Differential Cellular Gene Expression and Growth Factor Responses", *Mol. Cell. Biol.*, 7(11):3899–3907 (Nov., 1987).

C. Shih et al., "Isolation of a Transforming Sequence from a Human Bladder Carcinoma Cell Line", *Cell*, 29:161–169 (May, 1982).

E. Douglas et al., "A Specific Chromosomal Abnormality in Rhabdomaysarcoma", *Cytogenet. Cell Genet.*, 45:148–155 (May 12, 1987).

G. Prendergast et al., "Postranscriptional Regulation of Cellular Gene Expression by the c–myc Oncogene", *Mol. Cell Biol.*, 9(1):124–134 (Jan., 1989).

F. Bauer et al., "Alteration of a Yeast SH3 Protein Leads to Conditional Viability with Defects in Cytoskeletal and Budding Patterns", *Mol. Cell. Biol.*, 13(8):5070–5084 (Aug., 1993).

B. Lichte et al., "Amphiphysin, a Novel Protein Associated with Synaptic Vesicles", *EMBO J.*, 11(7):25221–2530 (1992).

C. David et al., Autoimmunity in Still–man Syndrome with Breast Cancer is Targeted to the C–Terminal Region of Human Amphiphysin, a Protein Similar to the Yeast Proteins, Rvs167 and Tvs161 *FEBS Letters*, 351:73–79 (Jul., 1994).

D. Miller et al., "An Insect Baculovirus Host–Vector System for High–Level Expression of Foreign Genes", *Genetic Engineering*, 8:277–298 (1986).

FIGURE 1

Partial Mouse BIN1 cDNA and Polypeptide
SEQ ID NOS. 1 and 2

| | | | | | | | | | | | | | | |
|---|---|---|---|---|---|---|---|---|---|---|---|---|---|---|
| GAG | ATC | AGA | GTG | AAC | CAT | GAG | CCA | GAG | CCG | GCC | AGT | GGG | GCC | TCA |
| Glu | Ile | Arg | Val | Asn | His | Glu | Pro | Glu | Pro | Ala | Ser | Gly | Ala | Ser |
| 1 | | | | 5 | | | | | 10 | | | | | 15 |

45

| | | | | | | | | | | | | | | |
|---|---|---|---|---|---|---|---|---|---|---|---|---|---|---|
| CCC | GGG | GCT | GCC | ATC | CCC | AAG | TCC | CCA | TCT | CAG | CCA | GCA | GAG | GCC |
| Pro | Gly | Ala | Ala | Ile | Pro | Lys | Ser | Pro | Ser | Gln | Pro | Ala | Glu | Ala |
| | | | | 20 | | | | | 25 | | | | | 30 |

90

| | | | | | | | | | | | | | | |
|---|---|---|---|---|---|---|---|---|---|---|---|---|---|---|
| TCC | GAG | GTG | GTG | GGT | GGA | GCC | CAG | GAG | CCA | GGG | GAG | ACA | GCA | GCC |
| Ser | Glu | Val | Val | Gly | Gly | Ala | Gln | Glu | Pro | Gly | Glu | Thr | Ala | Ala |
| | | | | 35 | | | | | 40 | | | | | 45 |

135

| | | | | | | | | | | | | | | |
|---|---|---|---|---|---|---|---|---|---|---|---|---|---|---|
| AGT | GAA | GCA | ACC | TCC | AGC | TCT | CTT | CCG | GCT | GTG | GTG | GTG | GAG | ACC |
| Ser | Glu | Ala | Thr | Ser | Ser | Ser | Leu | Pro | Ala | Val | Val | Val | Glu | Thr |
| | | | | 50 | | | | | 55 | | | | | 60 |

180

| | | | | | | | | | | | | | | |
|---|---|---|---|---|---|---|---|---|---|---|---|---|---|---|
| TTC | TCC | GCA | ACT | GTG | AAT | GGG | GCG | GTG | GAG | GGC | AGC | GCT | GGG | ACT |
| Phe | Ser | Ala | Thr | Val | Asn | Gly | Ala | Val | Glu | Gly | Ser | Ala | Gly | Thr |
| | | | | 65 | | | | | 70 | | | | | 75 |

225

| | | | | | | | | | | | | | | |
|---|---|---|---|---|---|---|---|---|---|---|---|---|---|---|
| GGA | CGC | TTG | GAC | CTG | CCC | CCG | GGA | TTC | ATG | TTC | AAG | GTT | CAA | GCC |
| Gly | Arg | Leu | Asp | Leu | Pro | Pro | Gly | Phe | Met | Phe | Lys | Val | Gln | Ala |
| | | | | 80 | | | | | 85 | | | | | 90 |

270

| | | | | | | | | | | | | | | |
|---|---|---|---|---|---|---|---|---|---|---|---|---|---|---|
| CAG | CAT | GAT | TAC | ACG | GCC | ACT | GAC | ACT | GAT | GAG | CTG | CAA | CTC | AAA |
| Gln | His | Asp | Tyr | Thr | Ala | Thr | Asp | Thr | Asp | Glu | Leu | Gln | Leu | Lys |
| | | | | 95 | | | | | 100 | | | | | 105 |

315

| | | | | | | | | | | | | | | |
|---|---|---|---|---|---|---|---|---|---|---|---|---|---|---|
| GCT | GGC | GAT | GTG | GTG | TTG | GTG | ATT | CCT | TTC | CAG | AAC | CCA | GAG | GAG |
| Ala | Gly | Asp | Val | Val | Leu | Val | Ile | Pro | Phe | Gln | Asn | Pro | Glu | Glu |
| | | | | 110 | | | | | 115 | | | | | 120 |

360

| | | | | | | | | | | | | | |
|---|---|---|---|---|---|---|---|---|---|---|---|---|---|
| CAG | GAT | GAA | GGC | TGG | CTC | ATG | GGT | GTG | AAG | GAG | AGC | GAC | TGA |
| Gln | Asp | Glu | Gly | Trp | Leu | Met | Gly | Val | Lys | Glu | Ser | Asp | |
| | | | | 125 | | | | | 130 | | | | |

Human BIN1 cDNA and Polypeptide
SEQ ID NOS. 3 and 4

```
GAATTCCGTG CTGGTTGAGC TTGCTCATCT CCTTGTGGAA GTTTTCCTCC            50

AGGCCCGCG ATG CTC TGG AAC GTG GTG ACG GCG GGA AAG ATC GCC        95
           Met Leu Trp Asn Val Val Thr Ala Gly Lys Ile Ala
            1               5                      10

AGC AAC GTG CAG AAG AAG CTC ACC CGC GCG CAG GAG AAG GTT CTC      140
Ser Asn Val Gln Lys Lys Leu Thr Arg Ala Gln Glu Lys Val Leu
         15                  20                  25

CAG AAG CTG GGG AAG GCA GAT GAG ACC AAG GAT GAG CAG TTT GAG      185
Gln Lys Leu Gly Lys Ala Asp Glu Thr Lys Asp Glu Gln Phe Glu
         30                  35                  40

CAG TGC GTC CAG AAT TTC AAC AAG CAG CTG ACG GAG GGC ACC CGG      230
Gln Cys Val Gln Asn Phe Asn Lys Gln Leu Thr Glu Gly Thr Arg
         45                  50                  55

CTG CAG AAG GAT CTC CGG ACC TAC CTG GCC TCC GTC AAA GCC ATG      275
Leu Gln Lys Asp Leu Arg Thr Tyr Leu Ala Ser Val Lys Ala Met
         60                  65                  70

CAC GAG GCT TCC AAG AAG CTG AAT GAG TGT CTG CAG GAG GTG TAT      320
His Glu Ala Ser Lys Lys Leu Asn Glu Cys Leu Gln Glu Val Tyr
         75                  80                  85

GAG CCC GAT TGG CCC GGC AGG GAT GAG GCA AAC AAG ATC GCA GAG      365
Glu Pro Asp Trp Pro Gly Arg Asp Glu Ala Asn Lys Ile Ala Glu
         90                  95                 100

AAC AAC GAC CTG CTG TGG ATG GAT TAC CAC CAG AAG CTG GTG GAC      410
Asn Asn Asp Leu Leu Trp Met Asp Tyr His Gln Lys Leu Val Asp
        105                 110                 115

CAG GCG CTG CTG ACC ATG GAC ACG TAC CTG GGC CAG TTC CCC GAC      455
Gln Ala Leu Leu Thr Met Asp Thr Tyr Leu Gly Gln Phe Pro Asp
        120                 125                 130

ATC AAG TCA CGC ATT GCC AAG CGG GGG CGC AAG CTG GTG GAC TAC      500
Ile Lys Ser Arg Ile Ala Lys Arg Gly Arg Lys Leu Val Asp Tyr
        135                 140                 145

GAC AGT GCC CGG CAC CAC TAC GAG TCC CTT CAA ACT GCC AAA AAG      545
Asp Ser Ala Arg His His Tyr Glu Ser Leu Gln Thr Ala Lys Lys
        150                 155                 160
```

FIGURE 2B

| | | | | | | | | | | | | | |
|---|---|---|---|---|---|---|---|---|---|---|---|---|---|
| AAG | GAT | GAA | GCC | AAA | ATT | GCC | AAG | GCC | GAG | GAG | GAG | CTC | ATC | AAA | 590 |
| Lys | Asp | Glu | Ala | Lys | Ile | Ala | Lys | Ala | Glu | Glu | Glu | Leu | Ile | Lys |
| | | 165 | | | | | 170 | | | | | 175 | | |

```
AAG GAT GAA GCC AAA ATT GCC AAG GCC GAG GAG GAG CTC ATC AAA    590
Lys Asp Glu Ala Lys Ile Ala Lys Ala Glu Glu Glu Leu Ile Lys
        165                 170                 175

GCC CAG AAG GTG TTT GAG GAG ATG AAT GTG GAT CTG CAG GAG GAG    635
Ala Gln Lys Val Phe Glu Glu Met Asn Val Asp Leu Gln Glu Glu
        180                 185                 190

CTG CCG TCC CTG TGG AAC AGC CGC GTA GGT TTC TAC GTC AAC ACG    680
Leu Pro Ser Leu Trp Asn Ser Arg Val Gly Phe Tyr Val Asn Thr
        195                 200                 205

TTC CAG AGC ATC GCG GGC CTG GAG GAA AAC TTC CAC AAG GAG ATG    725
Phe Gln Ser Ile Ala Gly Leu Glu Glu Asn Phe His Lys Glu Met
        210                 215                 220

AGC AAG CTC AAC CAG AAC CTC AAT GAT GTG CTG GTC GGC CTG GAG    770
Ser Lys Leu Asn Gln Asn Leu Asn Asp Val Leu Val Gly Leu Glu
        225                 230                 235

AAG CAA CAC GGG AGC AAC ACC TTC ACG GTC AAG GCC CAG CCC AGA    815
Lys Gln His Gly Ser Asn Thr Phe Thr Val Lys Ala Gln Pro Arg
        240                 245                 250

AAG AAA AGT AAA CTG TTT TCG CGG CTG CGC AGA AAG AAG AAC AGT    860
Lys Lys Ser Lys Leu Phe Ser Arg Leu Arg Arg Lys Lys Asn Ser
        255                 260                 265

GAC AAC GCG CCT GCA AAA GGG AAC AAG AGC CCT TCG CCT CCA GAT    905
Asp Asn Ala Pro Ala Lys Gly Asn Lys Ser Pro Ser Pro Pro Asp
        270                 275                 280

GGC TCC CCT GCC GCC ACC CCC GAG ATC AGA GTC AAC CAC GAG CCA    950
Gly Ser Pro Ala Ala Thr Pro Glu Ile Arg Val Asn His Glu Pro
        285                 290                 295

GAG CCG GCC GGC GGG GCC ACG CCC GGG GCC ACC CTC CCC AAG TCC    995
Glu Pro Ala Gly Gly Ala Thr Pro Gly Ala Thr Leu Pro Lys Ser
        300                 305                 310

CCA TCT CAG CCA GCA GAG GCC TCG GAG GTG GCG GGT GGG ACC CAA   1040
Pro Ser Gln Pro Ala Glu Ala Ser Glu Val Ala Gly Gly Thr Gln
        315                 320                 325

CCT GCG GCT GGA GCC CAG GAG CCA GGG GAG ACG GCG GCA AGT GAA   1085
Pro Ala Ala Gly Ala Gln Glu Pro Gly Glu Thr Ala Ala Ser Glu
        330                 335                 340

GCA GCC TCC AGC TCT CTT CCT GCT GTC GTG GTG GAG ACC TTC CCA   1130
Ala Ala Ser Ser Ser Leu Pro Ala Val Val Val Glu Thr Phe Pro
        345                 350                 355
```

FIGURE 2C

```
GCA ACT GTG AAT GGC ACC GTG GAG GGC GGC AGT GGG GCC GGG CGC    1175
Ala Thr Val Asn Gly Thr Val Glu Gly Gly Ser Gly Ala Gly Arg
        360                 365                 370

TTG GAC CTG CCC CCA GGT TTC ATG TTC AAG GTA CAG GCC CAG CAC    1220
Leu Asp Leu Pro Pro Gly Phe Met Phe Lys Val Gln Ala Gln His
        375                 380                 385

GAC TAC ACG GCC ACT GAC ACA GAC GAG CTG CAG CTC AAG GCT GGT    1265
Asp Tyr Thr Ala Thr Asp Thr Asp Glu Leu Gln Leu Lys Ala Gly
        390                 395                 400

GAT GTG GTG CTG GTG ATC CCC TTC CAG AAC CCT GAA GAG CAG GAT    1310
Asp Val Val Leu Val Ile Pro Phe Gln Asn Pro Glu Glu Gln Asp
        405                 410                 415

GAA GGC TGG CTC ATG GGC GTG AAG GAG AGC GAC TGG AAC CAG CAC    1355
Glu Gly Trp Leu Met Gly Val Lys Glu Ser Asp Trp Asn Gln His
        420                 425                 430

AAG AAG CTG GAG AAG TGC CGT GGC GTC TTC CCC GAG AAC TTC ACT    1400
Lys Lys Leu Glu Lys Cys Arg Gly Val Phe Pro Glu Asn Phe Thr
        435                 440                 445

GAG AGG GTC CCA TGACGGCGGG GCCCAGGCAG CCTCCGGGCG TGTGAAGAAC    1452
Glu Arg Val Pro
        450

ACCTCCTCCC GAAAAATGTG TGGTTCTTTT TTTTGTTTTG TTTTCGTTTT        1502

TCATCTTTTG AAGAGCAAAG GGAAATCAAG AGGAGACCCC CAGGCAGAGG        1552

GGCGTTCTCC CAAAGTTTAG GTCGTTTTCC AAAGAGCCGC GTCCCGGCAA        1602

GTCCGGCGGA ATTCACCAGT GTTCCTGAAG CTGCTGTGTC CTCTAGTTGA        1652

GTTTCTGGCG CCCCTGCCTG TGCCCGCATG TGTGCCTGGC CGCAGGGCGG        1702

GGCTGGGGGC TGCCGAGCCA CCATACTTAA CTGAAGCTTC GGCCGCACCA        1752

CCCGGGGAAG GGTCCTCTTT TCCTGGCAGC TGCTGTGGGT GGGGCCCAGA        1802

CACCAGCCTA GCCTGCTCTG CCCCGCAGAC GGTCTGTGTG CTGTTTGAAA        1852

ATAAATCTTA GTGTTCAAAA CAAAATGAAA CAAAAAAAAA AATGATAAAA        1902

ACTCTCAAAA AAACAAGGAA TTC                                    1925
```

FIGURE 3A

[5' flanking region and exon 1; p31.2] ...

gcacatggga cgtcgacctg aggtaattat aacccgggcc ctatatatgg atccaaccaa
ctgtggactg aaaatatttg gaaaaataca ataaaaagta agactacaac aataaaataa
tataaataaa aaacaaggcc gggcacggtg gctcacacct ataatcccag cactttggga
ggccaaggcg ggaggatcac gaggtcagga gatggagacc atcttggcca acatggtgaa
actccgtctc tactaaaaat acaaaaatta gctgggcatg gtggcacgtg cctgtagtcc
cagctgctcg gggggctgag gcaggagaat cacttgaacc cgggaggcag gaagttgcag
tgagcccaga ttgtgccact gcacccccaga ctggcgacag agtgagactc tgtctaaaaa
taaataaata aataaataaa aaatacagcg ttaacaacta tttacatagt atttaaattg
tattagctat tacaagaatc tagagataat ttaaagtatt ttggaagatt tgttttacgc
tatatgccga tactgttttc cattcctatt gaaggacttg agcatcccct ggatttggg
tatcccccga tgtnctggaa ccatcccccc gggggaaacc caagggaact ncttgaatan
taggcccgga aaagnacaaa caaccccnt gggccntggg gcaccnctaa ccggtgntga
aaaancccca attacccgaa aaaaaccag nagggcctcc cagggaaaaa ggnannggcc
tgtgtgaacc caggtgaact tttcattcnt gggantcgat ttctccattt gtacaaactg
cttggtttgt ggtctgcaag agcccttcct gttcctccag gaagcttctc agggacntct
gtccctggcc agctctgctc ctctgaccgc tgcgggtcct gcaggccata gccctggctc
ctgtgtgtgc accagacacg tctaggctct tcagcgggac ctatctctct gctcaactca
atcaacagtt ctttagaaat ttccaggggc agcaaagtgc tgtagcccct gacatgtttt
agggctgaat gggggtgggt atcagcagac tcaatacgta tttattaact taaagaagt
gtcattggtc tattggcaaa gctggttagc aataaccta tcttctccag gaataatgat
cactaatcat tccttcctgc tgggggtagg agacaacccg gcgtatggtg gtggagcacc
tgggagacag aggcagagat ctcgttcctc gatcccggcg cgttggttgt aaagtaggaa
cagtaatagc acctacctct agggccacgg agaccgaatg aaataatgcc tgtcaagtca
cttagtacac agtaagcact cagtaatgct aggttgttgt tattataata aatttttagc
gaacggggaa gaccaagcac cggttggtac tgggttaggc gccgtagggc aaagatgtgg
agatgtcccg gaggcgccta gggtatccgg gcgaaaaccc gagggccgaa ggctgggagg
aggcggagcg tcgggcaccg gcaccgggc gggaggtgag cccctggaaa aggaggggac
tccggcgcg ttctcccagc agccgcggct cctctgttca gggccgcgcc cccttcgccg
cactttttct ttgatttcga aagcactcct ctcctccacc tagtctcctt tcctgggttg
caggagagtt actgctttgc ggggaaagaa caagacgcca ggccggcgga ttagtccccg

FIGURE 3B

```
ccccggggcg gtgcagctgg agcgtcaggg gagtcccgct cgccgcagcc ccagcgccgc gcgcgcccat ccatcctaga aggacctggc ggtgccggcg cccggagtgg ccctttaaaa ggcagcttat tgtccggagg gggcgggcgg ggggcgccga ccgcggcctg aggcccggcc cctccctct ccctccctct gtccccgcgt cgctcgctgg ctagctcgct ggctcgctcg (exon1/+1)
cccgtccggc GCACGCTCCG CCTCCGTCAG TTGGCTCCGC TGTCGGGTTG CGCGGCGTGG

AGCGGCAGCC GGTCTGGACG CGCGGCCGGG GCTGGGGGCT GGGAGCGCGG CGCGCAAGAT

CTCTCCCCGC GCGAGAGCGG CCCTTGCCAC CGGGCGAGGC CTGCGCCGCG ATGGCAGAGA
                                                       (*START)

TGGGCAGTAA AGGGGTGACG GCGGGAAAGA TCGCCAGCAA CGTGCAGAAG AAGCTCACCC

GCGCGCAGGA GAAGgtgagc gagccggagc cccagcagcc gcggagtccc agccgccgcg gagccccggc cacctgtccc cctatcctcc gaccccgggg cctggtcctt cgccaggatc tggtgctgtc acctctagag gagcgctttc gagggcttc gaggtcccca ggctgcgttc cccggcgctc tgggtgccct cttaggtttg cgtcctctgt ctccccacac ccggccgggg caggacaggg ccccgctttg caccttcgtg gctcggctgc acagcagtgg ccggccctgc tccagggctc ttctcaggcg cgcgctccaa gctacccct ttggaagcca agggccngga agcttgggaa gccagttggt gacctcnact ctcccagccc catgcangca acctangctn ggccngcctc cgggcganca nggaatntct tccttnttcc ccctgnggga ttttttncc ccttncantc nccttggntn cctctctatt ctngtttctt tcttccn ...

<<< > 10 kb GAP >>>

[5' end of 21.1:]
...

acatagttcc ccaggaacan aacccttctt ccaagcccat ntntcaaaan gngagntgtc cntgcaacca gacacacagg acccttctcc cgggtgntgt naacacctcc ccatccccac tcggacagtg gagccaccta agcctgctcc ccacctctgg gtggagagtc tcggtggcct ccaacaatnt aggngccang caggaggcca cagcagccct gacgagagag cagagggagg aaaagaggtt ttaagcccac cactcacctc cacatttcat gtggccctct cacctcctta ttttcaaagt ataaacctca aagaaagtgg aaaggatact acagggacta tcatttaccc ttcacccaga ttcaccaatc aactgttacc acttggccac antcatttgc ttttttcttt tttttttttt tctttttttt tgctnttctc ttttcttgct atgtcgtcca agctagaata catggcgcaa tcatggctca cagtagccta gactttctga gnttaaacga tccgcccacc tcagcgtccc gagtagctgg gantacaggc cactgcacct agttagtatt tttacttttt
```

FIGURE 3C gtagagacag ggcctcgcta tgttgcccag gtttgtctgg aactcctagc ctcaagtgat cgagtcgact ctagaggatc cccggtaccg agctcgaatc gcct ...

<<< 6kb GAP >>>

[exon 2; p21.1]

....

accatgggct gggtgatgtt ggatagagac ttcccagccc atggtctgtg ntgttggtga ctgagcactg attggtttga ccactntcct ttccaaggta acactctccc cttctctntn (exon2)
ggnttcggca gGTTCTCCAG CAGCTGGGGA AGGCAGATGA GACCAAGGAT GAGCAGTTTG AGCAGTGCGT CCAGAATTTC AACAAGCAGn tngtgagtgt gggtggccct tggccttagg gagtttgtga aaattcggct gccaggtgaa aaatggcacg agctgaattt gtggagtacg agagcttgga ggagggtaat cagtgtgggc tgacaagatc atgtaagact tcctngagga gggagcactg gcaatgcatt gaagggangg aagagggatg gggtatgtat gctttaggtt cttggtagga gacatagaaa cggtagttgg gggagggggga gggggagggt gggataggag caggcaatag attgtggcca gacttgggga aactttgcat gtcagggca agtggagcta ttaganttg t ....

<<< 4-5 kb GAP >>>

[exons 3-6; p33.1]

...

atttcctgtt caggagttna caaccagccc cantttccct tcagccttt ccttacatcc tatgtccctg ctgtcagctg ggccagtgat cttggccatg accaccgcat tctgcaccct gctgtagtgc gtttcttccg cagttcttct gtccctatac aggctcgcac cgggccntct tttcntagta cgaggcagtg ggagctctct gtccttgggc accacctgag cttgtggagc aggggcctg gtggtcacca cacctgcctt gcccatactc ctgtgctcat tggtcacttg tctgcaggtg tctgagggca ggtctgtgag tgccggggct gctgcacact ggtgctgtgc tgtttgtgtg tcattcagcc gtacctccag cacgtcatct cggagggggg tctttgtctt cctgccttcc ttcctgggct gagaatggca tctggaagat ggcaggtgcc cacaagcatg ggcaagggtg cctatggacg cagggcttct gaggcagggg tggtgaccgt agctgctgtc ctgttgggag gtcagctgat cagtggctgc tgtcaggaga gcagcctggt tcattcacgt gagggtggca ggaaggagag ggtcagggac tgggtgtgcc accagtccct gacctggtcc (exon3)
ttgtccttct ctttgcCTGA CGGAGGGCAC CCGGCTGCAG AAGGATCTCC GGACCTACCT GGCCTCCGTC AAAGgtaggg aggcaggcag aagcgcacct ggcccgtgta gagctggtgg

FIGURE 3D gtgcagagct ggggagggtg ggacaagcgc tatcagtggg aggcccacat acttcctttc (exon4)
tgccccacag CCATGCACGA GGCTTCCAAG AAGCTGAATG AGTGTCTGCA GGAGGTGTAT GAGCCCGATT GGCCCGGCAG GGATGAGGCA ACAAGATCG CAGAGgtgag catgggacag gtgggcctgc ccttctcaga gggccctctg gtctcagctc ctgtcccact ctgccgtgcc ctctgggaca agcctctctg gttctgggc attcgcgtgc tgtgtgccct ggggcaagct gccctccctc tctgagggcc tttctcctga cacgccctca caccaaggtg ggtcagatgg tgggtcgtgg tcgtccttat ttgtgtgtta tggctcacaa ctcacaaagc ctccctggct gacccccagtc ctcagcgtat ctgatcctca cagtcacccc aatagggcag gaacatttgc ccccatctta cagatgggga aactgaggct ctgagaagcc actgagctgt gaagagatgg ggctggggct ggtccctgcg aagtgagcgc tggggcgggt gtggcccagc cctcctggtg (exon5)
gcactgtcgt gctcttgcct gtctcagAAC AACGACCTGC TGTGGATGGA TTACCACCAG

AAGCTGGTGG ACCAGGCGCT GCTGACCATG GACACGTACC TGGGCCAGTT CCCCGACATC

AAGgtgagag acccacttgc agatctgccc tgctctggcc tggagggaac tggagagagg acagggccta ggaccttgcg gctcaggcca agaagaagct gtccttggag gcaggaagcg cctggcccgg tgtttcaccc ctccggggtt gctccctctg ccaccagccc acggccccc attcctttcc tgtcccttg ggtctcaggg ctatgggagg aagcctcacg gcacgtgtgt gtgtgtgtgt gtgtgtgtgt gtgtgtgttg cngcggagtg gctggctata tgattgtgga aggtgtataa gagggagtag ggccaaaaac atgtgtgtgc ctgcaggtcc cctgtgttta caccatgggt gcttgaagg gtatgtgtgc atgtcacctg ttgtctgggt ctacatgtgt gggtgtgtgc gtgtggttgt gtgcattcgc aaagcctgtt gtttctgcca ggcctgggtt ggtgctcgga gctggcagtg tctctggtat ccaccgaggc gagtggtccc cggtaacgtg cacatggaag cctgggttga ccattgggtt ggacgagatc ccccttggtg ggcaggatgg gggtgtcatg ctccatgcta gcctcagggg tccccagttg cagatgcctc aagctccctg agtctgatgt tggtggctgt ggagatgaga agccagggc caggccaagg aaaagacttg gctgacacgt caccagctgg tggacacgga catgggct catgtgcaag gaagtggttt cacacagtgg ggctggacgg ccaggagggg gtgagctctc tgccacgagg agggttccag caacaagggc tcaagggttc ctgtggagct ggggtctcct gcccgccctg cgggtccctc caggatccac tggacctgga gtctcagcag gggtgccagg cccgcttag tgccctcctc (exon6)
tgtctgcccc agTCACGCAT TGCCAAGCGG GGGCGCAAGC TGGTGGATAC GACAGTGCCC

FIGURE 3E

GGCACCACTA CGAGTCCCTT CAAACTGCCA AAAAGAAGGA TGAAGCCAAA ATTGCCAAGg taagggctgg aggcgggtcg gggcagcgtc tgcagggggc tgagagaggg cgggtgtcta ggaccccgag ggtggaggct tcctcctgcc tggccccagg tggctgaact gggggtgggg acnatacagg gcccaggccg gtgagtgaga ggcccttgtg ggtgcctggg tgaggtccac cctaggccca ttcctgcccc ccgtgccacc ctggcccctc agccctgatc caggccacct gccagcctga gaatgggcct cctgggtttc cctggaacgg cgccgccctg cctggcgagc cgggtggaat tcgtcacgcg atcccaggcg acctgtccct ggctggagcg agccagtagg tgcagagctg gccccactca tcctttggtg aggggctggg gtggccccgt cctccgggca gggccgtgct tgctgggccc cctgtgctgc taaccacgct caccttttgc ctctgcagtt ggagttcacc cccttccctt acccccgggg ctcccctaa ttctctcggc ctcaagggcc catatctgct tggggtggcc ccccgcncgt ggggcgttgt ggacctgcat ttaatctgtg tgtctctgtt tctctctccc cactccctgg tctctcccac cttcct ....

<<< 3-4 kb GAP >>>

[exons 7-12 plus one putative brain-specific alternate exon sequence; p3.3]
...

ccagntgcnt ggntgcntct ccctggccct gcaccttctt ntagggtccc cctgacattc ctagaggtgc ctgagtgnct gcntctggtc tccctctggt gggacaggtc ccaggagagg gctttgtggg aaggaccatc cctgggaggt gaagtgaagg ctggtggctg aggctgccag gagctggccc tcagaaatgg ggagggagca ctcaggggcg ggggcaattg ggggcagcga cagatgctgc cctgagagcc agaaggcagt ggcagggctg gcacctagcc tgaggaggtt cattgtggaa gtgggcaggg tccccacttg gctgggtctg gggtntgcct ctgtgcatgt cccgtgtcca gctcgccaag ccccaggctt gcccctcttg ttgtgcccta ctccacgctc actgccctcc cggccacgtg ggcctctctt tggcaacggc tgctcagccc tccctttccc agatgtcctc agggtcctgg agggctgcag ggggaggtcg ccagcatggg tgtccacatc cagttcagcc tctgtcttgc ccggagccct ggtcccagcg cactggccaa gagggtggg caggaggtgg gaggactggc catgggctg ggctggctgg gacgcccaac agaggggaat (exon7)
gacccgtgct gccccccagG CCGAGGAGGA GCTCATCAAA GCCCAGAAGG TGTTTGAGGA GATGAATGTG GATCTGCAGG ATGAGCTGCC GTCCCTGTGG AACAGgtgag gcccggcacg gtgcccagcc tgcgtggggc agtgtccagt ctgcgtgctg cagtgcccag tctgcgtgct gtggtgccca gcctgcgtgc tgcggtgtcc agtctgcgtg ctgcggtgcc cagcctgtgt

FIGURE 3F gctgcagtgt ccagcctgag tgctgcggtg cctgggccct ctctggtttg tgcctctgat gagcgtgtgt ggtcgctcgt gggtgggtat ttctgagttg ctgtcctgac ctgcctgttc (exon8)
acctggcccc catccttccg cccttctgta gCCGCGTAGG TTTCTACGTC AACACGTTCC AGAGCATCGC GGGCCTGGAG GAAAACTTCC ACAAGGAGAT GAGCAAGgta ggccatgggg acccctctga ggggccacac cccaccctgg ccgagggtca gagtcagaat cgtgggaggg gcagcctgaa ctcctccttc cctgccaggt tcagcacaca ccggtgacca cagggctccc tcccggccct ggtggaacag ccccccttcag gagtgcctgg gccccaggaa gggcaccagg gcatgctggg gaggctttga gagtgtcctg ggtccttgcc tgggtagacc acctgagaat gtagaccagg ccctctcaaa ctgtgaatgt gttctctagc aaccttggcc cagggagtgc agtgttagac aatggtggca gtttctcaat ttgtaggaaa aaattactag cattttctca attttaattt ttctcccatg cttttgagac atttaaatag gcctgtttcg tctgcgtgaa tccactgtgc gacagggtct ggtctgatta gcgtaccttt ctctcttgtg ttattttcat tttaacctat ctggcaacta aaacgcaaag ctgttgaact ttgcagttgg agagacccag ggctggcacc cccgccccca gtggtgggtc tgactttgtc tcttgggccc agatggatga agtgatgatg gtggattcca ggcccagggt cggaggagga aaagcagctt ggggcctccc ctgactcaca cttctaagta cggtttcctg ccttttagac tttctctttc cttcttaact tttccttttt cccttcgaag attggagaca acttacgaaa agtttaaaaa atagagaaag gtgtttcaga gaaggaacat ttatataaaa ttagtctgta aaatatatg ccacagaaca tagttgttta taaataggat gaagattcgg cctgagctcc tatgggccaa tccaaaaaaa gaatattcnc cntnatgaaa atccccntgt nttangaata aacccccccc cctgcctgtg ctttcnntga aatatctggn anttgttgtg tggtcngaaa acntcntggg naaatgaccn ttacaattna nantnatggn cngcccaaac naatttttaan aaaaaaatnt ttaaacagtg ccagctcnnt gttggatttt agganatccc cntnagtttng aggggggaaan atnggttccc aaaanagcag gggtttttna tnttcccccc ttcccccttt tgtgttgccc cctggttttt ccgggtttgg tgttctaatt ccctgccctc tcacagatgg ggaaagagga gcttgttcct ggcagggct gggggtggtg gggagaagca gaggtgtttg gggaaggtgg ggccgtttgg (exon9)
tggccttgga ggccccccac ctcctcactg tctctcctgc agCTCAACCA GAACCTCAAT

GATGTGCTGG TCGGCCTGGA GAAGCAACAC GGGAGCAACA CCTTCACGGT CAAGGCCCAG

CCCAGgtgcg tgcggggaga gccctggcgc ccctgactgt gtgcacggca ggggcagggc tccttcctgt gaccctgttg gtgccctccc ctggtccccc atgggtttgg ccttgggggt

FIGURE 3G

```
ctagggacct tcctgtcttg gcctctctgt gctcagggag gcaggtgagg gcaggtctct
gtctcgaatg tccctgcccc tctggctgtg ttcgtcgagg aaggagcact ctggggagtc
cgcgggtacc ctgagccggc tgacccctc attgtggagc acgagcatcc agggttgggg
tgggcagcct gctcagcttt ggggactggg gggtgtgaac aggactgaaa gactccgggg
tgtgcagtcc tctcagagca gggagatagc accgcccttc ctctcctgct ngtggnaaaa
gatcatgtcc ctggatggca gcattgtgct caaccacang agcatcctct tcctgtcctc
agcctcagcc cctccgggaa tcccagctgc aaggaggcct ctgtttcctg aggggaaacc
atgagggagg agggaaatgc cttgctttcc tggctgtgga tcagaggaag cagcgagcct
gggacttccc ctcccttntg gccatgtgtg catgtgtgtg tgtgaggggg actgtgtgtg
acaggtgtaa gtgtgtgcat acccacacac atatcacagc agaacgcaga gaacaccgat
ggactctgta aaacagggcg actgtctgct tcttggggta ttgcctggga tgatgagggt
atcgggtggt ggtgattgcc ccctccttcc ctgaacataa aatagttgtg gctgagagag
gggccatggt gacctgaggc tgggagtggg gaggttagga cggtggcgtt gtggtggtgg
ttgggggggt gggtaggggg gtggggggttg ggataaagcc aaaaggtgaa ttcaaggtcg
ggcagggagg gacagctgcc tggcctgtag gcacaggtgg gaacantggg atggatcagc
aggggggtaag tggggccgtc ctggccagaa ccatggctcc cctcaggaag gaggtggagg
gaagagagag gggcagtaga ggcccaggag tctcccttcc agcagagagg cctcttgtgc
actntgtgct cgcctggggg ccttttctgg cactntgggc acacctggag ctcctgggga
ctgggaccac aggcagggtg actatccact gccccgagcc tcctgcccct caccaggccc
tgttagcatc acctcgggca cctggccaca gcaggggcca gtcagggcac cccgggatag
cacgcccagg ccctgtgcaa ggcctctggc acttaggaga ggcttttgcc cctttgtcct
ctgagcagaa gggttggcaa agagggaagg ggacaggcca gttctgcacc tggcctttct
                                                       (exon10)
ccagaatgaa ggcctccacc tcccgtccgt ccccacagAA AGAAAAGTAA ACTGTTTTCG
CGGCTGCGCA GAAAGAAGAA CAGgtaccgg cagtgagtgc tgcgggaggg gcgcagaggc
ccgcgccctg gctggccctg tgcatgcgcc ttcgcccctg ctcccaggtg ccactaaccc
gtaatctggc tctgtgtgca gtgctgcccg gcagggctgt cgtgtgcgtg ttgggtggga
aggcggaggc ggcgcggggc gggctggcct ctgagcatct ggctgcattt agcacgttcc
tctgggcgcc ccacacttgt ctagccctgg tggtgcccgg gccaccagcg cacttagcaa
tggaggacgt ggctgggaag gaggcctggg gagggccagg gaggtgacac tgcagcactg
tggggttttt tgttttttaa acaattctat gtgtataccc tatacttata catatattct
```

FIGURE 3H ttaaggagaa tacattccca taaaacacaa ntccagaagg aaagatggtg tcagcgacat ctcttacgnt gttccactgt ttgccctcag gtgantcggt cactggttcc tgctggatgn ttgtagatgt gcactgtcca gcacaggagc cagttacccc atggggctat tgagcacttg aaactggcca gtgtgaccgg gcagcggaac ttttcatttg aattacacat aaatttcatt gctttgagtt tgcattgccg cctgtggcta gtggcaaccg tactgggcag cacttttcta ggcgtctctg tgcaggttct ggtagagaat tttctccctg caccttcgcc cctgtgcctg gggtgcacag catcacacca cctccgcctt gggttctggc actgaacgcc atggctcagg acctgtcccc tccatcgcca gctgcccact cctctgtgat gaggacgcct ctcttagttt gtccaggccc tgcttgtggc ctccagcagc cgagaggaca ggagagccca aggtctagag acatgtacca gggtgctgtg atggacaggc agggagggca gcaggctggg gagcagaccc cagaacagag gggctgctgc gtgtggtgtg ggagactcac tgtgcctcta ggatgtctgg ctttctcctg ctgtggatct tgggctgtca gcatgggccc tggtggaccc catggagcct gtggggtggt tggtctggtc tctgcgacag atggttccaa gggacctgcc tgcactcctg gggaccatag acctccagcc tggagtccca ccttgtgctg ttcctgtttc tgaggcaggc ttcccacttc cagcccccca agcccaggtc ccttggctcc cccaccctc ctgctctctc tcacatacac acacacacac acacacagtt tcacacctcc atatgcacac acctcttcac acagacgtca atacatttgc ccctccgtct cctgtgcctt ggcccccaa cactgggctc (exon11)
cctttcttgt cctcccccac agTGACAACG CGCCTGCAAA AGGGAACAAG AACCCTTCCG

CCTCCAGATG GCTCCCCTGC CGCCACCCCC GAGATCAGAG TCAACCACGA CCAGAGCCGG

[putative.alt.
CCGGCGGGGC CACGCCCGGG GCCACCCTCC CCAAGTCCCC ATCTCAG[GTA GGGAGNGAAG exon]
TTTTGGTAGA AGGTCCCAAG CCNTCCATCN ATNTCGTCNG GGATNGGCTG TTGTCCTCCA

TCCTCCCACT CCCTGTCCCC TTTCTGGCCT GGGCAGCTAT GGACCCGATG CTTTGCCCAG

TGGGGGTTGG GCCTGGACCT GGGTGTCCTT TCCCCCATCC AGCTGGCATG CTTCCGGGAG

GCATCTGTGA CTTGCTCGTT CCTCCCCAGC CCCCACCCCC ACTGCAGCG]c cctcccttc cctctccntg gtgttttgtg atgntngant ctttntccat nttnttttcc tccctagcag agggtatggg ccctcagccc acagagcatc cagatntcca gagtgggctg cctgtccctn ttnntggcct ctctctttta aaggggcctg agggaggagc ccaagccagg tggccatgca ggacctttaa agggacagag agaggaaggg gtcagaggag ggtgtggggt ggctaagggg gcaggtcntg ggnttgtgga ntgtccttgt gtccaccccg cctgccccca gcgggccctc

FIGURE 3I caggtgtang caggncccta ggtgctggct ggccaggngg gggagttttc atagccggga
tcctgcagct cccgtttttct gctgccgccc tgctctgctg ctgactagga tagcagggct
aaggacatgg tgggagcctg tcccaaacag cacttccccc ggcctggaca tggtgccagt
gccttctgtg tattcgttca ctgagtcccc acaacacccc tgtgaagcag gcgctgtcat
cacctgatgc atgaggaagc ccancgtcat gggtgtgtga cctgcctgag gtcccccacc
tggtgggcag gggtgtggcc tctgcccat cctggtgcca cgctggcttc ctctgggata
cactcgtctg agctgggctc cctgtgggca gccctgtgcc ctgggaggtg gaaagagggg
cctgcgggaa nggagaggtg ggcaggggga ggctggggcc cggctgtctc tcaacgactg
tttgcttccc cagtcttctc accaggccag tgggagccag ccctcccac agttggccag
tgggcagcct ggggcctctc tcttcttcgc tctccttcct cctctcccct cacttctcta
tctcttctct ctccacacag cgtttctgga ccgcctgcct cagtgtccct ctcggggtg
gcctggggtc tnggtgtcta tgttgggggg ctgggaaggc antnactctt catttgctgc
gtcctgctca ntggcctggg tgggatgtgg ctgaggtgtg actaaccgtg gctttgtctc
tgtctgtctc ccccaaaccc cgtgctctgc tgtgccttcc cgcgcggccc ctcaccgcc
          (exon12)
gccgacccac agcTCCGGAA AGGCCCACCA GTCCCTCCGC CTCCCAAACA CACCCCGTCC
AAGGAAGTCA AGCAGGAGCA GATCCTCAGC CTGTTTGAGG ACACGTTTGT CCCTGAGATC
AGCGTGACCA CCCCCTCCCA Ggtcagccgc ggccgccgcg gccagctct cctctcttcc
tgccctctca gggcgtgcat ggccttcatc ctctatgctt ctgtctcaag agccaggaat
ctggccagag agagtgtcag tttccctctc tcacccttg ttccctccat ccatcatcct
ccatcatcct ccatcaccca tctctgagca tgtactaagg ccagatgcag ggccgcagag
gggaaggtgc cgcctctccc ggcgcagcag ttacatcagc agcgccctcg cgatgcagtg
ggtgctatgg cagaggggat cggggagtgt ggaggactgt ggctgtcagg gaaggcttcc
agggccaggg agagttggaa ggtcctggaa tggctgaagc acctggactt cagctcccac
agctgctgtc agccctcga gggcggggc agcggccagg ctgcagggca naactgccgg
tgtgcaacac tccctaagag gcgtggaatg cccagataca gcagggagcc acccagggggg
gcttgggtct ctcccgacgg gcccttggct cagcaaggag ccacgcagag ggtcttgggt
ctctcccagt gggctcttgg ctcagccgtg gaggtgcctc tggggagccc ggcccacagc
cccaggtctt acgtccttca tggtggaggt cgggctggag tacctgtgct ggaagcgcat
cttgccagtg ctggagtggg ctgacgtgtt gtcagatttg cccagaggtg gccggccttc
cccgcactcc ccgagagctg actgcctcct caaggtccag ccctcaaggc ctcaccttcc

FIGURE 3J tcctgtgggt tagccaagaa ccttcccaca caaacctccc ctgttaggaa agctgtccat
ccaagcttgt ggtggcctcc caacaaacac cttccacaca ctcaaaaacc ctantgggga
ntagtttgga aggttttaat tttngggaat ttgcccnctg ggaacttgca aacantggtc
ccctgctaag aaaggtttgg gantggtggg cctccaaccc cctntgcnaa aanntaggaa
attaaaactn aggaaccnaa ggcnnccgcc ....

<<<   2-3 kb GAP   >>>

[exons 13-16 plus three putative brain-specific alternate exons; p3.4]
....

cttgcntttg tccatgaaan nnnnngccca cgggcttacc cggntgtggg gtggtgngta
gcgtgtgtcc ntgacatgga gggacngtcc cgggcctgca tggcggggtg ccacctgccg
gggcagcaca gcgaagggat ggtcagcttt ttggcggatg accctcccct cagcacatga
cggatattgc tgcgtgggtt ggctgacttt tatgagacag gagggagggg tgttgctggg
gcagggtggg ggccactggg gagagatgct ggccgcccgc tggtgggagg cacctcgagg
ctgtgcaccg gcgtcctcag ggctccttca gagacggccg gttatggggc agagcagtga
cctcccgacc ctgggttccc cagacagggc tggacctaaa ggaaagtcag ctgctgggat
tggcccaggg cagggcttgg ggcctagggc ccctggttct aggaagtgag tccacttggc
ctgagctgtc tgacaccttg gcttggccat gtggantgct ccacgcttgt ccctgagtg
caggacagct ggtcttctta ggactgagga ccttggtntc tcccaatggg ccttcggttc
agntatggag tgcttntggg gagcccggcc cacagcccca ggtctcacat ccttcatggt
ggaggccggg tgggagggcg cccctgtcag tgtccggtgc ctgtcaagag tgtgtagagc
cgggaagccg ctggcctggg ctgcggggct ggagttcttc cagcactgcc tgagggcccc
ggaggggagc accccggcca cgtccctctc cttttaaacc tgggcaaagt tctctctggc
ccccaaaggg aagccccagg tacaagatgg agaccgcagc cgagccagtc cctgctcctc
agaaggcagc ttgtgccctg ggcatggatg ctgccccagg gctcaccgga gtcattgtcc
ccgcctgtgc cgggggctct aaggaagccc cttcctccca tgctagtctg gcccagctta
tggggaggct tgtccctgtg tggccagggc caccgtgtcc catccctggg gccatgcctg
tcacatgcct attcctgggc tcactggaag gagatcttgg cgaggggctg ctgggagggg
tcagggcct gcagttttaa cccaagtgcc ccgggtggtt ctgaagcccc cgaatgttga
agacccccact ttgaagcttg gctgttgggc tttgtggctg gctccactct ttctccgtcc
ctggagctga cggctggtgg tgtcgccaga gagtgacctg cctgtctggg gtggaggaaa
agccagtgtg aagtctctgc ctttggaact ttcccagtcg ggagcactga gggtggctgt

FIGURE 3K ggcatggtgt tactctcgcc actgggggt agcaagatca gcagaactct tggcgcaggg agcggagagg aggttcgggc attggtaggg aggggcccac cagtctgtgg atggtggcgg aagagagctg gggcctggtg ctggccctgc ggggtggcgg ccacgggcgg acctatgact gggagtttga ggcgggcact ggggtcgtcc tcctggtgtg ggcgggagcc tgtgccgggg cgcgtggctt tgggcagtgc tcccgtgtgt gaggtggatg agttggtgcc tgggctgtgt gccagcgtgt gtgcgtgtat gtgcgcttgc tctgtgcatg cgtggtgtgt gtatgtgtgt gtgtccacgc gtgtgcctgt gcctgcagtg tctgcctggg gtgagggctc ccagcttaac

[putative.alt.exon]
actaactgct tcctcctctg ctgctgctgc tgctgccaag [TTTGAGGCCC CGGGGCTTAT

CTCGGAGCAG GCCAGTCTGC TGGACCTGGA CTTTGACCCC CTCCCGCCCG TGACGAGCCC

TGTGAAGGCA CCCACGCCCT CTGGTCAG]gt tggttgtgcc caccactgcc catgggccca ccagcttcca ggtgcccaac cctgggctca tgttgcctat tggccacgtg accccagcta ggcctgggtc actgcccttc ccctggcacc tcagccttca gccctcatca cctcctggtt gtagggcagg aagcagcccc tgatcagctg ggagaactct cagtaggggg ttactgaaca cttcctggca actttgtgct catcgcttgg ggcagaagca tcctggcttg gggtcttgaa gctccctgag aggtgtcggg agctcggcca cctgcaaatc ttggagtcta cctggctccg agccactcct gtgcctgctg ggctggatgg cctggggcga gcggggtag ggtcccctgg ggactgcttg ccgccctgtc tctaacctct gtgctaactg tccttctcgc cctcactgct

[putative.alt.exon]
gcgctcag[TC AATTCCATGG GACCTCTGGG AG]gttaagct gcactctgct ctttgtccac cccctggggg aaccactctt tcccgtatgt gtccaggccc acatgatcat agcctgttca caggtgcatg cacccccacac acccccaca agcaggacac acaggcacgt gctcacgcac agggagntgg tgaagccacc cgcctccagc cattntgntg cttctccctc tggcaggccc ttggaaaagg ggatcttcgg tttagcttga gacagggtc ccctgagatc tggtcctgtt ttcacagcct gtgagtgttt gcctccagac agaaatgggc cggtcaccca ggatggacga gtgtcctcag ggtgtgggc aggagggcct cagggtagaa ggttcttgcc ttctctgagc tttttggcag tggggagctg tttgcgagga aggggagagg ggaggaatgg atggtttgag agaatcaggg aagacagggt gtggctgagt gccttctgag agcagggcct gcaggcaggt gcgaggccat ctcacacagc accatgtcac tgtcacctga tagctcagga cacagaggct cagggaaggc tcagtacttg cccaagaact ggtcatggta gagccagaat ccaacaggg tctcctgggc tctgtccctg agacccctg atacaggcag agatgctggg aggggcaggc gggtgtgcag gcgcccttgg ggcatgcgct ggcagcccag gctcctggga gctctggagg

FIGURE 3L ctccaccgca ggatttccct ctggaggaag ccagaaagag ccagcctggt gcgagctggt agggccattt tgacaagtgg atttcggtag gtgctgagct tgggcagcac agtcacacct

[putative.alt.exon]
gcctgtc[CCT TTGACAGTGG TAGGAGAGAG GATGTGGGAG GCGGGTGGCT GGCCGGGCTC

CGCTGGTACC CACCCTGCCC CCACCAACCC CAGCCGCTGG TGACATTTTC TCTTGTCTTG

TGATCCTGCC CATTGCCTTT CCACCCCGGC CTCCCCGCCC CCTCCCTGTT CTCTCCTCGT

GGCCTGTTAC CAGCCCACAG AGAGTCCAGC CGGCAGCCTG CCTTCCGGGG AGCCCAGCGC

TGCCGAGGGC ACCTTTGCTG TGTCCTGGCC CAGCCAGACG GCCGAGCCGG GGCCTGCCCA

A]gtaagtgcc cacctccagc ccctgtctgg cttgtcccca gtctctaggg gtgcagcatg gaaggagagc cccgaggagg ggttgcagga gggaccaggc caccatggat gtgagggtga ggacagggtc ctgagctagg ctgccccagc acgggcttgt caccaaggct gccaaggatg aatgagcgca ctgggcgcat cagcccctcc tgcttgccca ccccagccca gcctcccacg caggaagaca tttaggacac ctactggttt atgccaggca ctttccagaa tcttctcatt taatcttcgt catcaccttt acagccagac acttcctcct tttacagatg aggagatggg ggctaggagg gttgagtaac ttggttccag cactcagaag tggccaagtc tgagtgtcgg cccaggtcag cccagctctg gggttcctgc agggcctgcc gtggtgcccg tgctgcggtg cccgtgctgc ggtgcccatt tctgtgccac accctttctt ggatttgggc tgcgcacagg cttgcaccgc accacctgcg gtgggttgtt gttcaggctg gganagangt gtgttgntgt cccctgccat ggaatattta taggtgcagc aagatcctgc cacctgccgg gttaagcagg gtgggcgggc ggtggctgtg gtgggcgagg tcttggtgcc gagagagcag ggcctgtgag gcggggttgg gggtggcact atggggcttg cactgggttc ttcacagcat tgtcactcac atccttgggc ntgccagcgc ntactattca gctgcttccc cggcccaggg cccagcttgt ccagcagagg ctcccntgga ttnttcgagg cactgggcag ctctagaccn tgctgccagc caggcgatgc ccccggccct gttgcttggg tgctgccctc ctgtggcctg tttcctgtgt (exon13)
cctggctgtg tcctgtcctg tgtctgaccc caagccggca tttatgttgc agCCAGCAGA

GGCCTCGGAG GTGGCGGGTG GGACCCAACC TGCGGCTGGA GCCCAGGAGC CAGGGGAGAC

GGCGGCAAGT GAAGCAGCCT CCgtaagaca gcagggacaa agccctgcct tttcctccct gccgcccgcc tgcctgtccg gggctcccct gtggcccctg atggtgctgg tccaggcctg gctcctgttg aggaagctgg aggcgggccg gtctggcacc aggcgcagac acctttctcc cctccccgcc cctcttctcc tcggtggccc tggctgtcct tggaccacct tccctgctca

FIGURE 3M (exon14)
gctgacccgt acctctgcca ccaAGCTCTC TTCCTGCTGT CGTGGTGGAG ACCTTCCCAG

CAACTGTGAA TGGCACCGTG GAGGGCGGCT GTGGGGCCGG GCGCTTGGAC CTGCCCCCAG

GTTTCATGTT CAAGgtgagc ccacagcctc tgactgctgc agtccctcgg tgccctggtg ggcagatgac aaccctgagc ctcaggagac tctgtggttt gcccaaagtt gtgcaggcgc tactaggtca ctcccagcca gcaaggtggc atctganccc catacagtcc tgctgctttt gagcactcct ggtctccata ctgccacctg cacctcccac acgcaaggcc cgtgctctgt (exon15)
gcagggctgg aggtgggacg gaaggtctga cttgcgatcc gcatcctctg cagGTACAGG

CCCACCACGA CTACACGGCC ACTGACACAG ACGAGCTGCA GCTCAAGGCT GGTGATGTGG

TGCTGGTGAT CCCCTTCCAC AACCCTGAAG AGCAGgtgag ggctgggtgg gcccccaca ccncangggg accaccnngc atcctggctg cggctggcac cnccgtngcg gatacncgcc attcaggggg cagcagaggc ccgcgagcac cagggctccc gcgccaactg ctcctccccg ccctccacgt cgggcttttt cctctctccc tctcctctcc cttcccttgg ccctctcct gttaggcctc tctctctccc tgtccccata cccgcttctt cctgtagcct ctgctttctt ctccccacgt ccccccttg ctcaggcgct ctcagctctg cctctgtctc tccccttctc ctctcctggc agctgtgcct gaggcctgcc tccctcctgg acaggatgc ttgacccctc ctgccccgcc cacaaggtgc ccaccctgca gccagccgga gcactggttg ggctcatgaa gccccgtgtg ccgtccctcg aggcgggccc tgccctgtgc acncagggcc atgggcttcc cagctgtgtc cccggctgag gctcacccac gatgccttcc agacccttct cctcctgctg tggcttcatg ttaatctcct ggaagtgagg gctcctgttg agcctgggtg ggtgctaagt gtgtccctcc taagtcttgg gacctcctgg atctgggtca gtttgcccct ccccaggggg ccttggaatn atnggcaagg agcttccccg ntgtgtagaa ccnagctttg nttgtggggg gtcggtggtg ccatgtgggc atctggttct tccacggttc agcccctgag cacntcgggc tgtgcacaga gggcctggcc ggttattcct gcttccagag aacatgttta gccatcaacg cttctgtgtg aataggttat cagagcggct gagggtgaca gtgggtctgc ctgggtcttg gatgaggccg accntactgg gggtcctggg ctgggatgta ggggtaccaa gtacttactg aggtccgggg caggaggcct gagtgatgag gaccttgtgg gcctggcact gatttggccc tttctcntaa gccccaggt cttcatggac ctcctagtgg gccagccctg gctgggtagg atttcaagca gactgctacc cagagcccac agtgagaatt ggcctggggn tgctggaggg ggctcagggc atgagtaggg tctgtgacca ggctgacaat gacacagagg gaaataacaa

FIGURE 3N

```
agacccaggt aggccccagg cacagcccag ctgcagggc agcctcggcc cagccactgg caggagtgga tggccatacg gctccccgtg acccacctgg ggccagggc ctgtcagcac tcccagagaa ggccctgcgg gtgtcaggat tgaagcaaag ggcaagtgga agttggaggg actggtggga tggccccaat ccctctagaa ttgtaacttg ttgtcactcc caaaacttcg tggggttgtt tganaagcct gnaatcctgg aagggctgat gtgcacatca tgcatgcagt gggactcatc aaaaccagcc acgaatggtt agatccacct gcggactcac aggctggctc ctgtggtgcc tctgggcagg agcctcagcc agcancatca gggagtgctg cctggaggag gtgttctcaa ggtgggcttg gcaggctgag gcaccaacag caggaggagg ggccgtcttc ccagcaggtt ggagtgggat gcgtgccctg tggggtggan ccccttgctc atccctgtgc
                                                               (exon16)
gacctgntgc tctgccctc agGATGAAGG CTGGCTCATG GGCGTGAAGG AGAGCGACTG

GAACCAGCAC AAGAAGCTGG AGAAGTGCCG TGGCGTCTTC CCCGAGAACT TCACTGAGAG

GGTCCCATGA CGGCGGGGCC CAGGCAGCCT CCGGGCGTGT GAAGAACACC TCCTCCCGAA

AAATGTGTGG TTCTTTTTTT TGTTTTGTTT TCGTTTTTCA TCTTTTGAAG AGCAAAGGGA

AATCAAGAGG AGACCCCCAG GCAGAGGGGC GTTCTCCCAA AGTTTAGGTC GTTTTCCAAA

GAGCCGCGTC CCGGCAAGTC CGGCGGAATT CACCAGTGTT CCTGAAGCTG CTGTGTCCTC

TAGTTGAGTT TCTGGCGCCC CTGCCTGTGC CCGCATGTGT GCCTGGCCGC AGGGCGGGGC

TGGGGGCTGC CGAGCCACCA TACTTAACTG AAGCTTCGGC CGCACCACCC GGGGAAGGGT

CCTCTTTTCC TGGCAGCTGC TGTGGGTGGG GCCCAGACAC CAGCCTAGCC TGCTCTGCCC

CGCAGACGGT CTGTGTGCTG TTTGAAAATA AATCTTAGTG TTCaaaacaa aatgaaacaa aaaaaaaatg ataaaaactc tcagaaaacg tgtgtgtatt tgttctccct cttcttgtcc gtgagtgcgg atggaaccgt gtnatctgtg gctttcttac tgagatggtc tgccccgaa ggcccgctgc cctgncgctg gtgcaccaca gggcttcacc ccctgtcccc tggggttctt aggggtggtc acctggangt canggactgg gggcttgggt taagggcctt ggccacccat ctcttgtccc anaaatcttg ctnactgccc ccctaact
```

MURINE AND HUMAN BOX-DEPENDENT MYC-INTERACTING PROTEIN (BIN1) AND USES THEREFOR

CROSS-REFERENCE TO RELATED APPLICATION

This is a continuation-in-part of U.S. patent application Ser. No. 08/652,972, filed May 24, 1996, now U.S. Pat. No. 5,723,581, which is a continuation-in-part of U.S. patent application Ser. No. 08/435,454, filed May 5, 1995, now U.S. Pat. No. 5,605,830.

This invention was made with financial assistance from the National Institutes of Health Grant No. 5-P30-CA-10815-28. The United States government has certain rights in this invention.

FIELD OF THE INVENTION

This invention relates generally to cancer diagnosis and therapy, and more specifically, to cancers associated with the Myc oncoprotein.

BACKGROUND OF THE INVENTION

Myc is a transcription factor and key cell growth regulator that is frequently deregulated in human malignancy, notably Burkitt's and T cell lymphomas, where myc genes suffer chromosomal translocation. In colon and lung carcinomas, myc genes are amplified [M. D. Cole, *Ann. Rev. Genet.*, 20:361–384 (1986)]. Paradoxically, under certain conditions myc can induce apoptosis, a regulated cell suicide process [D. S. Askew et al, *Oncogene*, 6:1915–1922 (1991); G. I. Evan et al, *Cell*, 69:119–128 (1992)]. However, loss or suppression of apoptosis is an important step in the malignant conversion of human tumors containing deregulated myc oncogenes, including, prominently, prostate carcinoma [T. G. Strohmeyer et al, *J. Urol.*, 151:1479–1497 (1994)].

There remains a need in the art for compositions and methods of regulating a deregulated Myc protein and of exploiting and/or diagnosing its apoptotic potential.

SUMMARY OF THE INVENTION

In one aspect, the present invention provides a partial murine cDNA clone of a Box-dependent myc-interacting polypeptide 1 (Bin1), formerly referred to as c-Myc interacting peptide (MIP or MIP-99), SEQ ID NO:1, and the polypeptide encoded thereby, SEQ ID NO:2.

In another aspect, the present invention provides a human Bin1 cDNA clone, SEQ ID NO:3, and the human polypeptide encoded thereby, SEQ ID NO:4.

In yet another aspect, the present invention provides a vector comprising a mammalian nucleic acid sequence encoding a Bin1 protein and a host cell transformed by such a vector. Alternatively, this vector may be used in gene therapy applications.

In still another aspect, the invention provides an oligonucleotide probe comprising a nucleic acid sequence as defined herein. Also provided is an antibody raised against a Bin1 protein or peptide thereof.

In yet a further aspect, the present invention provides a diagnostic reagent for breast, prostate, or liver cancer, or deficient Bin1 production, comprising an oligonucleotide probe or an antibody of the invention.

Further provided is a therapeutic reagent comprising a polypeptide, anti-idiotype antibody, or gene therapy vector of the invention.

Still another aspect of the invention provides a method of treating breast, prostate, or liver cancer by administering a therapeutic reagent of the invention.

Other aspects and advantages of the present invention are described further in the following detailed description of the preferred embodiments thereof.

BRIEF DESCRIPTION OF THE DRAWINGS

FIG. 1 is a partial murine cDNA sequence SEQ ID NO:1 and the murine Bin1 polypeptide encoded thereby SEQ ID NO:2.

FIGS. 2A–2C is a human cDNA sequence SEQ ID NO:3 and the human Bin1 polypeptide encoded thereby SEQ ID NO:4.

FIGS. 3A–3N is the partial human genomic BIN1 sequences [SEQ ID NOS: 7–12]. Exons are shown in capital letters and introns in lower case letters. The summary preceding each segment of the sequence indicates the exons included in that segment and the plasmid clone(s) sequenced. Five putative alternate exons in the sequence are bracketed. Putative translation initiation and termination sites are underlined.

DETAILED DESCRIPTION OF THE INVENTION

Figure 4A:
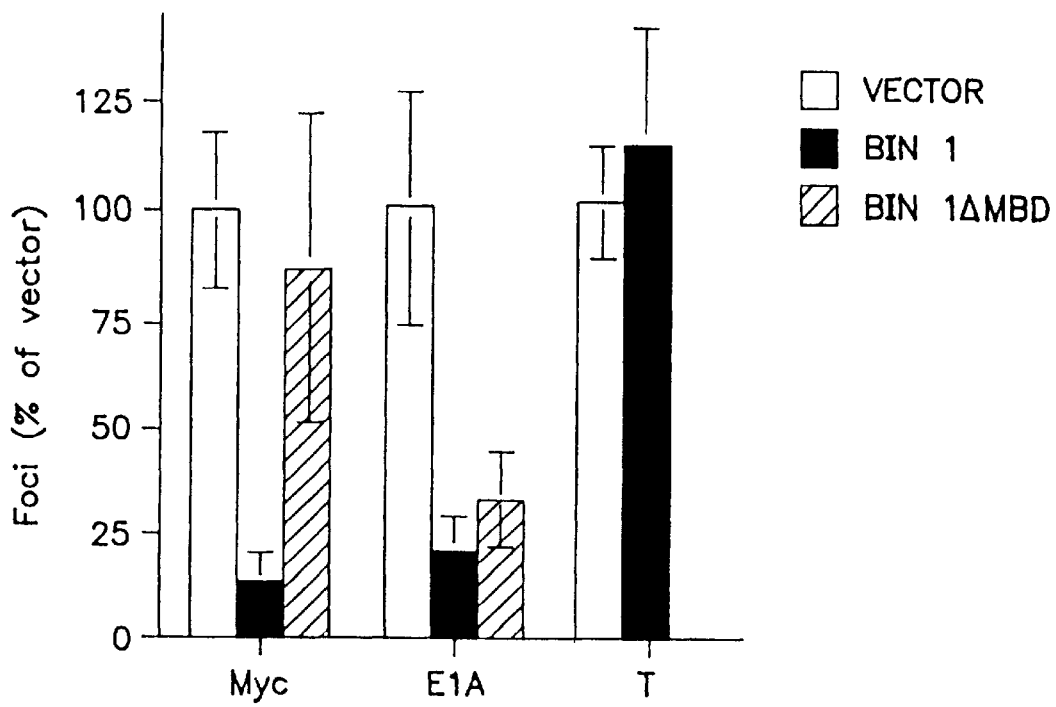
FIG. 4A is a bar chart illustrating the selective requirement of the Myc-binding domain (MBD) for Myc inhibition, as described in Example 7. The data represent three to seven trials for each transfection. The data are depicted as the percent of foci induced by oncogenes and vector, as appropriate.

The present invention provides novel, isolated, nucleic acid sequences which encode novel proteins which interact with c-Myc and bind thereto, fragments of these sequences and antibodies developed thereto. The nucleic acid sequences, protein sequences and antibodies are useful in the detection, diagnosis and treatment of cancers or other disorders associated with deregulation, deficiency or amplification of the c-myc oncogenes. Further, when a Box-dependent myc-interacting polypeptide 1 (called Bin1) of this invention binds to c-Myc, the binding appears to regulate the c-Myc and result in tumor suppression, by inhibiting cell growth and/or facilitating apoptosis (programmed cell death). The Bin1 gene has several other features suggesting it is a tumor suppressor gene. First, Bin1 inhibits Myc-dependent malignant cell transformation. Second, Bin1 is structurally related to RVS167, a negative regulator of the cell division cycle in the yeast *Saccharomyces cerevisiae* [F. Bauer et al, *Mol. Cell. Biol.*, 13:5070–5084 (1993)]. Third, Northern analysis indicates that expression of Bin1 RNA is ubiquitous in normal tissues but frequently missing in carcinoma cell lines. Fourth, Bin1 selectively inhibits the growth of carcinoma cells lacking endogenous expression. These results show that the observed expression deficits are functionally significant, rather than simply correlated with loss of genomic integrity, and formally demonstrate that Bin1 can act as a tumor suppressor. Fifth, chromosomal mapping has identified Bin1's location at 2q14, a locus lying within a mid-2q region deleted in 42% of metastatic prostate cancers [M. L. Cher et al, *Cancer Res.,* 56:3091–3101 (1996)] and, at the syntenic murine locus, in 90% of radiation-induced leukemias [I. Hayata et al, *Cancer Res.,* 43:367–373 (1983)].

Further, using a set of monoclonal antibodies, characterized herein, cellular BIN1 has been identified as an unstable nuclear phosphoprotein(s) that is constitutively expressed in proliferating cells. In addition, antibodies recognizing different epitopes have been identified in BIN1 species that were located in different compartments of the cell. Antibodies recognizing the C-terminal region of the Bin1/amphiphysin/RVS167-related domain (BAR-C), Myc-binding domain (MBD), or nuclear localization signal (NLS) regions of BIN1 identified species located in a subnuclear punctate structure(s), the nucleoplasm, or the nucleus and cytoplasm, respectively. Notably, the localization patterns defined by these antibodies were associated with different cell states. In proliferating cells, BIN1 was located predominantly in the nucleoplasm, but a fraction of the protein could also be detected in the subnuclear punctate structure(s). In tumor cells, the subnuclear pattern predominated. Finally, in differentiated muscle cells, BIN1 species could be detected in both the nucleus and cytoplasm. Taken together, these results indicate that the localization of BIN1 species in cells correlates with the ability to regulate proliferation.

Thus, Bin1 has been identified as a tumor suppressor gene, similar to the breast cancer gene BRCA1, and the genes encoding p53 and the Rb retinoblastoma protein, which are negative regulators of cell growth that are observed to be mutated and/or unexpressed in human cancer cells. The Bin1 protein specifically interacts with Myc and inhibits its oncogenic activity. These aspects of the invention are discussed in more detail below.

I. Nucleic Acid Sequences

The present invention provides mammalian nucleic acid sequences encoding a Box-dependent myc-interacting polypeptide 1, termed herein Bin1. The nucleic acid sequences of this invention are isolated from cellular materials with which they are naturally associated. In one embodiment, a Bin1 nucleic acid sequence is selected from all or part of the partial murine cDNA clone, SEQ ID NO: 1. In another embodiment, a Bin1 nucleic acid sequence is selected from all or part of a human cDNA clone, SEQ ID NO: 3. In yet another embodiment, the present invention provides partial Bin1 genomic sequences, SEQ ID NOS: 7–12. However, the present invention is not limited to these nucleic acid sequences.

Given the sequences of SEQ ID NO: 1, SEQ ID NO: 3, and SEQ ID NOS: 7–12, one of skill in the art can readily obtain the corresponding anti-sense strands of these cDNA and genomic sequences. Further, using known techniques, one of skill in the art can readily obtain further genomic sequences corresponding to these cDNA sequences or the corresponding RNA sequences, as desired.

Similarly the availability of SEQ ID NOS: 1, 3 and 7–12 of this invention permits one of skill in the art to obtain other species Bin1 analogs, by use of the nucleic acid sequences of this invention as probes in a conventional technique, e.g., polymerase chain reaction. Allelic variants of these sequences within a species (i.e., nucleotide sequences containing some individual nucleotide differences from a more commonly occurring sequence within a species, but which nevertheless encode the same protein) such as other human variants of Bin1 SEQ ID NO: 3, may also be readily obtained given the knowledge of this sequence provided by this invention.

The present invention further encompasses nucleic acid sequences capable of hybridizing under stringent conditions [see, J. Sambrook et al, *Molecular Cloning: A Laboratory Manual,* 2d ed., Cold Spring Harbor Laboratory (1989)] to the sequences of SEQ ID NO: 1, SEQ ID NO: 3, SEQ ID NOS: 7–12, their anti-sense strands, or biologically active fragments thereof. An example of a highly stringent hybridization condition is hybridization at 2×SSC at 65° C., followed by a washing in 0.1×SSC at 65° C. for an hour. Alternatively, an exemplary highly stringent hybridization condition is in 50% formamide, 4×SSC at 42° C. Moderately high stringency conditions may also prove useful, e.g. hybridization in 4×SSC at 55° C., followed by washing in 0.1×SSC at 37° C. for an hour. An alternative exemplary moderately high stringency hybridization condition is in 50% formamide, 4×SSC at 30° C.

Also encompassed within this invention are fragments of the above-identified nucleic acid sequences. Preferably, such fragments are characterized by encoding a biologically active portion of Bin1, e.g., an epitope. Generally, these oligonucleotide fragments are at least 15 nucleotides in length. However, oligonucleotide fragments of varying sizes may be selected as desired. Such fragments may be used for such purposes as performing the PCR, e.g., on a biopsied tissue sample. For example, one fragment which is anticipated to be particularly useful is the Src homology 3 (SH3) domain, which is located at about nucleotides 1191–1412 of SEQ ID NO: 3 (which encode amino acid residues 378–451 of SEQ ID NO: 4). Preliminary data has indicated this domain may be useful in blocking apoptosis. Other useful fragments include about nucleotides 813–854 of SEQ ID NO: 3 (encoding a nuclear localization signal, amino acid residues about 252–265 of SEQ ID NO: 4), nucleotides about 867–1206 (a Myc-binding domain or MBD amino acids 270–383). Other useful fragments may be readily identified by one of skill in the art by resort to conventional techniques.

The nucleotide sequences of the invention may be isolated by conventional uses of polymerase chain reaction or cloning techniques such as those described in obtaining the murine and human sequences, described below. Alternatively, these sequences may be constructed using conventional genetic engineering or chemical synthesis techniques.

According to the invention, the nucleic acid sequences [SEQ ID NO: 1, SEQ ID NO: 3, and SEQ ID NOS: 7–12] may be modified. Utilizing the sequence data in these figures and in the sequence listing, it is within the skill of the art to obtain other polynucleotide sequences encoding the proteins of the invention. Such modifications at the nucleic acid level include, for example, modifications to the nucleotide sequences which are silent or which change the amino acids, e.g. to improve expression or secretion. Also included are allelic variations, caused by the natural degeneracy of the genetic code.

Also encompassed by the present invention are mutants of the Bin1 gene provided herein. Such mutants include amino terminal, carboxy terminal or internal deletions which are useful as dominant inhibitor genes. Such a truncated, or deletion, mutant may be expressed for the purpose of inhibiting the activity of the full-length or wild-type gene. For example, it has been found that expression of the partial murine Bin1 provided herein [SEQ ID NO:2] acts in a dominant inhibitory manner to suppress normal Bin1 activity. Expression of this protein is described in Example 4 below. Another mutant encodes Bin1 deleted in the region encoding the MBD domain (amino acid residues 270–383 of SEQ ID NO: 4).

The invention further provides a partial human Bin1 gene and promoter region. The BIN1 message is encoded by 16 exons which span a ≧54 kb genomic region which mapped to chromosome 2q14. The primary BIN1 transcript undergoes extensive alternate splicing to generate at least 7 different RNA species with unique coding potentials. Further, the BIN1 promoter has been identified and a region has been defined which is sufficient to direct transcription in muscle cells, where BIN1 is highly expressed. As illustrated in FIGS. 3A–3N, the partial Bin1 genomic sequences include, from 5' to 3', the 5' flanking region and exon 1 [SEQ ID NO: 7], a >10 kb gap; the 5' end of chromosome p21.1 [SEQ ID NO: 8]; a 6 kb gap; exon 2 [SEQ ID NO: 9], a 4–5 kb gap; exons 3–6 [SEQ ID NO: 10], a 3–4 kb gap; exons 7–12 and a putative brain specific alternate exon sequence [SEQ ID NO: 11], a 2–3 kb gap; and exons 13–16 plus three putative brain-specific alternate exons [SEQ ID NO: 12]. More detailed discussion of the Bin1 genomic sequence is provided in Example 3. The exon-intron junction sequences derived are desirable for applying PCR technology to identify mutations in DNA derived from tumor biopsies, using techniques similar to those applied to sequences derived from other tumor suppressor genes (e.g., p53 and BRCA1). The sequenced region of the Bin1 gene spans regions previously found to be rearranged in liver and cervix carcinoma cell lines, making it possible to map deletions and possible mutations in primary human tumor DNA by PCR technology. Using the genomic clones, the human Bin1 gene has been mapped to chromosome 2q14, a region frequently deleted in prostate carcinoma and in radiation-induced malignancies. These nucleic acid sequences are useful for a variety of diagnostic and therapeutic uses. Advantageously, the nucleic acid sequences are useful in the development of diagnostic probes and antisense probes for use in the detection and diagnosis of conditions characterized by deregulation or amplification of c-myc. The nucleic acid sequences of this invention are also useful in the production of mammalian, and particularly, murine and human Bin1 proteins.

II. Protein Sequences

The present invention also provides mammalian Bin1 polypeptides or proteins. These proteins are free from association with other contaminating proteins or materials with which they are found in nature. In one embodiment, the invention provides a partial murine Bin1 [SEQ ID NO:2] polypeptide of 135 amino acids having a predicted molecular weight (MW) of 13,688. In another embodiment, the invention provides a full-length human Bin1 [SEQ ID NO:4] of 451 amino acids with an estimated MW of 50,048. The apparent MW of human Bin1 on sodium dodecyl sulfate polyacrylamide (SDS-PA) gels is approximately 70 kD. Data provided herein shows that the Bin1 DNA encodes a nuclear protein which is identical to a protein found in normal human fibroblasts.

Further encompassed by this invention are fragments of the Bin1 polypeptides. Such fragments are desirably characterized by having Bin1 biological activity, including, e.g., the ability to interact with c-Myc. These fragments may be designed or obtained in any desired length, including as small as about 8 amino acids in length. Such a fragment may represent an epitope of the protein. One particularly desirable fragment is located at amino acid residues 270–383 of SEQ ID NO: 4, which is the c-Myc binding domain (MBD) of particular interest within the MBD is the fragment at amino acids 323–389 of SEQ ID NO: 4. Another desirable fragment is located at residues 378–451 of SEQ ID NO: 4 and is a Src homology 3 (SH3) domain. A third fragment is located at residues 223–251 of SEQ ID NO:4 and includes the T antigen/RED1/p93dis1 motifs discussed herein. Yet another desirable fragment includes the N-terminal region, amino acid residues 1–250 of SEQ ID NO:4. Of particular interest within this domain are the C-terminal end of the BAR domain (BAR-C), located at amino acids 143–148 of SEQ ID NO: 4. Also of interest in this N-terminal region is a unique region (U1), located at amino acids 225–250 of SEQ ID NO: 4. Finally, a fragment containing the nuclear localization signal (NLS)-like domain located at amino acid residues 252 to about 265 of SEQ ID NO: 4, may also be desirable. These and other fragments are discussed herein.

Also included in the invention are analogs, or modified versions, of the proteins provided herein. Typically, such analogs differ by only one to four codon changes. Examples include polypeptides with minor amino acid variations from the illustrated amino acid sequences of Bin1 (FIGS. 1 and 2; SEQ ID NOS:2 and 4); in particular, conservative amino acid replacements. Conservative replacements are those that take place within a family of amino acids that are related in their side chains and chemical properties. Also provided are homologs of the proteins of the invention which are characterized by having at least 85% homology with SEQ ID NO:2 or SEQ ID NO:4. It has previously determined that the murine and human Bin1 (in partial) are about 88.5% identical.

Further included in the invention are homologs of Bin1. Based on the sequence information provided herein, one of skill in the art can readily obtain Bin1 from other mammalian species. Such homologs are typically at least 85% homologous with SEQ ID NO: 2 or SEQ ID NO: 4.

Additionally, the Bin1 proteins [SEQ ID NOS:2 and 4] of the invention may be modified, for example, by truncation at the amino or carboxy termini, by elimination or substitution of one or more amino acids, or by any number of now conventional techniques to improve production thereof, to enhance protein stability or other characteristics, e.g. binding activity or bioavailability, or to confer some other desired property upon the protein.

III. Expression

A. In Vitro

To produce recombinant Bin1 proteins of this invention, the DNA sequences of the invention are inserted into a suitable expression system. Desirably, a recombinant molecule or vector is constructed in which the polynucleotide sequence encoding Bin1 is operably linked to a heterologous expression control sequence permitting expression of the murine or human Bin1 protein. Numerous types of appropriate expression vectors are known in the art for mammalian (including human) protein expression, by standard molecular biology techniques. Such vectors may be selected from among conventional vector types including insects, e.g., baculovirus expression, or yeast, fungal, bacterial or viral expression systems. Other appropriate expression vectors, of which numerous types are known in the art, can also be used for this purpose.

Methods for obtaining such expression vectors are well-known. See, Sambrook et al, *Molecular Cloning. A Laboratory Manual*, 2d edition, Cold Spring Harbor Laboratory, New York (1989); Miller et al, *Genetic Engineering*, 8:277–298 (Plenum Press 1986) and references cited therein.

Suitable host cells or cell lines for transfection by this method include mammalian cells, such as Human 293 cells, Chinese hamster ovary cells (CHO), the monkey COS-1 cell line or murine 3T3 cells derived from Swiss, Balb-c or NIH mice may be used. Another suitable mammalian cell line is the CV-1 cell line. Still other suitable mammalian host cells, as well as methods for transfection, culture, amplification, screening, production, and purification are known in the art. [See, e.g., Gething and Sambrook, Nature, 293:620–625 (1981), or alternatively, Kaufman et al, Mol. Cell. Biol., 5(7):1750–1759 (1985) or Howley et al, U.S. Pat. No. 4,419,446].

Similarly bacterial cells are useful as host cells for the present invention. For example, the various strains of E. coli (e.g., HB101, MC1061, and strains used in the following examples) are well-known as host cells in the field of biotechnology. Various strains of B. subtilis, Pseudomonas, other bacilli and the like may also be employed in this method. Many strains of yeast cells known to those skilled in the art are also available as host cells for expression of the polypeptides of the present invention. Other fungal cells may also be employed as expression systems.

Alternatively, insect cells such as Spodoptera frugipedera (Sf9) cells may be used.

Thus, the present invention provides a method for producing a recombinant Bin1 protein which involves transfecting a host cell with at least one expression vector containing a recombinant polynucleotide encoding a Bin1 protein under the control of a transcriptional regulatory sequence, e.g., by conventional means such as electroporation. The transfected host cell is then cultured under conditions that allow expression of the Bin1 protein. The expressed protein is then recovered, isolated, and optionally purified from the culture medium (or from the cell, if expressed intracellularly) by appropriate means known to one of skill in the art.

For example, the proteins may be isolated in soluble form following cell lysis, or may be extracted using known techniques, e.g., in guanidine chloride. If desired, the Bin1 proteins of the invention may be produced as a fusion protein. For example, it may be desirable to produce Bin1 fusion proteins, to enhance expression of the protein in a selected host cell, to improve purification, or for use in monitoring the presence of Bin1 in tissues, cells or cell extracts. Suitable fusion partners for the Bin1 proteins of the invention are well known to those of skill in the art and include, among others, β-galactosidase, glutathione-S-transferase, and poly-histidine.

B. In Vivo

Alternatively, where it is desired that the Bin1 protein be expressed in vivo, e.g., for gene therapy purposes, an appropriate vector for delivery of Bin1, or fragment thereof (such as the SH3 domain), may be readily selected by one of skill in the art. Exemplary gene therapy vectors are readily available from a variety of academic and commercial sources, and include, e.g., adeno-associated virus [International patent application No. PCT/US91/03440], adenovirus vectors [M. Kay et al, Proc. Natl. Acad. Sci. USA, 91:2353 (1994); S. Ishibashi et al, J. Clin. Invest., 92:883 (1993)], or other viral vectors, e.g., various poxviruses, vaccinia, etc. Methods for insertion of a desired gene, e.g. Bin1, and obtaining in vivo expression of the encoded protein, are well known to those of skill in the art.

IV. Antisera and Antibodies

The Bin1 proteins of this invention are also useful as antigens for the development of anti-Bin1 antisera and antibodies to Bin1 or to a desired fragment of a Bin1 protein. Specific antisera may be generated using known techniques. See, Sambrook, cited above, Chapter 18, generally, incorporated by reference. Similarly, antibodies of the invention, both polyclonal and monoclonal, may be produced by conventional methods, including the Kohler and Milstein hybridoma technique, recombinant techniques, such as described by Huse et al, Science, 246:1275–1281 (1988), or any other techniques known to the art. For example, rabbit polyclonal antisera was developed and recognizes an epitope(s) between amino acid residues 190–250 of SEQ ID NO: 4. This antisera appears to be human-specific. Since amino acids 190–250 are outside the MBD and SH3 domain, for experimental needs two additional antisera have been raised to these regions. The immunogens included human Bin1 amino acids 270–383 (MBD) [SEQ ID NO: 4] or amino acids 378–451 (SH3) [SEQ ID NO: 4]. Each antisera has been shown to recognize the appropriate domain by immunoprecipitation.

Additionally, six (6) Bin1-specific monoclonal antibodies, termed 99-D through 99-I, have been characterized. The approximate location of the epitopes within Bin1 for each antibody has been mapped. MAb 99D recognizes an epitope within a 33 residue segment of the MBD amino acids 323–356 [SEQ ID NO: 4]; MAbs 99F–99I recognize epitopes which are within the NLS-like domain (amino acids 252–269 [SEQ ID NO: 4]); MAb 99E recognizes a complex epitope requiring amino acids 190–250 and amino acids 323–356 [SEQ ID NO: 4]. Each antibody has been isotyped and demonstrated to work in immunoprecipitation, Western blotting, and immunohistochemistry methodology. Particularly, MAb 99D and MAb 99F are IgG2b isotypes; MAbs 99E, 99G and 99H are IgG1 isotypes. Further, MAbs 99D and 99F have been determined to be useful for immunohistochemistry with sectioned biopsy tissue and tissue culture cells, and are therefor likely to be useful for clinical applications to analyze tumor biopsies.

MAb 99D has been found to be a "pan" antibody in the sense that it recognized BIN1 species in the nucleoplasm, a subnuclear punctate compartment, and the cytoplasm. Since it recognizes a region of the MBD, MAb 99D is expected to be useful for inhibition of MYC interaction in vitro or in vivo. 99E recognized a noncontiguous epitope composed of BAR-C and MBD elements that was detected only on cellular BIN1 species located in a subnuclear compartment. The contribution of BAR-C and MBD elements to the epitope suggested that these regions may be proximal to each other in certain forms of native BIN1. MAb 99F, which recognized an NLS epitope, detected only a subset of cellular BIN1 species in the nucleoplasm and cytosol that were present in differentiated but not proliferating C2C12 myoblasts. MAbs 99D and 99F have further been shown to recognize both murine and human Bin1 polypeptides, and MAb 99D to also recognize avian Bin1.

Hybridomas secreting Mabs 99-D (ATCC HB-12580) and 99-I (ATCC HB-12581) were deposited with the American Type Culture Collection, 10801 University Boulevard, Manassas, Va. 20110-2209, on Sep. 9, 1998, pursuant to the provisions of the Budapest Treaty.

Also encompassed within this invention are humanized and chimeric antibodies. As used herein, a humanized antibody is defined as an antibody containing murine complementary determining regions (CDRs) capable of binding to Bin1 or a fragment thereof, and human framework regions. These CDRs are preferably derived from a murine monoclonal antibody (MAb) of the invention. As defined herein, a chimeric antibody is defined as an antibody containing the variable region light and heavy chains, including both CDR and framework regions, from a Bin1 MAb of the invention and the constant region light and heavy chains from a human antibody. Methods of identifying suitable human framework regions and modifying a MAb of the invention to contain same to produce a humanized or chimeric antibody of the invention, are well known to those of skill in the art. See, e.g., E. Mark and Padlin, "Humanization of Monoclonal Antibodies", Chapter 4, *The Handbook of Experimental Pharmacology*, Vol. 113, The Pharmacology of Monoclonal Antibodies, Springer-Verlag (June, 1994). Other types of recombinantly-designed antibodies are also encompassed by this invention.

Further provided by the present invention are anti-idiotype antibodies (Ab2) and anti-anti-idiotype antibodies (Ab3). Ab2 are specific for the target to which anti-Bin1 antibodies of the invention bind and Ab3 are similar to Bin1 antibodies (Ab1) in their binding specificities and biological activities [see, e.g., M. Wettendorff et al., "Modulation of anti-tumor immunity by anti-idiotypic antibodies." In *Idiotypic Network and Diseases*, ed. by J. Cerny and J. Hiernaux J, Am. Soc. Microbiol., Washington D.C.: pp. 203–229, (1990)]. These anti-idiotype and anti-anti-idiotype antibodies may be produced using techniques well known to those of skill in the art. Such anti-idiotype antibodies (Ab2) can bear the internal image of the c-Myc and bind to it in much the same manner as Bin1 and are thus useful for the same purposes as Bin1.

In general, polyclonal antisera, monoclonal antibodies and other antibodies which bind to Bin1 as the antigen (Ab1) are useful to identify epitopes of Bin1, to separate Bin1 from contaminants in living tissue (e.g., in chromatographic columns and the like), and in general as research tools and as starting material essential for the development of other types of antibodies described above. Anti-idiotype antibodies (Ab2) are useful for binding c-Myc and thus may be used in the treatment of cancers in which c-Myc is part of a biochemical cascade of events leading to tumor formation. The Ab3 antibodies may be useful for the same reason the Ab1 are useful. Other uses as research tools and as components for separation of c-Myc from other contaminant of living tissue, for example, are also contemplated for these antibodies.

V. Diagnostic Reagents and Methods

Advantageously, the present invention provides reagents and methods useful in detecting and diagnosing abnormal levels of Bin1, and particularly deficiencies or excess production thereof, in a patient. As defined herein, a deficiency of Bin1 is an inadequate amount of Bin1 to compensate for the levels of c-Myc in a patient. Conditions associated with deficiencies of Bin1 include a variety of cancers, e.g., breast cancer, prostate cancer, liver cancer and colon cancer, and hyperplastic disease states, e.g., benign prostate hyperplasia.

Thus, the proteins, protein fragments, antibodies, and polynucleotide sequences (including anti-sense polynucleotide sequences and oligonucleotide fragments), and Bin1 antisera and antibodies of this invention may be useful as diagnostic reagents. These reagents may optionally be labelled using diagnostic labels, such as radioactive labels, calorimetric enzyme label systems and the like conventionally used in diagnostic or therapeutic methods. Alternatively, the N-or C-terminus of Bin1 or a fragment thereof may be tagged with a viral epitope which can be recognized by a specific antisera. The reagents may be used to measure abnormal Bin1 levels in selected mammalian tissue in conventional diagnostic assays, e.g., Southern blotting, Northern and Western blotting, polymerase chain reaction (PCR), reverse transcriptase (RT) PCR, immunostaining, and the like. For example, in biopsies of tumor tissue, loss of Bin1 expression in tumor tissue could be directly verified by RT-PCR or immunostaining. Alternatively, a Southern analysis, genomic PCR, or fluorescence in situ hybridization (FISH) may be performed to confirm Bin1 gene rearrangement.

In one example, as diagnostic agents the polynucleotide sequences may be employed to detect or quantitate normal Bin1. The selection of the appropriate assay format and label system is within the skill of the art and may readily be chosen without requiring additional explanation by resort to the wealth of art in the diagnostic area.

Thus the present invention provides methods for the detection of disorders characterized by insufficient Bin1 levels. Currently, it is anticipated that antibodies of the invention, such as MAbs 99D and 99F, which have been found to be able to withstand the conditions necessary for tissue fixation, will be particularly useful for biopsies. However, the protein, antibody, antisera or polynucleotide reagents of the invention are expected to be similarly useful in the following methods. The methods involve contacting a selected mammalian tissue, e.g., a biopsy sample or other cells, with the selected reagent, protein, antisera antibody or DNA sequence, and measuring or detecting the amount of Bin1 present in the tissue in a selected assay format based on the binding or hybridization of the reagent to the tissue.

VI. Therapeutic Compositions and Methods

Compositions and methods useful for the treatment of conditions associated with inadequate Bin1 levels are provided. As stated above, included among such conditions are liver, colon, prostate, and breast cancers and hyperplastic disease states. Also provided are compositions and methods for inhibiting Bin1 activity in order to ameliorate a condition in which apoptosis is activated and Bin1 plays a role. Such conditions may include degenerative conditions, e.g., neurodegenerative diseases.

The therapeutic compositions of the invention may be formulated to contain an anti-idiotype antibody of the invention, the Bin1 protein itself or a fragment thereof. The therapeutic composition desirably contains 0.01 $\mu$g to 10 mg protein. Such a composition may contain the Bin1 SH3 domain (amino acids 278–451 of SEQ ID NO: 4) and be administered to mimic the effect of normal Bin1 and bind c-Myc, thereby preventing its cancer causing function. These compositions may contain a pharmaceutically acceptable carrier. Suitable carriers are well known to those of skill in the art and include, for example, saline. Alternatively, such compositions may include conventional delivery systems into which protein of the invention is incorporated. Optionally, these compositions may contain other active ingredients, e.g., chemotherapeutics.

Still another method involves the use of the Bin1 polynucleotide sequences for gene therapy. In the method, the Bin1 sequences are introduced into a suitable vector for delivery to a cell containing a deficiency of Bin1 and/or to block tumor growth. By conventional genetic engineering techniques, the Bin1 gene sequence may be introduced to mutate the existing gene by recombination or to replace an inactive or missing gene.

Generally, a suitable polynucleotide-based treatment contains between $1 \times 10^{-3}$ pfu to $1 \times 10^{12}$ pfu per dose. However, the dose, timing and mode of administration of these compositions may be determined by one of skill in the art. Such factors as the age, condition, and the level of the Bin1 deficiency detected by the diagnostic methods described above, may be taken into account in determining the dose, timing and mode of administration of the therapeutic compositions of the invention. Generally, where treatment of an existing cancer or hyperplastic state is indicated, a therapeutic composition of the invention is preferably administered in a site-directed manner and is repeated as needed. Such therapy may be administered in conjunction with conventional therapies, including radiation and/or chemotherapeutic treatments.

The following examples illustrate the isolation and use of the Bin1 sequences of the invention. These examples are illustrative only and do not limit the scope of the invention.

EXAMPLE 1

Identification and Characterization of Bin1

A. Murine Bin1 cDNA

A yeast two hybrid approach [Fields, S. and O. Song., Nature, 340:245–6 (1989)] was used to screen for Myc-interacting proteins (Bin1) in a murine embryo E10.5 cDNA library. The cDNA library was derived from day 10.5 mouse embryonic RNA [A. B. Vojtek et al, Cell, 74: 205–214 (1993)]. This system takes advantage of the modular nature of transcription factors, whose DNA-binding and transcriptional activating components can be assembled in trans by interacting protein (IP) domains derived from other polypeptides. A previously described two hybrid system [Vojtek et al, cited above] and a 16 amino acid nontransactivating polypeptide derived from the human c-Myc "Myc box 1" (MB1) region [Prendergast, G. C. and E. B. Ziff, Trends in Genet., 8: 91–96.3 (1992)] EDIWKKFELLPTPPLS (human c-Myc amino acids 47–62) [SEQ ID NO:5], were used as "bait" in the screen.

Briefly, the "bait" plasmid contained a TRP1 marker and a LexA-MB1 fusion protein as the DNA binding component, and the cDNA library vector, pVP16, contained a LEU2 marker and the herpes simplex virus VP16 protein as the transcriptional transactivator fused to the cDNA library inserts. cDNA synthesized from the 10.5 day murine embryo RNA was size-selected by random DNaseI treatment to ~0.05 kb, treated with Klenow enzyme, NotI linked, and subcloned into pVP16. This cDNA library was designed to express protein modules whose interactions might be occluded in full-length polypeptides. The yeast strain L40 (MATa trp1-901 leu2-3,112 LYS2:(lexAop)4-HIS3 URA3:: (lexAop)8-lacZ) served as the host for the two hybrid screen [see, Vojtek et al, cited above].

An L40 derivative expressing the MB1 "bait" was transfected with the cDNA library and approximately 3×10$^7$ TRP+LEU+ transformants were examined in the primary screen, 300–400 of which were also the HIS+LacZ+ phenotype, which is diagnostic for interaction between the "bait" and library components [Vojtek et al, cited above]. The clones were cured of the original "bait" plasmid by standard methods [Guthrie, C. and G. R. Fink, eds., Guide to Yeast Genetics and Molecular Biology, Meth. Enzymol., 194, Academic Press: New York (1991)]. One hundred clones cured of the bait plasmid were tested for interaction by a mating strategy with a set of test baits.

The test "baits" included the original lexA-MB1 peptide construct, a set of negative controls that included no insert, lamin [A. B. Vojtek et al, Cell, 74:205–214 (1993)], the small GTP-binding protein RhoB [D. Jahner, Mol. Cell. Biol., 11:3682–3690 (1991)], the peptide FTRHPPVLTPP-DQEVI [SEQ ID NO: 6] derived from rat protein kinase Cβ2, a mutant MB1 peptide, a similarly sized but nonspecific peptide derived from protein kinase C, or lamin. The protein kinase C (PKC) peptide contained a phosphorylation site structurally analogous to the MB1 T58 phosphorylation site, which is recognized by glycogen synthase kinase-3 (GSK-3), a kinase present in yeast. The PKC peptide was designed to control for binding proteins that might non-specifically interact with phosphooligopeptides (e.g., peptidases, kinases, phosphatases). MB1 specificity was reproducibly exhibited by 14/99 of the original yeast clones.

cDNA library plasmids were shuttled from the desired clones to E. coli [Guthrie et al, cited above] and the DNA sequence of the inserts was determined. All clones contained related or identical sequences of approximately 0.4 kb containing an open reading frame (ORF) of 135 amino acids encoding a Myc-interacting polypeptide, termed Bin1 [SEQ ID NO:2], which exhibited specificity for Myc.

B. Bacterial Expression of Murine Bin1 Polypeptide [SEQ ID NO:2] as a Soluble GST Fusion Protein To study the association of the 135 aa murine Bin1 polypeptide [SEQ ID NO:2] with Myc in vitro, the ~0.4 kb cDNA [SEQ ID NO:1] from one of the two hybrid clones, clone #99, was expressed as a glutathione-S-transferase (GST) fusion protein and used in binding assays with $^{35}$S-methionine-labeled in vitro translated (IVT) proteins. The binding experiments were configured essentially as described in A. K. Rustgi et al, Nature, 352:541–544 (1991).

To construct the GST fusion protein, the murine cDNA insert on a ClaI-EcoRI fragment was substituted for a similar fragment in pE47 [C. Murre et al, Cell, 56:777–783 (1989)], making pATG-99. The pATG-99 ORF included an initiator methionine, added a 15 amino acid N-terminal extension (3 amino acids from E47 and 12 amino acids from VP16) to the 135 residue clone #99 ORF, and retained the translational termination site derived from the two hybrid vector. Expression of the ATG99 polypeptide was confirmed by in vitro translation from pATG-99. The pATG-99 insert was then subcloned into pGEX-2T (Pharmacia) and the recombinant plasmid introduced into E. coli. GST-ATG99 polypeptide was expressed and purified from E. coli cell extracts on glutathione-Sepharose (Pharmacia), using protocols supplied by the vendor.

Twenty (20) μl (~0.5 μg) of purified GST-ATG99 protein was analyzed on an SDS-PA gel fixed and stained with Coomassie Blue. The apparent molecular weight (MW) of the Bin1 component of the fusion (22 kD) is larger than the predicted MW (14 kD) but is consistent with the apparent MW of in vitro translated murine Bin1 [SEQ ID NO: 2].

C. In Vitro Association of Myc and Bin1 [SEQ ID NO: 2]

[$^{35}$S]-methionine labeled c-Myc polypeptides were generated by IVT using TNT rabbit reticulocyte lysates (Promega). Expression plasmids included CMV Hm [G. C. Prendergast et al, Cell, 65:395–407 (1991)]; CMV Hm subclones containing MB1 deletion amino acids 49–101 [J. Stone et al, Mol. Cell. Biol., 7:1697–1709 (1987)]; MB2 deletion amino acids 120–140 [L. Li et al, EMBO J., 13:4070–4079 (1994)], or both deletions; the adenovirus E1A vectors p12S, p13S; and the SV40 large T antigen vector pTag [unpublished data]; and CMV-USF [L. Li, cited above].

Approximately 2.5 μg of GST or GST-ATG99 and 10 μl of an IVT reaction were added to 0.5 ml binding buffer (10 mM TrisCl pH 7.5, 5 mM EDTA, 500 mM NaCl, 0.25% NP40) incubated 1 hr at 4° C. on a nutator shaker, washed four times with binding buffer, and analyzed by SDS-PAGE and fluorography. c-Myc (but none of the other polypeptides produced by IVT) exhibited association with GST-ATG99.

D. Association of Bin1[SEQ ID NO:2] with TBP but not USF

[$^{35}$S]-labeled TBP and USF were generated by IVT and tested for GST-ATG99 binding as in C. above. Reinforcing the notion that it might be involved in MB1 function in transcriptional regulation by Myc, Bin1 bound to TATA-binding protein [TBP, a critical component of the basal transcription apparatus]. Other polypeptides that were tested for GST-ATG99 interaction and found to be negative included Max, cell cycle protein p107, transcription factor YY1, extracellular protein PAI-1, small GTP-binding protein RhoB, and empty-vector-associated products. Taken together, these findings argued that the association between GST-ATG99 and Myc was both specific and physiologically relevant, since it depended upon the presence of the Myc boxes.

EXAMPLE 2
Isolation of Human Bin1 cDNA

BLAST searches of the complete DNA sequence database [GenBank] with the murine Bin1 sequence showed no strong similarities to known genes, but revealed an approximately 89% identity to an 289 bp uncharacterized human "expressed sequence tag". This finding suggested that Bin1 represented a novel gene conserved and expressed in humans.

Northern analysis of RNA from several human tissues using a murine Bin1 cDNA [SEQ ID NO: 1] as probe revealed a single RNA species of ~2.2 kb that was abundant in skeletal tissue. A 1.95 kilobase human Bin1 cDNA was obtained from a human skeletal muscle λZAPII cDNA library (Stratagene, La Jolla, Calif.) by standard methods [Sambrook et al, cited above], using the murine Bin1 probe, i.e., by hybridization with [$^{32}$P]-labeled clone #99 insert and washing under low stringency conditions (2×SSC 42° C.). The complete sequence of this ~2.0 kb full-length cDNA, p99f, was determined [SEQ ID NO: 3] using the dideoxy method with Sequenase (US Biochemicals) and assembled and analyzed with MacVector software (IBI/Kodak). DNA database comparisons were performed using BLAST software. The subcloned cDNA contained a 451 amino acid ORF of predicted MW 50049 which included a nuclear localization signal (NLS)-like sequences, a Src homology 3 (SH3) domain, and a central region of approximately 89% identity to clone #99 which was implicated as the Myc-interacting region. The predicted gene product was termed Bin1 for Box-dependent Myc-Interacting protein-1 [SEQ ID NO:4].

Plasmid p99f was deposited with the American Type Culture Collection, 12301 Parklawn Drive, Rockville, Md. 20852 U.S.A. This deposit was made on Dec. 12, 1996 pursuant to the provisions of the Budapest Treaty, and bears the ATCC Designation 97823.

Comparisons of the Bin1 amino acid sequence to the DNA database were performed using the search algorithm BLAST [S.F. Altschul et al, *J. Mol. Biol.*, 215:403–410 (1990)]. Using the complete sequence to search the database, two known genes were identified which had highly significant similarity to the terminal regions of Bin1 (p<10$^{-8}$). The first gene was amphiphysin, a neuronal protein implicated in synaptic function which is the putative autoimmune antigen in breast cancer-associated Stiff-Man syndrome [F. Folli et al, *N. Eng. J. Med.*, 328:546–551 (1993)], a paraneoplastic disorder that clinically presents in a fraction of breast cancer patients. The meaning of this relationship was unclear but suggested connections of Bin1 to cancer. The second gene was RVS167, a negative regulator of the cell division cycle in *S. cerevisiae*. The region of the most extensive similarity between amphiphysin and RVS167, approximately 50% and 25%, respectively, lies within residues 1–222 of Bin1 [SEQ ID NO:4]. Therefore, this N-terminal region of Bin1 has been termed herein the BAR domain (for Bin1/amphiphysin/RVS167-related domain). These BAR-containing proteins all contained C-terminal SH3 domains that were separated from the BAR domains by sequences unique to each protein. The extensive similarity of the BAR domains in these proteins suggest a common molecular function. Moreover, the relationship suggests roles for Bin1 in breast malignancy, where Myc is frequently involved, and in cell cycle regulation. Finally, since RVS167 is a negative regulator which is dispensable for cell growth but required for cell cycle exit, the similarity to RVS167 would be consistent with the likelihood that Bin1 is a tumor suppressor, which is similarly dispensable for cell growth.

To gain additional insights into the molecular functions of Bin1, additional BLAST searches were performed with subsections of the Bin1 sequence. These searches identified several gene products which all function in regulation of cell cycle transit and/or chromosomal structure. Several additional relationships were revealed within the Bin1 BAR domain. These included pericentrin (30% identical; 46% similar; P<0.01), a centromere-binding protein required for proper chromosome organization during the cell cycle M phase; mitosin (24% identical; 48% similar; P=0.02), a protein implicated in transit through M phase; and SMC1 (21% identical; 43% similar; P=0.05), a yeast regulator of M phase chromosome segregation. In the scoring range where these similarities were observed, highly alpha helical regions of non-muscle myosin, tropomyosin, and the trp gene product were also found, suggesting that the BAR domain shares their highly helical structure. Between the C-terminal end of the BAR region and the nuclear localization signal (NLS; amino acids 252–265, SEQ ID NO: 4) lies an additional Bin1 domain termed U1 (amino acids 224–251, SEQ ID NO: 4), encoded by a single exon, which is not found in amphiphysin and RVS167 but which also contains motifs seen in proteins controlling cell cycle and chromosome structure. One ~10 amino acid motif is found in a functionally important region of the SV40 T antigen oncoprotein, while a second motif is seen in RED1, a yeast protein implicated in chromosome segregation. Proximal to these motifs is an additional motif which is similar to p93dis1, another yeast protein implicated in chromosome segregation. Taken together, these observations strengthen the likelihood that Bin1 participates in some aspect of cell cycle regulation and further suggests a role in chromosome structure control.

EXAMPLE 3
Human Bin1 Gene Isolation, Structure and Regulation

Genomic clones of human Bin1 have been obtained. Using the genomic clones, the human Bin1 gene has been mapped to chromosome 2q14. This region is within a mid-2q locus that has been reported to be deleted in approximately 42% of metastatic prostate carcinomas. The region of the murine genome syntenic to human 2q14 has also been reported to be deleted in >90% of radiation-induced leukemias and lymphomas. These data strengthen the previous assertion that Bin1 may be encoded by a novel tumor suppressor gene.

A. Increase in Bin1 Levels During Muscle and Neuronal Differentiation

Bin1 RNA has been found to be present in brain and muscle cells at 10- to 100-fold higher levels than other tissues, a feature shared with cell cycle kinase inhibitors (CKIs). Since these cells are postmitotic and Bin1 had been shown to block Myc's ability to induce cell cycle progression, it is possible that under certain circumstances, upregulation of Bin1 has a role in cell cycle exit associated with cell differentiation. To begin to assess this possibility, Bin1 expression was examined using in vitro model systems for differentiation of muscle cells (murine C2C12 premyoblast cells) [L. Silberstein et al, *Cell*, 46:1075–1081 (1986)] and neurons (rat PC12 pheochromocytoma cells) [L. A. Greene and A. S. Tischler, *Proc. Natl. Acad. Sci. USA*, 73:2424–2428 (1976)].

This analysis revealed that both Bin1 RNA and protein are regulated during cell differentiation. Bin1 RNA levels were increased following induction of cell differentiation in C2C12 or PC12 cells, by serum deprival or nerve growth factor (NGF) addition, respectively. In untreated PC12 cells, three transcripts of ~1.3, ~2.4, and ~2.9 kb were noted. Within 5 days of NGF treatment the level of the ~2.9 kb RNA was increased several-fold, concomitant with neurite extension, while the level of the other two RNAs decreased to undetectable levels. The nature of the ~1.2 kb transcript, which was most abundant in untreated cells, was unclear but its unusually small size suggested the possibility that it was truncated due to mutation (PC12 was derived from a rat adrenal gland tumor). In C2C12 cells, transcript(s) of ~2.4 kb increased ~20-fold within 5 days of serum deprival, concomitant with myotube formation. These observations suggest that Bin1 may be involved in cell cycle regulation during neuronal and muscle cell differentiation.

B. BIN1 Gene Structure and Exon-Intron Organization

Human BIN1 genomic clones were isolated from a WI-38 diploid λFIX fibroblast genomic DNA library using a BIN1 cDNA probe. Six phage inserts were subcloned in pBS+ [Stratagene] and subjected to DNA sequencing. The data were assembled manually with assistance from MacVector and AssemblIGN software. Sequence analysis and database comparisons were performed using the algorithms SIM and ClustalW (pairwise or multiple sequence alignments), TBLASTN (DNA database comparisons), MatInspector and TESS (promoter binding site identification). The Genbank accession number for BIN1 cDNA is U68485 and for BIN1 genomic sequences are U83999 through U84004. The genomic sequences are provided in FIGS. 3A–3N, and SEQ ID NOS: 7–12].

A physical map of the BIN1 gene was constructed by restriction mapping and Southern analysis of the six independent phage clones. Five overlapping clones constituting a ~38 kb contig were determined to contain exons 2–16. An additional noncontiguous clone (31.2) containing a ~16 kb insert was found to contain exon 1 and 5' flanking sequences, the latter extending ~3 kb upstream of the RNA cap site (see below). Based on the size of the cloned region, it was concluded that the size of the human BIN1 gene spanned at least 54 kb.

The exon organization of the gene correlated roughly with the domain organization of the BIN1 polypeptide. Exons 1 and 2 were separated from each other by a large first intron (≧17 kb) and from the rest of the gene by a second intron of ~5 kb. The remaining BIN1 exons were clustered in three groups (exons 3–6, 7–12, and 13–16) spanning several kilobases each. Exons 1–8 encoded the BAR (Bin1/Amphiphysin/Rvs 167-related) domain, a region named for the structural similarity shared between BIN1, the neuronal protein amphiphysin, and the yeast cell cycle regulator RVS167. Exons 9–11 encoded part of the central, evolutionarily unique region of BIN1, with unique-1 (U1) and unique-2 (U2) regions encoded by exons 9 and 11, respectively, and the putative nuclear localization signal encoded by exon 10. Exons 13–14 and 15–16 encoded the MYC binding domain (MBD) and Src homology 3 (SH3) domain of BIN1, respectively. In addition to coding regions exons 1 and 16 included 5' and 3' untranslated regions (5' and 3' UTRs) of 161 bp and 452 bp, respectively.

To define the exon-intron boundaries in BIN1, the DNA sequence of five genomic segments containing exon 1, exon 2, exons 3–6, 7–12, and 13–16 were determined. Boundaries for most exons were defined by comparison to the BIN1 cDNA [SEQ ID NO:3]. The sequence and boundaries of exon 12, which was not included in the original cDNA isolate, was determined from RT-PCR products derived from a set of human cell lines (see below).

In examining the 5' end of the BIN1 gene, a significant difference was noted between the genomic exon 1 sequence [nucleotides 2051 to 2294 of SEQ ID NO: 6] and the 5' end of the original BIN1 cDNA. The genomic sequence contained a different 5' UTR and translation initiation site and encoded the N-terminal coding amino acids MAEMGSKG [SEQ ID NO: 13], instead of MLWNV [amino acids 1–5 of SEQ ID NO: 4] as predicted by the cDNA. The genomic sequence was judged to accurately represent the 5' end of the BIN1 mRNA, because (i) expressed sequence tag (EST) sequences identical to the genomic but not the 5' cDNA sequence were identified; (ii) cDNAs whose structure matched the original cDNA clone could not be identified by RT-PCR; (iii) the genomic sequence was highly related to the 5' end of a murine BIN1 cDNA ([SH3P9, A. B. Sparks et al, *Nat. Biotech.*, 14:741–744 (1996); Genbank accession U60884); and (iv) the 5' end of the cDNA was found to contain an inversion of 64 bp derived from the middle of the cDNA (previously missed in part because the inversion fortuitously contained a translation initiation site).

Comparison of the 3' end of the BIN1 gene to the EST database revealed five additional potential coding sequences that were absent from the skeletal muscle-derived BIN1 cDNA. Each of these putative exons were located downstream of exon 11 and were initially identified by identities to ESTs (accession numbers R84732, R33418, R36301, H30787, R22654). One of these exons was designated exon 12 because its existence in BIN1 transcripts in several cell lines was subsequently validated by RT-PCR and DNA sequencing (see below). Exon 12 encodes a 42 residue segment with 64% similarity to aa 297–339 of human amphiphysin [R. Yamamoto et al., *Human Mol. Genet.*, 4:265–268 (1995)]. The other four putative exons in this region were identified tentatively, because canonical splice donor and acceptor sites at presumptive exon-intron junctions were absent in several cases, such that the full extent of each exon was unclear. In each case, the ESTs identifying these putative exons were isolated from brain cDNA libraries (date not shown), suggesting that they might represent tissue-specific exons spliced into BIN1 RNA only in brain. The first exon in this set was located immediately 3' of exon 11, representing read-through into intron 11 sequences. The remaining three exons were located within a region 3110 bp upstream of exon 13 and encoded residues similar to a central region of amphiphysin (data not shown). The fact that exon 12 and these sequences were present in some but not all ESTs suggested that they were subject to alternate splicing, possibly conferring amphiphysin-like structure and/or function to a subset of BIN1 polypeptides.

C. Alternate Splicing of BIN1 RNA

Patterns of BIN1 splicing were examined by RT-PCR analysis of cellular RNA. The substrate for RT-PCR was 2 μg of total cytoplasmic RNA isolated as described [G. C. Prendergast and M. D. Cole, *Mol. Cell. Biol.*, 9:124–134 (1989)] from human WI38 normal diploid fibroblasts, HeLa cervical carcinoma cells, or Rh30 rhabdomyosarcoma cells, each of which contain BIN1 RNA. The cells were cultured as described herein. Rh30 was included because the initial BIN1 cDNA was isolated from a skeletal muscle library and rhabdomyosarcoma is derived from a muscle cell tumor. RNA and 50 pmol oligo-dT (Pharmacia) were added to diethylpyrocarbonate (DEPC)-treated water (final volume 11 μl), heated 4 min at 70° C., and quenched on ice. The RT reaction (20 μl) was prepared by mixing 4 μl 5× buffer (250 mM TrisHCl) pH 8.3/375 mM KCl/15 mM MgCl$_2$), 1 μl 25 mM dNTPs, 2 μl 0.1 M dithiothreotal (DTT), 1 U RNAse inhibitor, and 100 U Moloney murine Leukemia Virus (MOMLV)RT (GibcoBRL). The reaction was incubated 1 hr at 42° C., heated to 94° C. for 5 min, and diluted to 100 μl with DEPC-treated water. Ten microliters of the diluted reaction was used as substrate for 30 cycles of PCR (50 μl) with 0.5 U Taq polymerase (Pharmacia) in 1× buffer/0.2 mM dNTPs/1.5 mM MgCl$_2$. The PCR cycle was 45 sec 94° C./45 sec 55° C./1 min 72° C. Separate PCR reactions were performed to generate 5' (N-terminus; exons 3–7), midsection (exons 6–11), and 3' (C-terminus; exons 11–15) segments of the BIN1 coding region. The 5' and 3' primer pairs for each product were as follows. For the 5' (N-terminus) product, AAGGATCTCCGGACCTACCT (cT7/ext; nt 168 to 187 of SEQ ID NO: 3) and CACATTCATCTCCTCAAA-CACC (ptx7α, nt 620 to 599 of SEQ ID NO: 3); for the midsection product, TGAAGCCAAAATTGCCAAGGC (dT3/ext, nt 551 to 571 of SEQ ID NO: 3) and TGGCT-GAGATGGGGACTTG (5'ATG99, nt 1007 to 989 of SEQ ID NO: 3); and for the 3' (C-terminus) product, GGAGAAT-TCGCGATGCCTGCAAAAGGGAACAAGAGC (99Fsp, nt 870 to 890 of SEQ ID NO: 3) and GGACTCGAGT-CATGGGACCCTCTCAGTGAAGTTC (99SH3anti, which corresponds to nt 1415 to 1391 of SEQ ID NO: 3, with a linker of GGACTCGAG at the 5' end). Products were fractionated on agarose gels, blotted, and hybridized, or isolated and subcloned for DNA sequencing.

Amplification of exons 3–7 yielded a single product that did not vary among the cell lines examined, suggesting that the 5' region of BIN1 is not subject to alternate splicing. In contrast, RT-PCR products derived from the central and 3' regions of BIN1 provided evidence of several alternative splicing events. In the central region (exons 7–11), two major products were observed. Subcloning and sequencing of these products revealed that they differed in a segment of 45 nucleotides identical to exon 10 (encoding a putative nuclear localization signal). In normal WI-38 cells, messages including and lacking exon 10 were equally abundant. In contrast, in Rh30 and HeLa tumor cells, messages lacking exon 10 predominated. Amplification of the 3' end of BIN1 revealed a more complex pattern of splicing. Subcloning and sequencing of the various bands obtained revealed several that included one of the putative exons initially identified by EST database comparisons. This exon, although absent from the original BIN1 cDNA, was therefore designated exon 12. None of the other putative EST-defined exons were found in the RT-PCR products examined. However, in addition to exon 12, the MBD-encoding exon 13 was also found to be differentially represented among the 3' amplification products. In normal WI-38 cells, most messages included exons 12 and 13, whereas in Rh30 and HeLa tumor cells, there was a comparatively equal distribution in the expression of messages including or lacking these exons.

To determine which combinations of exons 10, 12, and 13 were alternately spliced in the cells examined, RT-PCR was performed using primers specific for sequences in exon 9 and 16. Subcloning and DNA sequencing of these products revealed that exon 12 was only spliced in when either exon 10 and/or 13 were present. Thus, inclusion of exon 12 was contingent on either or both exons 10 or 13. It was concluded that exons 10, 12, and 13 were alternately spliced and that exon 12 splicing was determined by the splicing of exons 10 or 13.

D. Definition of 5' Flanking Sequences Sufficient for Basal Transcription and MyoD Activation Definition of the BIN1 promoter was of interest for two reasons. First, as shown herein, the inventors' work suggested that epigenetic mechanisms might underlie the loss of BIN1 expression in breast tumor cells. Therefore, characterization of the BIN1 promoter would permit an examination of tumor DNA for alterations in DNA methylation or transcription factor interactions which might account for loss of expression. Second, BIN1 has been expressed at high levels in skeletal muscle and murine C2C12 myoblasts. For this reason, it was predicted that the BIN1 promoter might be activated by MyoD, a master regulator of muscle cell differentiation [S. J. Tapscott et al, Science, 242:405–411 (1988)].

In order to identify the BIN1 promoter, it was first necessary to pinpoint the site(s) of transcription initiation. To this end, primer extension analysis was performed on RNA from WI-38 diploid fibroblasts as follows. By comparing the genomic sequence to that of a murine BIN1 cDNA [Sparks et al, cited above], which has a long 5' UTR, a primer that was likely to hybridize within 100 nt of the RNA cap site was chosen. Three pmol of the oligonucleotide primer ACAGCGGAGCCAACTGAC (PEprimer #2; antisense sequence of nucleotides 2083 to 2066 of SEQ ID NO: 6) end-labeled with $\lambda^{32}$P-ATP was annealed to 10 μg of WI-38 total cytoplasmic RNA for 12 hr at 58° C. in hybridization buffer (40 mM PIPES pH 6.4, 1 mM EDTA, 0.4 M NaCl, 80% formamide). The annealed RNA was ethanol precipitated and resuspended in 20 μl RT reaction buffer (see above) plus 50 μg/ml actinomycin D (BMB). The reaction mixture was incubated 1 hr at 42° C. and stopped by the addition of sequencing gel loading buffer. A standard $\alpha^{35}$S-dATP DNA sequencing reaction was performed with the same primer using clone p31.2 as the template. The primer extension and sequencing products were cofractionated on a 12% DNA sequencing gel and autoradiographed for 15 min (extension reaction) or overnight (sequencing reaction).

RT-mediated primer extension yielded a 33 nt product. Together with the DNA sequence of the 5' flanking region generated by this primer, the 5' end of BIN1 RNA in WI-38 cells was mapped to the guanine residue designated +1 [nt 2051 of SEQ ID NO: 7].

Determination of the genomic sequence upstream of the RNA cap site indicated that the 5' flanking region was GC-rich and lacked a TATA box but contained a consensus binding site for TATA-binding protein (TBP) at −79 [nt 1972 of SEQ ID NO: 7]. Supporting the possibility that MyoD may regulate BIN1, a consensus recognition site for MyoD (GCACCTGG) was located at −238 [nt 1814 of SEQ ID NO: 7]. Consistent with a possible promoter function, computer search algorithms identified consensus sites for several other transcription factors in this region (data not shown). Finally, within 700 nucleotides immediately upstream of exon 1, ~18% of the sequence was composed of CpG dinucleotides, indicating the presence of a CpG inland typical of many TATA-less housekeeping gene promoters. These observations suggested that the 5' end of the BIN1 gene cloned might contain a functional promoter.

The transcriptional potential of the 5' flanking region was tested in a transient transfection assay.

An 886 bp Bgl II restriction fragment including proximal 5' flanking sequences from p31.2 was cloned into the luciferase reporter plasmid pGL2-Basic (Promega), allowing transcription to be initiated at the BIN1 cap site. The resulting plasmid is termed pGL-Bgl. The hosts for transfection, C2C12 cells (which express high levels of endogenous Bin1 RNA) or $10T_{1/2}$ cells (which do not express MyoD but in response to it differentiate into myoblasts), were cultured in DMEM containing 15% fetal calf serum and penicillin/streptomycin. Cells ($4\times10^4$ per 60 mm dish) were transfected [C. Chen and H. Okayama, *Mol. Cell. Biol.*, 7:124–134 (1989)] with 5 μg pGL2-Bgl or pGL2-basic, 4.5 μg pSK+ (Invitrogen), and 0.5 μg CMV-βgal. For MyoD activation, a murine MyoD expression construct under control of the βactin promoter was substituted for pSK+. Cells were harvested and processed for luciferase activity two days post-transfection using a commercial kit (Promega).

Within two days after transfection, pGL2-Bgl exhibited ~100-fold greater activity than the control plasmid pGL2-Basic in C2C12 cells.

To determine whether pGL2-Bgl included sequences that were sufficient for regulated expression, the plasmid was introduced with or without a MyoD expression vector into $10T_{1/2}$ fibroblasts. As a positive control for MyoD responsiveness, a second set of transfections used a luciferase reporter driven by a mutated ornithine carboxylase promoter (ODCΔSmut-luc) containing a MyoD E box response element (J. Cleveland, unpublished results). The activity of both reporters was observed to be increased up to ~7-fold the basal level by MyoD cotransfection. The effect was dose-dependent because higher ratios of MyoD; reporter plasmids increased reporter activity. From this it was concluded that the 5' flanking sequences of the BIN1 gene constituted a promoter sufficient for directing transcription in muscle cells.

E. Analysis of Results

As discussed herein, exon 1 sequences derived from genomic DNA reflected the actual 5' end of the BIN1 RNA; the sequence of the 5' end of the original cDNA appeared to be artifactual, although the remote possibility that some transcripts in muscle may contain the originally cloned structure can not be ruled out. Addition putative exons were identified by comparison of genomic sequences to the EST database. One of these, exon 12, was validated by subsequent RT-PCR and DNA sequencing analyses of RNA in each of several cell lines examined. Four other putative exons identified by EST similarities have not yet been validated by RT-PCR. If they do represent true coding regions, these exons may be brain-specific, since the ESTs which identified them were derived exclusively from brain cDNA libraries. Consistent with this possibility, murine brain has been observed to contains a large RNA species that hybridizes with a BIN1 probe, in addition to the smaller ubiquitous species seen in other tissues.

Exons 10, 12, and 13 of BIN1 were subject to alternative splicing, resulting in the generation of seven different RNA species. Exons 10 and 13 encodes sequences implicated in BIN 1 localization and MYC interaction, suggesting splice regulation of these functions. Exon 12 encodes amphiphysin-related sequences that are functionally undefined. Amphiphysin is a BIN1-related neuronal protein implicated in synaptic vesicle endocytosis [C. David et al, *Proc. Natl. Acad. Sci. USA*, 93:331–335 (1996)]. The consequences of exon 12 splicing are unknown because the functional relationship between BIN1 and amphiphysin is currently unclear. However, the appearance of exon 12 in BIN1 RNA was contingent on exon 10 or 13. Therefore, exon 12 sequences may influence the cell localization or MYC binding properties of BIN1.

Interestingly, differences in the level of various splice forms of BIN1 were observed between cell types. In normal WI-38 cells, messages were equally likely to lack or include exon 10 (encoding a putative nuclear localization signal), whereas in Rh30 and HeLa tumor cells, most messages were exon 10 deficient. Moreover, while most WI-38 transcripts contained exons 12 and 13, many transcripts from Rh30 and HeLa did not. Considering the functions of each exon, the results implied that normal WI38 fibroblasts may express relatively higher levels of nuclear localized BIN1 polypeptides with MYC-binding potential and central amphiphysin-like character, relative to the tumor cells examined. Whether these differences represent cell type variations or differences between normal and tumor cell types is unclear, but it is possible that altered splice patterns may be germane to tumorigenesis.

Definition of exons and exon-intron boundaries will facilitate tests for structural mutations. In particular, the identification of alternately spliced RNAs raises the possibility that splice donor or acceptor site mutations may be germane to tumorigenesis. Finally, promoter definition will allow assessment of the importance of epigenetic mechanisms as a basis for loss of BIN1 expression in breast carcinoma. One mechanism of interest would be an alteration in CpG methylation status, which forms the basis for loss of p16INK4 expression in lung cancers [A. Merlo et al, *Nat. Med.*, 1:686–692 (1995)]. The high density of CpG dinucleotides in the BIN1 promoter could make it acutely sensitive to changes in methylation status. Alternately, it is also possible that changes in the DNA binding or activity of transcription factors which regulate BIN1 could account for expression differences. In any case, promoter definition will assist studies aimed at determining the basis for the frequent loss of BIN1 expression in carcinoma cells.

EXAMPLE 4

Construction of Mammalian Expression Vectors and Immunoprecipitation Techniques

Viral vectors for delivering Bin1 into insect, rodent and human cells have been developed for various purposes, including therapeutic purposes and to permit high-level Bin1 protein production and efficient gene transfer.

A. Baculoviral Vector

~1.6 kb EcoRI fragment containing the complete Bin1 coding region was inserted into the baculovirus recombination vector pVL1393 (Invitrogen, Inc., San Diego, Calif.), generating pBacBin. Sf9 insect cells were cotransfected with pBacBin and a plasmid encoding a defective baculovirus which cannot propagate. Rare recombination between these two plasmids in vivo leads to generation of a lytic recombinant baculovirus which can be propagated. Virus produced in cultures of cotransfected cells was propagated in mass Sf9 culture. Bin1 production was verified by Western analysis of NP40 lysates prepared 24 and 48 hr after infection of Sf9 cells infected with the BacBin virus, using 99D monoclonal antibody.

It has been noted that, consistent with a therapeutic application where cell death induction is desirable (e.g., cancer), the BacBin virus killed Sf9 cells more rapidly than control viruses. The killing by BacBin was virtually complete by 48 hours post-infection and was refractory to coexpression of Bcl2, a death-suppressing gene frequently overexpressed in human cancer cells.

B. Adenoviral vector

The strategy and plasmid vector systems to produce recombinant adenovirus has been described [K. Kozarsky et al, *Curr. Opin. Genet. Dev.*, 3:499–503 (1993)]. Similar to the approach taken to make baculoviral vectors, two plasmids are used which contain complementary regions which can homologously recombine in vivo. Recombinant virus is produced only in transfected cells where recombination has taken place. The plasmid pAdCMVpAT153 is used to introduce the gene of interest. pAdCMVpAT153 contains the left 6% of the adenovirus serotype 5 genome, modified such that the E1 region is replaced with a cytomegalovirus (CMV) early region enhancer/promoter, multiple cloning site, and a G418 resistance gene cassette. Included in the cell transfection with this vector is a ~34 kb ClaI-digested fragment of adenovirus type 5 DNA that includes the remainder of the adenoviral genome. This fragment contains a mutation in the E3 region which ablates the immune response in adenovirus-infected animals [T. Ranheim et al, *J. Virol.*, 67:2159–2167 (1993)]. This feature was incorporated into the recombinant virus to increase the persistence and therefore the potential efficacy of Bin1-based gene therapy approaches. The cell host for transfection is human 293 cells, an epithelial line which expresses the E1 region gene products required for propagation of recombinant adenoviruses.

The plasmid pAdenoBin was generated by inserting a ~1.6 kb EcoRI fragment containing the complete Bin1 coding region into the multiple cloning site of pAdCMV-pAT153. 293 cells cotransfected with pAdenoBin and the ClaI-digeswer adenoviral DNA fragment were subjected to G418 selection and screening and purification by plaque assay (recombinant viruses are lytic in 293 cells). DNA isolated from a Bin1 virus identified in this manner will be validated by Southern analysis to confirm that the Bin1 cDNA is intact. These vectors are particularly well suited for use in human therapies.

C. Moloney Retroviral Vector

A recombinant Bin1 retrovirus was generated using methods that have been described [N. Landau et al, *J. Virol.*, 66:5110–5113 (1992)]. The Bin1 plasmid vector pSRαMSV-Bin1 was generated by inserting the ~1.6 kb EcoRI fragment containing the complete Bin1 coding region into pSRαMSV, a retroviral vector that lacks RNA packaging signals and includes a G418 resistance gene cassette. Briefly, recombinant virus was isolated from the media of COS monkey cells cotransfected with pSRαMSV-Bin1 and pSVψ-E-MLV, a proviral vector which provides the necessary retroviral packaging components. Recombinant virus was used to infect Rat1 fibroblasts and infected cell populations were selected by G418 selection. Expression of recombinant Bin1 in the Rat1 cell populations was confirmed by Northern and Western analysis.

Although the procedure above generated ecotropic Bin1 retroviruses limited to gene transfer to murine cells, those with skill in the art can easily generate amphotropic retroviruses that can transfer Bin1 to human cells. This is achieved by simply cotransfecting COS cells with pSRαMSV-Bin1 and pSVψ-A-MLV, a packaging vector which encodes an amphotropic instead of ecotropic envelope glycoprotein [N. Landau et al, cited above]. An additional method is to transfect BING cells, an amphotropic human packaging cell line [W. Pear, G. Nolan, D. Baltimore, unpublished], with the Bin1 retroviral vector. Such vectors may be applied for use in gene therapies to attack human cancers.

D. Mammalian Expression Vectors

Bin1 mammalian cell expression vectors were constructed as follows and were used to generate the Bin1 proteins used in the following experiments. CMV-Bin1 was generated by subcloning a 1.6 kb EcoRI fragment from the full-length human Bin1 cDNA clone, p99f, that contained the entire predicted Bin1 coding sequence into pcDNA3 (Invitrogen), a mammalian cell expression vector that contains a cytomegalovirus enhancer/promoter and a 3' poly-adenylation signal. CMV-HA-Bin1 was constructed by substituting a PvuII-EcoRI coding region fragment from CMV-Bin1 for an EcoRV-EcoRI fragment of neoCMV-hem rhoA, a RhoA expression plasmid that included an 8 residue N-terminal viral hemagglutinin (HA) epitope recognized by the monoclonal antibody 12CA5 [H. Niman et al, *Proc. Natl. Acad. Sci. USA*, 80:4949–4953 (1983)]. The HA-Bin1 polypeptide created included residues 1–47 from the N-terminus of RhoA [Yeramian et al, *Nucl. Acids Res.*, 15:1869 (1987)] and residues 52–451 of Bin1 [SEQ ID NO: 4]. This protein fusion added an N-terminal extension to Bin1 that allowed immunoprecipitation by anti-HA antibody 12CA5 [H. Niman et al, cited above]. CMV-Bin1ΔMBD deleted amino acid residues 270–377 [of SEQ ID NO: 4] in CMV-Bin1. It was constructed by ligating two separate PCR fragments generated by the 5' primer CCGGATCCGCGAT-GCTCTGGAACGTGGTGACG [nucleotides 60–80 of SEQ ID NO: 3] and the 3' primer GCGAATTCGTTGTCACT-GTTCTTCTTTCTGCG (fragment encoding aa 1–269) [nucleotides 866–842, corresponding to the antisense strand of SEQ ID NO: 3] and the 5' primer CGGAATTCAC-CATGGGTTTCATGTTCAAGGTACAG [nucleotides 1191–1211 of SEQ ID NO: 3] and the 3' primer CCGCTC-GAGTCATGGGACCCTCTCAGTGAAGTT (fragment encoding aa 378–451) [nucleotides 1415–1392, corresponding to the antisense strand of SEQ ID NO: 3]. This construction added the nonspecific amino acids EFTM at the fusion junction due to the restriction site added.

E. ImmunoPrecipitation

Two Bin1 antibodies were used in this study. A polyclonal antisera used was generated by immunizing rabbits with a GST fusion protein containing amino acid residues 189–398 of Bin1 (GST-ATG99Pst) [SEQ ID NO: 4], that included all of the MBD, using a commercial service (Rockland, Inc., Boyerstown, Pa.). A Bin1-specific monoclonal antibody, 99D, was raised to the same immunogen as used for the polyclonal antiserum and is specific for the ~70 kD Bin1 polypeptide.

COS, MCF7, and IMR90 cells were cultured in Dulbecco's modified Eagle's media (DMEM) supplemented with 10% fetal bovine serum (Sigma) and 50 U/ml each penicillin and streptomycin (Fisher). Cells were transfected by a modified calcium phosphate protocol [C. Chen et al, *Mol. Cell. Biol.*, 7:2745–2752 (1987)] and metabolically labeled 48 hr later.

Ten microliters of crude antisera or prebleed sera was used for immunoprecipitations from IMR90 or transiently transfected COS cells metabolically labeled 2–4 hr in DMEM media lacking methionine and cysteine (Gibco) with 75–125 $\mu$Ci/ml EXPRESS labeling reagent (NEN), washed with ice-cold phosphate-buffered saline, and extracted for 20 min on ice with RIPA buffer containing the protease inhibitors leupeptin, aprotinin, phenylmethylsulfonyl fluoride, and antipain [E. Harlow et al, Antibodies: A Laboratory Manual, Cold Spring Harbor Laboratory Press, Cold Spring Harbor, N.Y. (1988)]. Before the addition of Bin1 antibodies, extracts were precleared by centrifugation at 20,000 g for 15 min at 4° C. followed by 1 hr treatment with prebleed sera and 20 $\mu$l of a 1:1 slurry of protein G Sepharose beads at 4° C. on a nutator (Pharmacia). Precleared lysates were immunoprecipitated 90 min at 4° C. and then additional protein G beads were added and the incubation an additional 30 min. Beads were collected by brief centrifugation, washed four times with RIPA buffer, boiled in SDS gel loading buffer, fractionated on 10% gels, and fluorographed.

To establish that the Bin1 cDNA encoded a polypeptide similar to that found in normal cells, metabolically labeled extracts from IMR90 normal human diploid fibroblasts were subjected to immunoprecipitation. The results are described in Example 5 below.

EXAMPLE 5
Characterization of Bin1

A polyclonal antiserum was raised to a bacterially-expressed polypeptide derived from the unique central region of Bin1, in order to reduce the chance of crossreaction with Bin1-related proteins. When incubated with metabolically labeled extracts from COS cells transfected with CMV-Bin1, this antisera immunoprecipitated two polypeptides with apparent MW 70 kD and 45 kD. All polypeptides were specifically recognized because their immunoprecipitation could be blocked by preincubating antisera with a molar excess of GST-Bin1 immunogen but not with unfused GST. In COS cells transfected with CMV-HA-Bin1, only the 70 kD polypeptide was immunoprecipitated by an anti-HA monoclonal antibody. The IVT product from the full-length cDNA also had an apparent mobility of 70 kD. These data indicated that the 70 kD species was Bin1 and suggested that the 45 kD species was a Bin1-related polypeptide. Cells transfected with CMV-Bin1ΔMBD, a Bin1 deletion construct lacking the central Myc-binding domain (amino acid 270–377 of SEQ ID NO: 4), exhibited stable accumulation of a polypeptide whose predicted and apparent MW were both 42 kD. This result indicated that full-length Bin1 migrated aberrantly due to an MBD determinant at 70 kD in SDS polyacrylamide gels, instead of at the predicted MW of 50 kD. Only the 45 kD polypeptide was detected in untransfected MCF7 breast tumor cells, which lacked Bin1 RNA, or in cells transfected with empty vector. Thus, the 45 kD species was not a coprecipitant or an alternately processed or degraded form of Bin1. Consistent with its assignment as a Bin1-related protein, the 45 kD polypeptide could be detected by Western blotting.

EXAMPLE 6
Immunofluorescence Studies

~5×10$^3$ HepG2 cells were seeded onto glass cover slips in 6 cm dishes and the next day transfected overnight with 4 μg CMV-Bin1 or pcDNA3. Two days later cells were washed and processed for immunofluorescence essentially as described [G. Prendergast et al, *EMBO J.*, 10:757–766 (1991)], using 5 pg of protein A Sepharose-purified anti-Bin1 IgG and a 1:1000 dilution of fluorescein-conjugated anti-rabbit IgG (Cappel) as the secondary antibody. Stained cover slips were examined and analyzed on a Leitz confocal microscope.

In this manner, cell localization was examined by indirect cell immunofluorescence of transiently transfected cultures of HepG2 hepatocarcinoma cells, which like MCF7 cells lack detectable Bin1 RNA (see below) and therefore provided an internal control for any crossreacting polypeptides. HepG2 cells transfected with CMV-Bin1 but not vector exhibited a speckled nuclear pattern of staining. This pattern of localization has been confirmed using the 99D monoclonal antibody in untransfected cells that express Bin1. The nuclear localization was consistent with the presence of a NLS in the primary sequence of Bin1 and with a nuclear site of interaction with Myc.

EXAMPLE 7
Inhibition of Myc Oncogenic Activity by Bin1

As described herein, the ability of Bin1 to associate with Myc depended on the presence of MB1 and MB2, which are required for transformation activity [J. Stone et al, *Mol. Cell. Biol.*, 7:1697–1709 (1987); L. Li et al, *EMBO J.*, 13:4070–4079 (1994); and B. Pulverer et al, *Oncogene*, 9:59–70 (1994)]. The effects of Bin1 and the MBD deletion mutant Bin1ΔMBD (Example 4) on cell transformation were tested in the Ras cooperation assay [H. Land et al, *Nature*, 304:596–602 (1983)] performed in primary rat embryo fibroblasts (REFs; Whittaker Bioproducts). For specificity controls, additional experiments were performed in which Myc was replaced by either adenovirus E1A or SV40 T antigen, which can also cooperate with Ras in this assay. Since the original clone #99 cDNA was partial and encoded essentially only the MBD, it was anticipated that the clone #99 ORF might act in a dominant negative manner to interfere with either endogenous Bin1. Therefore, the effects of a clone #99 expression vector (Example 4) on Myc transformation were also tested.

The ~0.5 kb murine cDNA [SEQ ID NO: 1] engineered with a 5' Kozak initiator methionine from pATG-99 was subcloned into pcDNA3 (a CMV enhancer/promoter vaccine; Invitrogen, San Diego, Calif.) to generate neoCMV-ATG99. REF culture and transfection was performed essentially as described [G. Prendergast et al, *Genes Dev.*, 6:2429–2439 (1992)]. Briefly, secondary passage REFs seeded into 10 cm dishes were transfected overnight by a calcium phosphate coprecipitation method [C. Chen et al, cited above] with 5 μg each of the oncogene plasmids and 10 μg of other plasmids indicated, then passaged 1:5 the next day and fed with normal growth media until foci were scored by methanol fixation and crystal violet staining 12–14 days later. In some experiments, 0.5 mg/ml G418 was added the day after passaging. The following oncogene plasmids were used in REF assays. LTR Hm, which contains a Moloney long terminal repeat-driven normal human c-myc gene, and pT22, which contains an activated H-ras gene, have been described [H. Land et al, cited above and A. Kelekar et al, *Mol. Cell. Biol.*, 6:7–14 (1986)]. A nontransforming Myc frameshift mutant (MycFS) was constructed by digestion of LTR Hm with a unique Bst EII in exon 2 of the human c-myc gene, filling with Klenow enzyme, and self ligation. The MycFS polypeptide encoded by this mutant, LTR Hm/Bst, is frameshifted at amino acid residue 104, eliminating its biological function. This frameshift mutant was included to establish that the augmentation of foci formation by CMV-ATG99 was Myc-dependent. In some control experiments, NeoCMV T and p1A/neo, encoding SV40 T antigen and adenovirus E1A, respectively, were substituted for LTR Hm. Transformed foci were scored two weeks later.

Figure 4B:
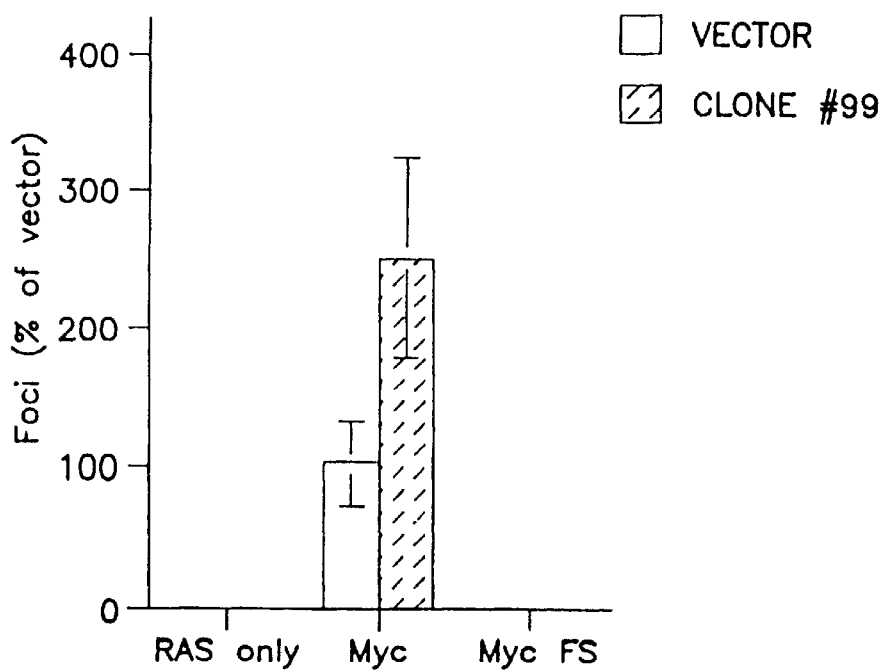
FIG. 4B is a bar chart illustrating the dominant inhibitory activity of MBD.

The results of the REF focus formation experiments are shown in FIG. 4. On its own or with activated RAS, Bin1 lacked transforming activity. However, when cotransfected at a 2:1:1 ratio with MYC and RAS, Bin1 selectively inhibited focus formation ~7-fold. Inhibition could be titered by decreasing the ratio of Bin1 to MYC and RAS vectors in the transfected DNA (data not shown). Moreover, inhibition was dependent on Myc binding, since Bin1 ΔMBD, which lacks the Myc-binding domain, was inactive in this assay. The loss of inhibition could not be attributed to protein instability, because Bin1ΔMBD had been shown to stably accumulate in transfected COS cells, and could inhibit E1A transformation. Thus, deletion of the Bin1 MBD relieved BIN1 inhibition of MYC transformation. BIN1 also inhibited E1A-dependent transformation, consistent with the fact that E1A and Myc function similarly in biological assays [G. Evan et al, *Cell*, 69:119–128 (1992); H. Land et al, cited above; H. Ruley, *Nature*, 304:602–606 (1983); and L. Rao et al, *Proc. Natl. Acad. Sci. USA*, 89:7742–7746 (1992)]. However, Bin1 did not affect T antigen-dependent transformation. This result indicated that the inhibition of Myc and E1A was not due to toxicity or nonspecific inhibition of the transformed phenotype. Notably, Bin1ΔMBD significantly inhibited E1A but not Myc. Although the means by which Bin1 and Bin1ΔMBD inhibited E1A was unclear, an important implication of this result was that Bin1 inhibited E1A and Myc by different mechanisms. Supporting the notion that Bin1 was incompatible with Myc or E1A transformation, exogenous Bin1 message accumulated in REF cell populations derived from transformation with T antigen but not with Myc or E1A; in contrast, Bin1ΔMBD message accumulated in REFs transformed by Myc. There is a possibility that a reduced activity of Bin1ΔMBD revealed intrinsic differences in the sensitivity of E1A and Myc to Bin1 inhibition. However, with this caveat, it was concluded that Bin1 physiologically interacted with and inhibited Myc, since deletion of a Bin1 domain sufficient for association in vitro was necessary for its inhibition activity in vivo.

In contrast to the effect of full-length Bin1, but consistent with a dominant inhibitory effect, the murine vector neoCMV-ATG99 specifically augmented focus formation ~2.4-fold when cotransfected with myc and ras. confirming a dominant inhibitory effect, titration of clone #99 into the REF assay was observed to reverse inhibition of Myc and Ras by Bin1 (data not shown). When taken together with the in vitro biochemical association results, the REF transformation data provided genetic evidence that Bin1 and Myc could interact in vivo. First, mutation in Bin1 eliminated Bin1 inhibition. Second, a portion of Bin1 encompassing the MBD alone (clone #99) increased Myc transforming activity through a dominant inhibitory activity. Finally, since the MBD was sufficient and the Myc boxes were necessary for association in vitro, there was good correlation between the regions involved in protein-protein association and the regions required for biological action. It was therefore concluded that Bin1 inhibited Myc by directly interacting with it in vivo.

EXAMPLE 8
BIN1 Inhibits Transactivation of Ornithine Decarboxylase by MYC in an MBD-Dependent Manner As shown in Example 7, BIN1 interacts with MYC and inhibited its oncogenic activity. The interaction requires the presence of Myc boxes 1 and 2, two N-terminal segments which are critical for biological functions of MYC [M. Henriksson and B. Luscher, *Adv. Canc. Res.*, 68:109–182 (1996); G. C. Prendergast, "Myc function", in *Oncogenes as Transcriptional Regulators*, Birkhauser Verlag, Boston (1997)]. Because the Myc boxes are part of the putative transactivation domain (TAD) of MYC [G. J. Kato et al, *Mol. Cell. Biol.*, 10:5914–5920 (1990)], the ability of BIN1 to influence the ability of MYC to transactivate ornithine carboxylase (ODC), a well-characterized physiological target gene that has been implicated in cell transformation, tumorigenesis, and apoptosis was investigated, as described in this example.

The ODC reporter gene used, ODCΔLuc, includes the 5' end of the murine ODC gene containing 5' flanking sequences, exon 1, intron 1, and exon 2; two E box sites recognized by the physiological MYC/MAX oligomer and required for MYC transactivation lie in intron 1 [C. Bello-Fernandez et al, *Proc. Natl. Acad. Sci. USA*, 90:7804–7808 (1993)]. NIH3T3 cells were used as a host for transient transfection of ODCΔLuc, a c-MYC expression vector, and expression vectors for BIN1, a BIN1 mutant lacking the MYC-binding domain (BIN1ΔMBD), or empty vector. As a positive control for suppression, trials including the retinoblastoma (Rb)-related protein p107 (instead of BIN1), which has been reported to interact with the MYC TAD and inhibit its activity [R. L. Beijersbergen et al, *EMBO J.*, 13:4080–4086 (1994); W. Gu et al, *Science*, 264:251–254 (1994)] were added. Cells seeded into 6 well dishes were transfected in duplicate wells as described above with 1.5 μg ODCΔS-luc, 3 μg LTR-Hm, 1.5 μg vectors indicated above, and 0.5 μg CMV-βgal (to normalized for transfection efficiency). pcDNA3 was added to bring the total DNA per each 2 well transfection to 6.5 μg DNA. Two days post-transfection, cells were harvested and cell lysates were prepared and assayed for luciferase activity.

MYC was observed to increase ODC-dependent luciferase activity 2- to 3-fold. BIN1 and p107 each reversed this effect. The BIN1 inhibition was relieved by deletion of the MBD, which is sufficient to bind MYC and is necessary to inhibit MYC transformation. To rule out that BIN1's inhibitory activity was cell type-dependent, the effects of BIN1 and BIN1ΔMBD were compared in HeLa and NIH3T3 cells. HeLa cells were seeded as described above. A similar MBD-dependent inhibition was observed in each cell type. The inability of BIN1ΔMBD to suppress MYC activity in these experiments was not due to polypeptide instability nor to general loss of function, because BIN1ΔMBD accumulated similarly to wild-type BIN1 in transfected COS cells and was capable of inhibiting E1A transformation (see below). It was concluded that BIN1 inhibited the E box-dependent transactivating activity of MYC in an MBD-dependent manner.

EXAMPLE 9
BIN1 Recruits a Repression Activity that is Sensitive to Target Gene Context The following studies were performed to determine whether BIN1 could inhibit MYC TAD activity outside of a target gene context, similar to p107 [A. T. Hoang et al, *Mol. Cell. Biol.*, 15:4031–4042 (1995); B. Smith-Sorensen et al, *J. Biol. Chem.*, 271:5513–5518 (1996)], and to distinguish between the possibilities that BIN1 acted passively, by occluding coactivators, or actively, by delivering a repression function (either intrinsic to BIN1 or mediated by BIN1 interaction).

To address the first issue, whether BIN1 could inhibit the transcriptional activity of a GAL4 chimera, GAL4-MYC (1–262) [G. J. Kato et al, cited above], which includes all of MYC except for the b/HLH/LZ domain which mediates oligomerization with MAX and physiological DNA binding, was tested. To address the second issue, GAL4-BIN1 chimeric DNA binding molecules that could deliver BIN1 to DNA in a MYC-independent fashion were generated, to see if BIN1 had a repressive quality on its own.

HeLa cells were seeded as described in Example 8 above and transfected with 2 μg Gal$_5$SV40-luc reporter, 4 μg of the indicated chimeric gene, and 1 μg CMV-βgal. In the first case, the chimeric vector is an expression vector for GAL4-MYC(1–262), whereas in the second case, it is GAL4-BIN1 or a GAL4-BIN1 deletion mutant. Two days post-transfection, cell extracts were prepared and analyzed for luciferase and βgalactosidase activity using a commercial kit (Promega), following the protocol provided by the vendor.

In these cells, the activity of GAL4-MYC (1–262) was 2.3-fold greater than unfused GAL0 (which expresses the DNA binding domain of GAL4 (aa 1–143)). Notably, BIN1 did not inhibit the activity of GAL4-MYC(1–262), but instead actually augmented it approximately 60% (data not shown). This result indicated that BIN1 inhibition of MYC TAD activity was sensitive to genetic context, increasing the likelihood that its effect was physiological.

To investigate the basis for transcriptional inhibition, BIN1 was fused in frame to the DNA binding domain of the yeast transcription factor GAL4, generating GAL4-BIN1. To control for the potential of the MBD to introduce MYC or MYC-binding coactivators to a GAL4-BIN1 DNA binding complex, chimeras that lacked the MBD (GAL4-BIN1ΔMBD) were also tested. HeLa cells were transfected with a GAL4 reporter gene, GAL4-E1b-luc, and equivalent amounts of expression vectors for unfused GAL4 DNA binding domain (GALO), GAL4-BIN1, or GAL4-BIN1ΔMBD, and cell lysates were processed for luciferase activity as before. Whereas, full-length BIN1 was observed to be only slightly repressive BIN1ΔMBD was found to be quite repressive, with the latter exhibiting a ~2.5-fold reduction in activity relative to GALO. This effect was specific because GAL4-BIN1 or GAL4-BIN1ΔMBD elicited ≦20% change in the activity of pGL2-basic, a luciferase reporter gene lacking GAL4 sites (data not shown). Taken together, the transcriptional data suggested that BIN1 acts as an adaptor for a repressor function.

EXAMPLE 10

Mechanism of Inhibition of the Oncogenic Effects of E1A or Mutant p53

A set of deletions mutants in p99f, full-length BIN1 cDNA were generated. The deletion mutants encompassed parts of the MBD and subsections thereof (amino acids 270–288, 270–315, or 323–356 of SEQ ID NO: 4), the U1 region located between the C-terminal end of the BAR region and the nuclear localization signal (NLS) (this domain is termed herein the U1 region and is located within amino acids 225–250 of SEQ ID NO: 4). BIN1ΔU1 lacks amino acids 224–248 of SEQ ID NO: 4; BIN1ΔNLS lacks amino acids 251–269 of SEQ ID NO: 4; BIN1ΔSH3 lacks amino acids 384–451 of SEQ ID NO: 4; the other mutants lack the residues indicated. BIN1 deletion mutants were subcloned for expression in pcDNA3, which was used to express BIN1 and BIN1ΔMBD. BIN1ΔBAR-C was constructed by dropping an internal Afl III restriction fragment from CMV-BIN1, resulting in a deletion of amino acids 126–206 from the BAR domain [SEQ ID NO: 4]. The remaining mutants were generated by standard PCR methodology using the oligonucleotide primers 995' (Bam), 993'SH3(Xho) (see Example 4) and others derived from the BIN1 cDNA sequence using standard techniques. The integrity of PCR-generated fragments was verified by DNA sequencing. Details for each construction are as described in Example 4D.

A. BAR-C is Required with the MBD to Suppress MYC Transformation

To map regions required for suppressing MYC transformation, REFs were transfected with expression vectors for MYC, activated RAS, and full-length or mutant BIN1, and transformed cell foci were scored two weeks later, using the assay described in Example 7 above.

Consistent with previous results, wild-type BIN1 suppressed focus formation by MYC ~6-fold relative to the empty vector control. Most of the deletion mutants inhibited focus formation as efficiently as wt BIN1. Notably the NLS-like motif and the SH3 domain were dispensable for inhibition. In contrast, deletion of either BAR-C or aa323–356 [SEQ ID NO: 4], a central MBD segment, relieved inhibition. A more N-terminal segment of the MBD between aa 270–315 [SEQ ID NO: 4] was dispensable, indicating that the 66 residue stretch between aa 323–389 [SEQ ID NO: 4] was critical. The inability of BIN1Δ323–356 or BIN1ΔBAR-C to inhibit MYC could not be due to instability of the mutant polypeptides, because each accumulated stably in COS cells similar to wtBIN1. Moreover, these mutants did not suffer a general loss of activity (e.g., due to protein misfolding), because they were able to suppress MYC-independent transformation. However, consistent with a specific lack of activity, exogenous BIN1ΔBAR-C and BIN1Δ323–356 messages each accumulated in pools of foci collected and cultured from dishes (data not shown). From this it can be concluded that BAR-C along with an MBD defined by aa 323–389 [SEQ ID NO: 4] was required to suppress MYC transformation.

B. U1 is Crucial for Suppressing E1A Transformation; Both U1 and SH3 are Crucial to Duppress Mutant p53 Transformation As described in Example 7, BIN1 has been shown to inhibit E1A-dependent transformation of REFs in a manner that was MBD-independent. The BIN1 deletion mutants described above were assayed to determine whether there was any overlap in the regions required to inhibit MYC-independent and MYC-dependent cell transformation.

BIN1 was observed to inhibit transformation by mutant p53, as well as by MYC and E1A, but the domain requirements for each oncogene were different. BIN1 inhibited the activity of mutant p53 less efficiently than E1A or MYC. However, the inhibitory effect could be increased by higher ratios of BIN1 vector in the transfected DNA (data not shown). The MBD was dispensable for inhibition of mutant p53, as well as E1A, consistent with a MYC-independent mechanism for inhibition. Deletion of the NLS-like motif had no effect. In strong contrast, U1 deletion relieved inhibition against both oncogenes and deletion of SH3 abolished inhibition of mutant p53. BAR-C was required for efficient inhibition against E1A, but the effect of BAR-C deletion was subtle compared to the effect of U1 deletion. As before, the lack of activity of BIN1ΔU1 and BIN1ΔSH3 could not be explained by polypeptide instability or a general loss of activity, since each mutant was able to suppress MYC transformation. However, consistent with a selective lack of activity, exogenous BIN1ΔU1 or BIN1ΔU1 and BIN1ΔSH3 messages were detected by Northern analysis of RNA from pools of foci cultured from cells transfected with E1A or mutant p53, respectively. Thus, the domains required to inhibit E1A and mutant p53 were overlapping, but distinct, and in each case different from those required to block MYC. From this it was concluded that BIN1 could inhibit MYC-independent transformation through two mechanisms that required U1 or the SH3 domain, respectively.

In a related study, recent data has demonstrated that the BAR-C fragment (amino acids 126–206 of BIN1, SEQ ID NO: 4) by itself is sufficient to suppress E1A transformation. These data demonstrate that the U1 domain, which is located within amino acids 225– 250 of BIN1 [SEQ ID NO: 4], is crucial for suppressing E1A transformation. Both U1 and SH3 (which is located within amino acids 378–451 of BIN1) are crucial to suppress mutant p53 transformation. Thus, these fragments of BIN1 have BIN1 biological activity which is independent of the MBD.

EXAMPLE 11

Rearrangement and Loss of Expression of the Bin1 Gene in Liver and Breast Cancer Cells A. Southern Analysis Because Bin1 had been demonstrated to inhibit Myc-dependent cell transformation and tumor cell growth, the following study was performed to determine if the Bin1 gene is mutated in human tumor cells. The initial experiment was to perform Southern analysis of the genomic DNA from a panel of human tumor cell lines including HeLa [cervix, ATCC CCL 2], SK-CO-1 [colon, ATCC HTB 39], HT-29 [colon, ATCC HTB 38], DU145 [prostate, ATCC HTB 41], PC-3 [prostate, ATCC CRL 1435], LNCaP [prostate, ATCC CRL 1740]; T24 [bladder, ATCC HTB4]; MCF7 [breast, ATCC HTB 22]; HepG2 [liver, ATCC HB 8065]; Rh-30 [myosarcoma, E. C. Douglass et al, "A specific chromosomal abnormality in rhabdosarcoma, *Cytogenet. Cell Genet.*, 45:148–155 (1987)]; Raji [lymphoma, ATCC CCL 86]. DNA from WI-38 normal diploid fibroblasts [ATCC CCL 75] was used as a source of normal DNA.

DNAs were isolated by standard methods (Sambrook et al, cited above) and 5 μg per sample was treated with HindIII restriction endonuclease. Restricted DNA was fractionated on a 0.65% agarose gel which was denatured 2×15 minutes in 1.5 M NaCl/0.5 M NaOH, neutralized 2×30 minutes in 1.5 M NaCl/0.5 TrisCl pH 8, and then blotted to a charged nylon membrane (Stratagene, La Jolla Calif.). The blot was crosslinked by UV irradiation and hybridized in a commercial hybridization solution with a random-primed $^{32}$P-labeled Bin1 cDNA probe according to the vendor's instructions (Amersham, Cambridge UK). The blot was washed 1×10 minutes with 2× SSC/0.1% SDS at 20° C. and then 2×10 minutes with 0.2 SSC/0.1% SDS at 65° C. before being exposed to X-ray film (DuPont, Wilmington Del.).

Two bands of >20 kb and 6.5 kb were observed in all the genomic DNAs except for HepG2, a liver carcinoma cell line, where an additional band of ~3.5 kb was seen. Following this observation, a second Southern analysis was performed on a panel of 9 liver carcinoma cell lines, including Huh1, Huh2, HepG2 [ATCC HB8065], Hep3B [ATCC HB8064], Hep43, Hep63, HLF [ATCC CCL 199], NCH2, and NHep40 (provided by Dr. D. Simon, Medical College of Pennsylvania). Conditions were the same as above except that PstI restriction endonuclease was used.

Five bands of 2.5, 1.8, 1.5, 0.95, and 0.75 kb were observed in WI-38 normal DNA. Four of the nine liver tumor DNAs (HepG2, Hep3B, NCH2, and NHep40) exhibited an additional band of 2.9–3.3 kb. These data corroborated the previous results and indicated that Bin1 may be mutated during the development of human hepatocarcinoma.

B. Northern Analysis

Since it could interact with a region of Myc that is mutated in tumors and could inhibit Myc transformation, Bin1 was hypothesized to represent a tumor suppressor gene product. Since a hallmark of tumor suppressors is loss of function (due to genetic or epigenetic causes) in tumor cells, Northern analysis of RNA was performed to test this hypothesis.

RNA was isolated from the initial panel of human tumor cells, including HepG2 liver carcinoma cells, and WI-38 cells. A similar analysis of RNAs isolated from mouse embryo or adult tissues was also performed. Total cytoplasmic RNA was purified by standard methods (Sambrook et al, cited above) and 15 μg was fractionated on a 1% formaldehyde agarose gel and blotted as described [G. C. Prendergast and M. D. Cole, *Mol. Cell. Biol.*, 9: 124–134 (1989)]. A commercial Northern blot containing RNA from normal human brain, heart, kidney, lung, liver, skeletal muscle, pancreas, and placenta (Clontech, Palo Alto Calif.) was also analyzed. Using the same procedure and conditions as above, the Northern blots were hybridized with Bin1 cDNA probe [G. Church et al, *Proc. Natl. Acad. Sci. USA*, 81:1991–1995 (1984)], washed, and exposed to X-ray film.

Ubiquitous expression in normal murine and human cells was observed. In the mouse, RNA levels were highest in embryo, adult brain, and adult muscle but lower levels were seen in all other tissues examined. In embryo and brain, at least two transcripts could be resolved, suggesting alternate splicing or differential usage of initiation or polyadenylation sites in some cells. In human cells, RNA levels were similar in WI-38 normal diploid fibroblasts and tumor cells derived from several different tissues. However, Bin1 message levels were undetectable in HepG2 hepatocarcinoma and MCF7 breast carcinoma cells and were >10-fold reduced in SK-CO-1 colon carcinoma cells.

Further analysis of breast and liver carcinoma cells indicated that Bin1 expression was frequently missing. Bin1 RNA was undetectable in 5/7 breast and 4/7 carcinoma cell lines examined. It was also missing in 3/6 primary breast tumors. The absence did not reflect lack of expression in breast cells, in general, because message was plainly detectable in HBL100, a flat nontumorigenic breast cell line, as well as in RNA isolated from primary breast tissues. Similar deficits were also seen in 3/6 cervix and 1/2 lung carcinoma tumor cell lines, suggesting that loss of Bin1 expression may be common to many carcinomas. These data indicated that loss of expression in tumor cell lines was not a feature of cell line establishment or long-term in vitro culturing.

C. Immunohistochemistry

The data from primary tumors was corroborated by immunohistochemical analysis of breast tissue sections, using the Bin1-specific monoclonal antibody 99D. Tissue sections on cover slips were prepared for staining by fixing 30 min at 4° C. with 4% paraformaldehyde and permeabilizing by treatment 3 min with 0.1% Triton X-100. Endogenous peroxidase was quenched by incubating slips 20 min in 0.3% methanol. Tissue was blocked 20 min with 10% normal goat serum in PBS/0.1% BSA, washed, and incubated 30 min in the same buffer with 1:10 dilution of hybridoma supernatant. The Bin1 staining pattern was identified by incubation 30 min with a goat horseradish peroxidase-conjugated anti-mouse antibody (Jackson ImmunoResearch, West Grove, Pa.) followed by a 5 min incubation with substrate. Before mounting, slides were counterstained by a 1 min incubation with 0.04% acidified solution of the cytoplasmic dye light green. Stained sections were photographed at 500× magnification. Bin1 staining was present in the cell nuclei of morphologically normal ductal epithelia. The pattern observed was consistent with the nuclear localization seen earlier and was specific since incubation of sections with secondary antibody alone produced no staining (data not shown). Consistent with the results from Northern analysis, there was little or no staining of frank carcinoma cells. It was concluded that loss of Bin1 expression occurred frequently in breast carcinoma.

EXAMPLE 12

Colony Formation Assays

The functional significance of deficits in Bin1 message levels in certain tumor cells (as in Example 11) was suggested by G418-resistant cell colony formation experiments performed in three cell lines available from the American Type Culture Collection (Rockville, Md.) that either contained (HeLa) or lacked (HepG2, MCF7) endogenous Bin1 RNA.

Colony formation assays were performed in the following manner. $3\times10^5$ cells in 3 cm dishes were transfected overnight with 2 μg CMV-Bin1 (described in Example 4) or an empty vector, using Lipofectamine (Gibco/BRL). Cells were passaged 48 hr after transfection at a 1:10 ratio into 6 cm dishes containing media with ~0.6 mg/ml G418, which permits selection for the neomycin gene present on each plasmid. Drug-resistant cell colonies were scored by crystal violet staining 2–3 weeks later. At least three trials for each cell line were performed and colonies were scored in triplicate dishes.

A. BIN1 Suppresses the Proliferation of HepG2 and MCF7 Tumor Cells

Figure 5:
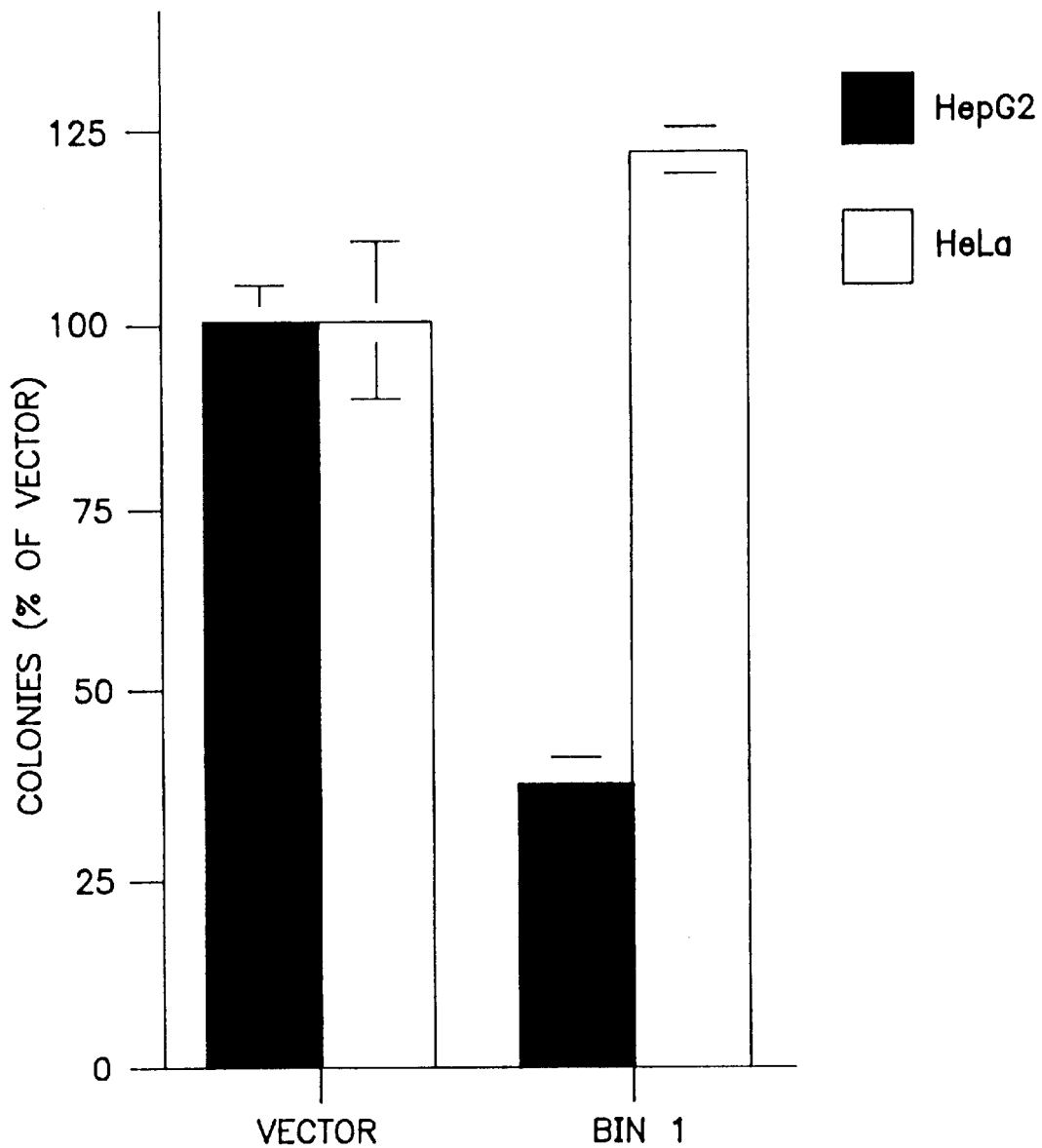
FIG. 5 is a bar chart illustrating that Bin1 vectors selectively inhibit colony formation in HepG2 hepatocarcinoma cells lacking endogenous expression. The data are depicted as the percentage of colonies obtained with empty vector.

HepG2 and MCF7 cells transfected with a Bin1 vector carrying a neomycin-resistance gene exhibited approximately 3-fold fewer colonies relative to cells transfected with empty vector, whereas no significant difference in HeLa colony formation was seen (FIG. 5). This could not be explained by either a general toxic effect or reduced transfection efficiency because the colony formation efficiency of all vectors was similar in HeLa cells. Cell populations derived from pooled colonies which emerged from Bin1-transfected HepG2 cultures showed no evidence of expression, when examined by immunoprecipitation, consistent with an incompatibility with cell growth. From this data, it can be concluded that the RNA deficits seen in carcinoma cells are functionally significant and that Bin1 is capable of exerting a tumor suppressor function.

B. BAR-C, U1 and SH3 are each Important for Efficient Suppression of Tumor Cell Growth As illustrated in Part A, BIN1 has been shown to suppress the proliferation of HepG2 and MCF7 tumor cells, which lack endogenous BIN1 expression, using a G418-resistant colony formation assay. This assay was used to assess the ability of the BIN1 deletion mutants to suppress tumor cell growth. In the present study which uses essentially the same methods, HepG2 cells were transfected with neomycin resistance gene-marked vectors for full-length or mutant BIN1 and G418-resistant colonies were scored approximately 3 weeks later. The deletion of the NLS or the MBD was observed to have no significant effect. However, an overlap with MYC requirements for inhibition existed insofar as BAR-C deletion provided the most potent, though partial, relief of BIN1 inhibition. Deletion of U1 and SH3 also partially relieved inhibition. The observation that none of these domains were completely dispensable, as was the case in REF transformation, indicated that each contributed to efficient inhibition in tumor cells. From this it was concluded that BAR-C, U1 and SH3 were each important for suppression of tumor cell growth by BIN1.

EXAMPLE 13

Epitope Mapping BIN1 Monoclonal Antibodies

BALB/c mice were immunized with the recombinant fusion protein GST-ATG99Pst described in Example 1B, which contains aa 189–398 of human BIN1 [SEQ ID NO:4], and hybridomas were generated as described (H. Koprowski et al, *Som. Cell. Genet.,* 5:957–972 (1979). ELISA was used to examine the immunoglobulins secreted into the growth media of a set of hybridomas that were obtained. Six that were strongly positive for the GST-99Pst immunogen and were negative for unfused GST, designated 99D through 99I, were characterized further.

The mAbs in each supernatant were assayed for immunoprecipitation (IP) of BIN1 or a variety of BIN1 deletion mutants [prepared as described in example 4 above] to map the approximate location of the epitopes recognized. IPs were performed as described below. The polyclonal sera, anti-99Pst, was included as a positive control. The set of deletion mutants used lacked various segments of the region of BIN1 that was included in the GST-99Pst immunogen. Briefly, [$^{35}$S]-methionine polypeptides generated by in vitro translation were incubated in IP buffer with 25 μl of each hybridoma supernatant, washed four times in IP buffer, fractionated by SDS-PAGE, and autoradiographed.

A. Immunoprecipitations

IPs were performed in NP40 buffer essentially as described [E. Harlow and D. Lane, *Antibodies: A Laboratory Manual*, Cold Spring Harbor N.Y., Cold Spring Harbor Laboratory Press, 1988]. [$^{35}$S]-methionine-labeled BIN1 mutant polypeptides were generated by in vitro translation (IVT) according to the protocol provided by the vendor (Promega). For IP, 10 μl of an IVT reaction was mixed with 25 μl of hybridoma supernatant and 20 μl protein G Sepharose beads (Pharmacia) in 0.3 ml NP40 lysis buffer (50 mM TrisCl pH 8.0/150 mM NaCl/1% NP-40) and incubated 1 hr at 4° C. on a nutator shaker. Polypeptides bound to beads were washed four times with the same buffer, resuspended in 2× SDS-PAGE gel loading buffer, boiled 3 min, fractionated on 10% SDS polyacrylamide gels, and fluorographed.

B. Results

Each of the mAbs precipitated BIN1 and all but one of the deletion mutants tested. In control experiments, none of the antibodies reacted with any of several nonspecific in vitro translation products tested. The region required by 99D mapped to a 33 residue segment of the MBD (aa 323–356 of SEQ ID NO:4). The region required by 99F, 99G, 99H, and 99I mapped to a putative nuclear localization signal (NLS) located at aa 251–269 of SEQ ID NO:4. The finding that 4/6 mAbs required this region for recognition was perhaps unsurprising, because it is highly basic and therefore would be expected to be relatively immunogenic. Recognition by 99I differed from the other NLS-specific mAb in that it less efficiently precipitated mutants lacking BAR-C, a region which comprises approximately the C-terminal half of the BIN1/amphiphysin/RVS167-related (BAR) domain of BIN1. This result suggested that BAR-C may contribute to or affect recognition of the 99I epitope. 99E recognized a noncontiguous epitope which included elements in BAR-C and the 33 aa MBD segment. The regions required for recognition by 99E and anti-99Pst sera were similar, except that anti-99Pst required a more C-terminal region of the MBD relative to 99E. The epitopes in BAR-C could be mapped to a 17 aa segment between aa 189–206 of SEQ ID NO:4, because this was the only part of BAR-C included in the GST-99Pst immunogen. This demonstrates that at least three separate epitopes located within the MBD, NLS, and BAR-C regions were recognized by this set of antibodies.

EXAMPLE 14

Western Blot Experiments with MAb

Cell extracts were prepared in NP40 buffer from human HepG2, MCF7, WI-38, and HeLa cells obtained from ATCC cultured as described in Example 12 above for C2C12 myoblasts. Fifty micrograms of cell protein were fractionated on 10% SDS polyacrylamide gels, transferred to Hybond ECL nitrocellulose (Amersham), and processed using a 1:50 dilution of hybridoma supernatant, using standard methods [E. Harlow and D. Lane, cited above]. Blots were probed with a 1:1000 dilution of alkaline phosphatase-conjugated anti-mouse IgG (BMB) for the secondary antibody and developed using a chemiluminescence kit (Pierce), following a protocol provided by the vendor.

In a series of Western blotting experiments with bacterially expressed polypeptides, 99D exhibited the highest sensitivity and specificity of the antibodies generated (data not shown). Therefore, 99D was the chief reagent used to identify and characterize BIN1 by Western analysis and immunoprecipitation (IP).

Two human lines that express BIN1 message, WI38 diploid fibroblasts and HeLa cervical carcinoma cells, and two which lack it, HepG2 hepatocarcinoma and MCF7 breast carcinoma cells were examined. Also examined were two rodent cell lines, C2C12 and Rat1. C2C12 is a skeletal myoblast line which can be induced to undergo terminal differentiation to postmitotic multinucleated myotubes by serum deprival [W. Bains et al, *Mol. Cell. Biol.*, 4:1449–1453 (1984)]. These cells were included as a positive control because BIN1 had been observed to be highly expressed in murine skeletal muscle. Rat1 is an immortalized and serum regulated fibroblast line useful for cell growth and transformation experiments.

MAb 99D specifically recognized a monomeric 70 kD polypeptide in cell lysates. The size of the polypeptide was similar to that expressed by full-length BIN1 cDNA. Consistent with its identification as cellular BIN1, the steady-state level of the 70 kD polypeptide on Western blots correlated with the level of BIN1 RNA in each cell line examined. The band detected was specific since preincubation of 99D with GST-99 immunogen eliminated its appearance on gels after IP from C2C12 cells or Western blotting (data not shown). Since the sequence of BIN1 includes three cysteines it was determined whether intermolecular disulfide bonds might stabilize oligomeric forms of BIN1 in vivo. An IP/Western experiment using C2C12 lysate in which the immunoprecipitate was fractionated on a nonreducing gel showed that the mobility of BIN1 was similar to that in reducing gels. Thus, disulfides were not involved in oligomerization. This data indicates that cellular BIN1 was a 70kD monomeric polypeptide.

EXAMPLE 15

Cellular Bin1 is a Short-Lived Phosphoprotein

As discussed herein, BIN1 was initially identified through its interaction with the putative transactivation domain of the MYC oncoprotein. MYC is induced as quiescent cells enter the cell cycle and it has a half-life of only 15–20 minutes in vivo [P. Beimbling et al, *Biochem.*, 24:6349–6355 (1985); S. R. Hann et al, *Nature*, 314, 366–369 (1985); J. E. McCormack et al, *Proc. Natl. Acad. Sci. USA*, 81:5546–5550 (1984); P. H. Rabbitts et al, *EMBO J.*, 4:2009–2015 (1985)]. Therefore, it was of interest to determine whether BIN1 may be growth regulated and/or unstable.

To address the first issue, Northern and Western analyses were performed using RNA and protein isolated from Rat1 fibroblasts that were proliferating, growth arrested at confluence, or quiescent and induced to enter the cell cycle by serum stimulation. The results indicated that BIN1 was constitutively expressed and that its steady-state levels did not vary during the cell cycle (data not shown).

To examine the stability of BIN1, a pulse-chase experiment was performed in transiently transfected COS cells as follows. COS cells cultured as above were transfected as described [C. Chen and H. Okayama, *Mol. Cell. Biol.*, 7:2745–2752 (1987)] with 20 μg of the BIN1 expression plasmid CMV-BIN1 [Example 5]. Thirty-six hours later, cells were pulse-labeled 30 min with 100 μCi/ml EXPRESS label (NEN) in growth media lacking methionine and cysteine (Gibco), washed 2 times with phosphate buffer saline (PBS), and refed with normal growth media. After 0, 2, 5, or 10 hr, cell extracts were prepared and processed for immunoprecipitation, SDS-PAGE, and fluorography as described above.

A 2-fold reduction in the intensity of the BIN1 band was observed at each time point, indicating that BIN1 had a half-life of 2 hr. Thus, it can be concluded that cellular BIN1 is relatively unstable.

While a relatively rapid turnover rate would lend itself to regulation, it has been found that the steady-state level of BIN1 did not vary in cells which were proliferating, quiescent, or induced to enter the cell cycle by growth factor stimulation.

The BIN1 amino acid sequence was then analyzed with an algorithm. Particularly, PPSEARCH/PROSITE revealed several consensus sites for serine/threonine or tyrosine phosphorylation (data not shown). Therefore, to determine whether BIN1 is a phosphoprotein, BIN1 was immunoprecipitated from extracts from C2C12 cells that were metabolically labeled with either [$^{32}$P]-orthophosphate or [$^{35}$S]-methionine.

C2Cl2 myoblasts (a gift of D. Goldhammer, University of Pennsylvania) were cultured in Dulbecco's modified Eagle media (DMEM) containing 10% fetal bovine serum and penicillin/streptomycin. Cells were labeled 4 hr in growth media lacking methionine and cysteine (Gibco) with 100 μCi/ml EXPRESS label (NEN) or in growth media lacking phosphate (Gibco) with 1 μCi/ml [$^{32}$P]-orthophosphate. Lysates prepared in NP40 buffer and phenylmethylsulfonyl fluoride, leupeptin, and apopain were centrifuged 15 min at maximum speed in a microfuge chilled to 4° C. Extract protein was precleared by a 30 min incubation at 4° C. with 20 μl protein G Sepharose beads. Complexes formed after IP of 0.5 mg precleared extract with 25 μl hybridoma supernatant in 1 ml NP40 buffer were collected on 20 μl protein G Sepharose beads and analyzed as above. Nonreducing conditions were maintained in one experiment by omitting dithiothreotol from all gel loading and preparation buffers. For the phosphatase experiment, immunoprecipitates were treated 1 hr with 10 U calf intestinal alkaline phosphatase (BMB) before SDS-PAGE and fluorography.

A specific 70 kD band was detected in both extracts derived from each cell labeling reaction by SDS-PAGE, arguing that BIN1 was indeed phosphorylated in vivo. To confirm that the 70 kD band represented a phosphorylated species, a similar experiment was performed except that the immunoprecipitates were incubated with calf intestinal phosphatase (CIP) before SDSPAGE. This treatment reduced the intensity the [$^{32}$P]-labeled but not the [$^{35}$S]-labeled BIN1 species. From this, it was concluded that cellular BIN1 was a phosphoprotein. Since it has been demonstrated that BIN1 is phosphorylated in vivo, it may be regulated by changes in its phosphorylation, permitting the function of a MYC-BIN1 complex to be regulated posttranslationally.

EXAMPLE 16

Overlapping but Distinct Localizations of BIN1 in Normal, Tumor, and Terminally Differentiated Muscle Cells To examine the localization of BIN1 in cells, immunofluorescence experiments were conducted in normal Rat1 or C2C12 cells using 99D, 99E, and 99F, which represented the three epitope specificities present among the six mAb generated.

Rat1 fibroblasts, murine C2C12 myoblasts, or human SAOS-2 osteosarcoma, LNCaP prostate carcinoma, or HeLa cells were seeded into the same growth media as above on glass coverslips. After overnight incubation, cells processed for indirect immunofluorescence using a 1:20 dilution of hybridoma supernatants essentially as described [G. C. Prendergast et al, *Genes Dev.*, 6:2429–2439 (1992)]. C2C12 cell differentiation was initiated by shifting cells from growth media to differentiation media that was the same except that it contained 5% horse serum [W. Bains et al, *Mol. Cell. Biol.*, 4:1449–1453 (1984)]. Cells were fixed with 1% paraformaldehyde/PBS, permeabilized with 0.2% Triton X-100/PBS, incubated with primary BIN1 MAb in 0.1% Triton X-100/PBS for 1 hr followed by a secondary fluorescein-conjugated anti-mouse IgG antibody (BMB), mounted in Fluoromount G (Southern Biotechnology), and viewed on a Leica immunofluorescence microscope. A myosin antibody was used as the primary antibody in parallel C2C12 trials to confirm cell differentiation.

The antibodies recognized overlapping but distinct localizations of BIN1 in cells. Rat1 fibroblasts stained with 99D or 99E displayed fluorescence in the nucleoplasm or a punctate subnuclear domain, respectively. The patterns observed with each were specific since their appearance was blocked by preincubating both antibodies with immunogen. They were not cell type-dependent because similar patterns were observed in C2C12 and other cell types (data not shown). The punctate pattern produced by 99E was similar to that observed previously using anti-99Pst to stain BIN1-transfected HepG2 cells (which lack endogenous BIN1 or BIN1 related proteins) [Example 6], consistent with the finding that the epitopes for each were related. Therefore, although the basis for the staining difference between 99D and 99E was unclear, the similarity between 99E and anti-99Pst supported the conclusion that the punctate pattern was not artifactual. These results indicated that 99D and 99E identified BIN1 species that could be distinguished in cells by differences in their nuclear localization.

In contrast to the other two antibodies, 99F did not stain either Rat1 fibroblasts or proliferating C2C12 cells. However, it detected a third pattern of BIN1 localization in C2C12 cells induced to undergo differentiation by serum deprival. In differentiated cell cultures, 99F stained the nucleus of unfused myoblasts but both nucleus and cytoplasm of elongated and fused myotube cells. Although absent in proliferating cells, the staining in differentiated cells was specific because its appearance could be blocked by preincubation of the antibody with immunogen (data not shown). Cell differentiation was confirmed by staining similar cultures with antibodies against myosin, whose expression is restricted to myotubes. Consistent with its identification of a BIN1 species, 99D produced a similar staining pattern in differentiated cells except that myotubes stained more intensely than unfused myoblasts. The data suggested that 99F recognized certain BIN1 species, absent from proliferating cells, that could localize to the cytoplasm during differentiation of muscle cells. When taken together, the results supported the interpretation that different isoforms or conformations of BIN1 are associated with different localizations in normal cells.

As described herein, previous results indicated that BIN1 expression is lacking or altered at the level of RNA in ~50% of carcinoma cells examined. In tumor cells that still expressed BIN1 RNA, the localization of BIN1 proteins was examined because of the possibility that altered localization patterns could have consequences for protein function. Therefore, HeLa cervical carcinoma, SAOS-2 osteosarcoma, and LNCaP prostate carcinoma cells, each of which had been demonstrated to express BIN1 message, were stained. 99D was used since the previous experiments suggested it was a "pan" localization antibody. In each cell line, both nucleoplasmic and subnuclear punctate staining was observed. In SAOS-2 and LNCaP cells, the punctate pattern predominated; in HeLa cells, the two compartments were stained more equally. However, in each case the localization pattern varied from that seen in proliferating Rat1 and C2C12 cells. Taken together, the results indicated that the BIN1 assumed distinct patterns of localization in normal proliferating, differentiated, and tumor cells.

In summary, in normal cells where growth in regulated, BIN1 is located primarily in the nucleoplasm but a fraction of the protein is locate in a subnuclear punctate compartment (s). However, in tumor cells, where growth is deregulated, the punctate localization predominates. The dichotomy suggests that BIN1 localization is associated with growth regulatory capability. Further supporting this, a cytoplasmic species of BIN1 has been found to be induced following terminal differentiation of muscle cells, which exit the cell cycle permanently. Notably, the antibodies employed in the study immunoprecipitated BIN1 similarly in biochemical experiments but produced different staining patterns in intact cells.

BIN1 species located in a subnuclear domain or in the cytoplasm were selectively recognized by antibodies 99E and 99F. The BIN1-related neuronal protein amphiphysin is cytoplasmic and has been implicated in endocytosis [C. David et al, Proc. Natl. Acad. Sci. USA, 93:331–335 (1996); B. Lichte et al, EMBO J., 11:2521–2530 (1992)]. Thus, cytosolic BIN1 species which appear in differentiated muscle cells might have related functions. The nature of the subnuclear structures stained by 99E was unclear. They were not nucleoli, which could be distinguished separately, so they may represent one of a set of dynamic nuclear domains which have been characterized [reviewed in D. L. Spector, Ann. Rev. Cell Biol., 9:265–315 (1993)]. Two such "nuclear dot" domains that may be germane to BIN1 and its growth inhibitory activities are the ND10 domain [C. A. Ascoli and G. G. Maul, J. Cell Biol., 112:785–795 (1991)], which is reorganized by viral proteins that induce DNA replication [T. Carbalho et al, J. Cell Biol., 131:45–56 (1995); V. Doucas et al, Genes Dev., 10:196–207 (1996); G. G. Maul et al, Virol., 217:67–75 (1996)], and a BRCA1/RAD51-associated domain, which is subject to cell cycle regulation [Y. Chen et al, Cancer Res., 56:3168–3172 (1996); R. Scully et al, Cell, 88:265–275 (1997); R. Scully et al, Science, 272:123–125 (1996); S. Tashiro et al, Oncogene, 12:2164–2170 (1996)].

EXAMPLE 17

BIN1 is Necessary for Myc-Mediated Apoptosis

A BIN1 deletion mutant lacking amino acids 143–148 [of SEQ ID NO:4] with the functionally critical BAR-C region has been determined to exert dominant inhibitory activity against full-length BIN1. For example, co-expression of BIN1Δ143–148 with BIN1 ablates the oncogenic activity of MYC.

BIN1Δ143–148 has been determined to inhibit MYC-mediated cell death. Avian fibroblasts infected with retroviral expression vectors for MYC and BIN1Δ143–148 were unable to undergo apoptosis following activation of cell death the growth factor deprivation. This result contrasted with the ability of cells to undergo cell death when expressing MYC alone or MYC plus control polypeptides. Similar results were obtained in cells infected with MYC and antisense BIN1 retroviral expression vectors, corroborating the requirement for endogenous fibroblast BIN1 in MYC-mediated apoptosis.

EXAMPLE 18

Expression of BIN1 in C2C12 Myoblasts

As described herein, Bin1 mRNA levels in murine skeletal muscle were higher than those in most other tissues, suggesting that BIN1 might have a role in this tissue. To further investigate this issue, BIN1 expression in C2C12 cells, a non-transformed myoblast cell line derived from murine skeletal muscle [H. Blau et al, Science, 230:758–766 (1985)], were examined. In serum-rich media, C2Cl2 cells proliferate rapidly, but when cultured at high density in growth factor-deficient media, the cells stop dividing, align with one another, express muscle-specific genes, and fuse into multinucleate myotubes [V. Andres et al, J. Cell Biol., 132:657–666 (1996); H. Blau et al, cited above].

BIN1 was immunoprecipitated from extracts of metabolically-labeled, proliferating C2C12 cells with the 99D MAb described herein. Samples of lysate were also immunoprecipitated with a control antibody (anti-IgD) or with 99D that had been preincubated with a molar excess of nonspecific or specific blocking proteins. Immunoprecipitates were subjected to SDS-PAGE and fluorography. 99D specifically recognized a polypeptide of ~70 kD, similar in size to that generated by in vitro translation of a full-length Bin1 cDNA. The ~70 kD protein from C2C12 cells was not recognized by isotype-matched control antibodies, nor by 99D that was preincubated with the GST-BIN1 fusion protein (incubation with unfused GST had no effect). Thus, it was concluded that 99D recognized murine Bin1 in C2C12 cells.

To determine whether Bin1 was expressed throughout the C2C12 population, cells stained with 99D were examined by flow cytometry. A suspension of proliferating cells was generated by trypsinization, then fixed, permeabilized, and stained with 99D or control antibodies followed by fluorescein-conjugated secondary antibodies. Flow cytometric analysis of the stained cell suspension demonstrated that essentially all cells in the population fluoresced above background. From this it was concluded that proliferating C2C12 cells universally expressed Bin1 protein.

EXAMPLE 19
Bin1 is Unregulated During C2C12 Differentiation

The effect of differentiation on Bin1 expression was investigated in this study. C2C12 cells grown to near confluence and then shifted to differentiation media (DM) undergo a pronounced change in morphology, in which cells elongate, align with one another, and fuse into myotubes. In the cultures studied, morphological differentiation (alignment and fusion) typically began 2–3 days following addition of DM, biochemical differentiation (expression of myosin heavy chain; see below) was detectable by days 3–4, and myotube generation was maximal (50–70% fusion) by days 5–6. To assess Bin1 expression during this period, RNA was isolated from cells at various times and subjected to Northern analysis. The level of Bin1 message in C2C12 cells increased dramatically during differentiation. Expression began to increase as early as day 2, and reached its highest level at 5 days, when cell differentiation was maximal.

To confirm that the upregulation of BIN1 message was associated with an increase in BIN1 protein, lysates from proliferating or differentiating C2C12 cells were analyzed by Western blotting with 99D. Proliferating cells contained a ~70 kD polypeptide similar to that observed by immunoprecipitation. Following induction of differentiation, the level of this protein increased slightly. In addition, differentiated cells contained higher molecular weight proteins (72–75 kD) that were recognized by 99D. These proteins appears to be BIN1-related, since they were also observed in immunoprecipitations from differentiated cells (see below), and since they were not detected when blots were probed with an isotype-matched control antibody or with 99D that had been preincubated with a GST-Bin1 blocking protein (data not shown). Thus, it was concluded that during C2C12 differentiation, BIN1 mRNA and protein levels increased and novel BIN1-related species were generated.

In examining the expression of BIN1 during C2C12 differentiation, BIN1 mRNA levels were found to be dramatically upregulated within two days of growth factor withdrawal, at approximately the same time as morphological differentiation was first detectable. Thereafter, BIN1 expression continued to increase as greater numbers of cells aligned and fused into myotubes. In addition to changes in mRNA levels, we observed changes in mRNA splicing during differentiation, with an exon corresponding to human exon 10 being introduced into BIN1 message in differentiated cells. Notably, upregulation and splicing of BIN1 mRNA (see Example 20 below) did not take place when cells were allowed to reach confluence in growth media, nor when growth factors were withdrawn from subconfluent cultures, conditions that do not promote complete morphological or biochemical differentiation. Thus, upregulation of Bin1 is intimately linked to activation of a differentiation program.

EXAMPLE 20
BIN1 mRNA is Subject to Alternative Splicing

Although the larger polypeptides that appeared during C2C12 differentiation were immunologically related to Bin1, their structural relationship to BIN1 was not clear. If they represented alternate forms of BIN1, rather than related proteins, the larger and smaller species would be expected to have similar peptide maps.

To examine this, 99D immunoprecipitates were fractionated by SDS-PAGE, and the larger and smaller species were isolated from gels and subjected to V8 protease mapping. The different species were observed to have virtually identical peptide maps (data not shown), suggesting that they represented different isoforms of BIN1.

Since one explanation for the different sizes of BIN1 was alternate RNA splicing, BIN1 mRNA structure was compared in proliferating and differentiated cells by RT-PCR. Segments representing the 5' end, middle, and 3' end of the BIN1 RNA were amplified using separate sets of primers. RT-PCR using the 5' end primers, corresponding to the N-terminal region of the polypeptide, generated a single band of ~450 bp from RNA from both proliferating and differentiated cells. In contrast, RT-PCR using the midsection primers yielded fragments of ~400 bp from proliferating cells and 445 bp from differentiated cells. Lastly, RT-PCR using the 3' end primers, corresponding to the C-terminal region of the polypeptide, yielded products of 425 and 515 bp that were present at similar levels in both proliferating and differentiated cells.

DNA sequence analysis of the 5' and 3' RT-PCR products indicated no change in the structure of these regions in proliferating and differentiated cells. The two 3' products (detected in RNA from both sources) differed in the presence or absence of a 90 bp segment encoding part of the Myc-binding domain of Bin1. Significantly, this 90 bp fragment corresponded exactly to an exon conserved in the human gene, exon 13. This result strongly suggested that a murine exon corresponding to human exon 13 was subject to alternate splicing in both proliferating and differentiated C2C12 cells.

In differentiated cells, several BIN1 bands are detected by immunoprecipitation and Western blotting, and it is possible that these species differ from one another in expression of exon 13. In proliferating cells, such heterogeneity is not readily apparent; however, longer gels offering higher resolution have revealed closely-spaced Bin1 bands that are also consistent with an exon 13 splicing event. Interestingly, exon 13 forms part of the Myc-binding domain (MBD) of Bin1, which allows it to antagonize Myc-mediated transcriptional activation and cell transformation. The fact that exon 13 is subject to alternate splicing suggests that not all Bin1 polypeptides in a cell have Myc-binding capability. Since Bin1 is known to have Myc-independent as well as Myc-dependent growth inhibitory capacity, these studies raise the possibility that different functions of Bin1 may be mediated by separate species within a cell.

Figure 6:
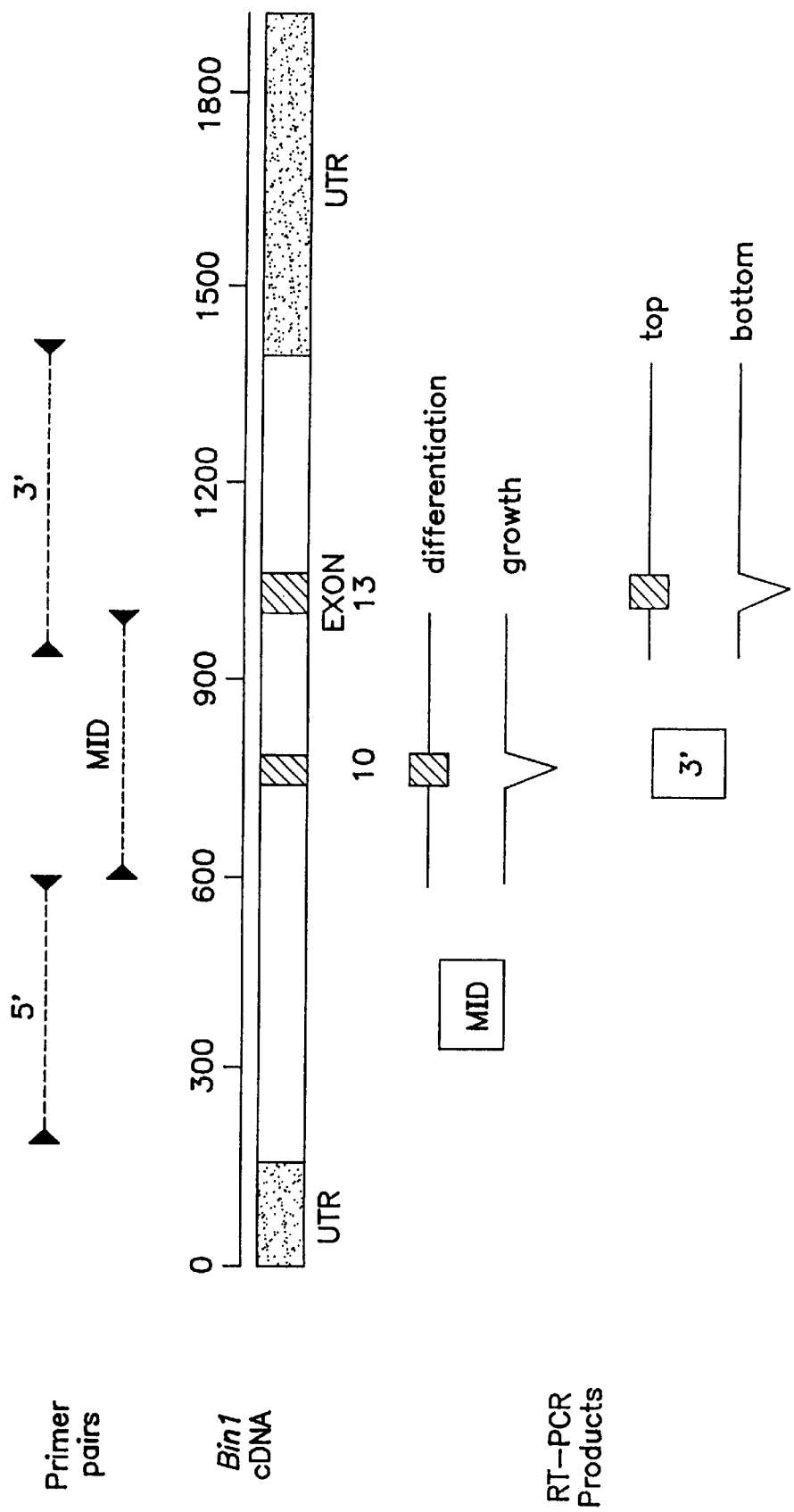
FIG. 6 illustrates the differentiation-associated isoforms generated by alternate splicing. The PCR products described in Example 20 were sequenced, and sequences from growing and differentiated cells were compared.

A similar analysis of the RT-PCR products amplified by the midsection primers showed that the 400 and 445 bp products found proliferating and differentiated cells, respectively, were identical except for the presence of an additional 45 bp segment in the latter. This segment is absent from a murine Bin1 cDNA isolated from an embryo library [A. Sparks et al, cited above], but is present in a human cDNA isolated from a skeletal muscle library. As had been observed with the 3' segment, the 45 bp segment spliced into the midsection was found to correspond to a discrete exon in the human gene, exon 10. Thus, a murine exon corresponding to human exon 10 is alternately spliced into Bin1 mRNA, and this event is regulated during C2C12 differentiation. The splice forms of Bin1 identified in this analysis are summarized in FIG. 6.

Two additional experiments were performed to verify that exon 10 was expressed only in differentiated C2C12 cells. First, total cytoplasmic RNA from proliferating and differentiated cells was subjected to Northern analysis with an oligonucleotide probe specific for exon 10 sequences: 5'-GGAGAATTCGTTGTCACTGTTCTTCTTTCTG-3', SEQ ID NO: 14. (This probe corresponds to antisense SEQ ID NO: 3, nucleotides 866–845 and a non-specific linker, indicated by underlining.) While a full-length cDNA probe recognized Bin1 mRNA from either population, the exon 10-specific probe detected message only in differentiated cells. Second, to confirm this difference at the protein level, the Bin1 mAb, 99F, that had been determined to recognize an exon 10-encoded epitope was used. 99F was found to bind in vitro translated Bin1 polypeptides that included exon 10 sequences, but not those that lacked such sequences. Moreover, 99F failed to detect Bin1 protein present in a variety of tumor cell lines, suggesting that the exon 10 epitope was masked or absent in these cells. 99F was employed as a probe to examine the exon 10-containing Bin1 species identified in differentiated C2C12 cells. Immunoprecipitations from extracts from $^{35}$S-labeled C2C12 cells indicated that 99D recognized Bin1 proteins from both proliferating and differentiated cells. In contrast, 99F failed to detect Bin1 in proliferating cells, but recognized the larger Bin1 species in differentiated cells. It was concluded that exon 10 sequences were spliced into Bin1 message during differentiation, and that the higher molecular weight species of Bin1 protein observed in differentiated cells were due to the expression of exon 10-encoded residues.

EXAMPLE 21
Changes in BIN1 Structure Correlate with Changes in Cellular Localization To begin to assess the significance of alternate splicing of exon 10 in differentiated cells, 99D and 99F were used to compare the localization of BIN1 in C2C12 cells before and after differentiation. Consistent with the results described above, in proliferating cells, BIN1 was detected by 99D but not by 99F. In these cells, as had been observed in other human and rodent cells, BIN1 was localized exclusively in the nucleus. In contrast, in differentiated myotubes, BIN1 was detected by 99D as well as 99F, and the pattern of staining with each of these rAbs was distinct. 99D staining was observed in both the nucleus and cytoplasm, while 99F staining appeared predominantly in the cytoplasm, in a fibrous pattern along the length of the myotube. These staining patterns were specific for BIN1, because they were not observed with isotype-matched control antibodies, and because they were blocked by preincubation with specific blocking proteins (data not shown). In addition, staining with an antibody specific for myosin heavy chain confirmed that extensive differentiation had taken place in these cultures. Taken together, these results indicated that the low molecular weight form of BIN1 in proliferating C2C12 cells was confined to the nucleus, whereas the high molecular weight, differentiation-associated BIN1 species were found predominantly in the cytoplasm.

While the functional significance of exon 10 splicing remains unclear, its correlation with cytosolic localization suggests that exon 10 sequences may be responsible for targeting of BIN1 to the cytosol. Counterintuitively, exon 10 encodes a highly basic segment which resembles nuclear localization signal (NLS) motifs [T. Boulikas, *Crit. Rev. Euk. Gene Exp.*, 3:193–227 (1993)]. In the context of BIN1, however, this motif is neither necessary nor sufficient for nuclear localization, since BIN1 species that lack exon 10 are found in the nucleus of C2C12 cells, as well as other human and rodent cell lines, and species that contain exon 10 are present in the nucleus and the cytoplasm of C2C12-derived myotubes. An alternative function for exon 10 may be revealed by ongoing analysis of a recently identified BIN1-interacting protein whose binding depends on exon 10-encoded sequences.

Although alternate splicing explains some of the major differences observed in BIN1 species in C2C12 cells, additional complexity in BIN1 structure is likely to exist. Work in human cell lines has provided evidence for alternate splicing of another exon in the central region of the BIN1 gene, exon 12. While exon 12 has not been detected in mRNA from either human muscle cells or C2C12 cells, this exon might be spliced at earlier stages of muscle differentiation or in other cell lineages. Post-translational modification may also contribute to structural variation, because Bin1 has been found to be phosphorylated in both proliferating and differentiated C2C12 cells.

EXAMPLE 22
BIN1 is Necessary for C2C12 Differentiation

The complex regulation of Bin1 structure and localization during differentiation suggested that it might play a role in the differentiation process. To test this hypothesis, the effects of overexpression sense or antisense forms of human Bin1 cDNA in C2C12 cells were investigated. Cells were transfected with an expression vector encoding a neomycin resistance gene (neo) or the same vector containing a full-length human Bin1 cDNA (sense or antisense). Cell lines derived from G418-resistant colonies were screened for expression of exogenous BIN1 by RT-PCR, using primers specific for the human cDNA that was introduced.

Only a limited number (10–20%) of the cell lines derived from sense-transfected cells showed elevated expression of Bin1. In addition, cells showing exogenous Bin1 expression grew more slowly than control cell lines, both during and after the selection period. These observations argued that Bin1 overexpression might interfere with the growth of C2C12 cells, consistent with results in other cell lines. To examine the effects of Bin1-overexpression on differentiation, several Bin1-overexpressing cell lines were selected for further analysis. Relative to control lines, these cells had significant amounts of exogenous Bin1 mRNA detectable by RT-PCR. Western analysis of extracts derived from these cells showed 2- to 4-fold higher levels of Bin1 protein, as detected by 99D. Despite elevated levels of Bin1, however, their morphology in growth media was similar to that of control cells (data not shown), with no evidence of premature alignment or fusion. Bin1 overexpression may impede C2C12 proliferation to some extent, but on its own was not sufficient to drive differentiation in growth media (GM).

The behavior of control and sense-expressing cells in differentiation media (DM) was examined. After 3 days in DM, control cells became elongated and aligned, but showed limited fusion into myotubes. Consistent with these observations, only modest increases in expression of differentiation-associated isoforms of endogenous Bin1 and myosin heavy chain were observed. Although control cells showed increased alignment and fusion after longer culturing in DM (see below), they seldom displayed the rate or degree of differentiation observed in parental (non-transfected) cells. This blunted differentiation response in transfected cells may be due to the high density at which cells are cultured during the drug selection period.)

In contrast to control cells, Bin1-overexpressing cells underwent rapid and pronounced differentiation in DM. In fact, these cells differentiated even more vigorously than parental C2C12 cells. Within 2–3 days of culture in DM they exhibited sharp increases in the overall level of BIN1 protein (mainly due to increases in endogenous expression), with significant accumulation of the high molecular weight differentiation-associated species. In parallel with this upregulation, sense-expressing cells also exhibited a dramatic increase in myosin heavy chain levels, efficient cell alignment, and extensive cell fusion into myotubes. The rapid and efficient differentiation observed was not vector dependent, because we observed similar phenomena in cells that were transfected with two other Bin1 vectors. It was concluded that elevation of BIN1 levels was insufficient to induce C2C12 differentiation but accelerated or enhanced the differentiation program once it was initiated.

Antisense-expressing cell lines were examined to determine whether BIN1 was a necessary component of the differentiation program. Unlike sense transfectants, a significant proportion (50–60%) of the G418-resistant cell lines transfected with the antisense vector exhibited expression of the exogenous construct by RT-PCR. Moreover, whereas the sense-expressing cells were observed to grow more slowly than controls, antisense-expressing cells proliferated somewhat more rapidly, such that more frequent passaging was necessary to avoid confluence. Western blotting revealed a 2- to 4-fold decrease in basal levels of Bin1 protein in antisense-expressing cells relative to controls. Similar to sense-expressing cell lines, the morphology of antisense-expressing cells in growth media was indistinguishable from that of control cells, and these cells showed no increased tendency to undergo alignment or fusion.

The effects of antisense expression on differentiation were determined by examining the same set of biochemical and morphological features as described above, in cells cultured in DM for up to six days (a time point at which control cells exhibited maximal morphologic differentiation). Compared to control lines, antisense lines showed significantly less upregulation of differentiation associated BIN1 species. In addition, while control cells exhibited increased levels of myosin heavy chain, antisense-expressing cells showed little upregulation of this marker. Finally, while control cells showed substantial alignment and some fusion after six days in DM, antisense lines showed little if any alignment, instead retaining the rounded morphology that is characteristic of undifferentiated cells. On the basis of these observations, it was concluded that upregulation of Bin1 is necessary for differentiation of C2C12 cells.

Perturbing BIN1 expression in C2C12 cells was found to altered their growth and their susceptibility to induction of differentiation. Expression of exogenous BIN1 (in the sense orientation) interfered with cell growth and promoted cell differentiation. The effects of Bin1 on growth were inferred from the fact that only a small proportion of G418-resistant BIN1-transfected cells showed overexpression of the exogenous gene by RT-PCR. One interpretation of this finding was that cells expressing high levels of Bin1 had a growth disadvantage and were diluted out during the selection period by cells that expressed lower levels of the gene. Consistent with this notion, the lines that did survive selection expressed only moderate levels of exogenous BIN1 (a 2- to 4-fold higher level of expression relative to controls) and grew more slowly than empty vector control lines. The ability of BIN1 to inhibit cell growth has described herein.

Notably, exogenous BIN1 expression did not promote differentiation of C2C12 cells in growth media, but dramatically accelerated and enhanced expression of the differentiation program induced by growth factor withdrawal. This accelerated differentiation was observed both morphologically (in terms of cell alignment and fusion) and biochemically (in terms of increased expression of myosin heavy chain and of endogenous BIN1). The fact that BIN1-expressing cells cultured in DM showed more rapid upregulation of differentiation-associated BIN1 isoforms than control or parental cells suggested that BIN1 may positively regulate its own expression, a possibility which needs further investigation. It should be noted that the sense BIN1 experiments all employed a full-length human BIN1 cDNA that had been isolated from a skeletal muscle library. Since this cDNA contains exon 10- and exon 13-related sequences, the results of these experiments reflect only the activity of BIN1 species containing these exons.

The analysis of antisense-expressing cells also strongly supported a role for Bin1 in differentiation. In these cells, the morphological and biochemical features of differentiation were diminished significantly compared to control cells. Although precisely where BIN1 acts in the differentiation pathway was not determined, the fact that BIN1 upregulation occurs relatively quickly (within 2 days of serum withdrawal), and the fact that antisense BIN1 inhibits the earliest morphological signs of differentiation, suggests that it may function rather early. Taken together, the data argues that BIN1 upregulation (and possibly splicing) may be a rate-limiting step in the differentiation program.

The mechanism by which BIN1 acts during differentiation is unclear. However, studies of Bin1 structure and function in cell transformation prompt several testable hypotheses. First, as discussed above, Bin1 can interact with the Myc oncoprotein, and can inhibit Myc-mediated transcription and transformation. Previous studies on the role of Myc in muscle differentiation indicate that overexpression of this gene can interfere with biochemical differentiation and/or fusion [M. Crescenzi et al, *J. Cell Biol.*, 125:1137–1145 (1994); N. Denis et al, *Exp. Cell Res.*, 172:212–217 (1987); S. La Rocca et al, *Oncogene*, 9:3499–3508 (1994); E. Olson, *Dev. Biol.*, 154:261–272 (1992)]. In this light, one possible function of BIN1 may be to antagonize Myc, and thereby relieve cells of a significant barrier to differentiation. Investigation of the effects of Myc and BIN1 cotransfection in C2C12 cells may shed light on this possibility.

In addition to its Myc-related functions, BIN1 also can act in a Myc-independent manner. For example, BIN1 can inhibit transformation of primary rat embryo fibroblasts by the adenovirus gene product E1A, in a manner independent of the MBD. Since E1A can inhibit differentiation of myoblasts and reactivate the cell cycle in differentiated myotubes [M. Tiainen et al, *Mol. Cell. Biol.*, 16:5302–5312 (1996); K. Webster et al, *Nature*, 332:553–557 (1988)], it is possible that Bin1 may counteract these effects as well. In this scenario, Bin1 may function in differentiation by directly or indirectly affecting known targets of E1A such as Rb, p107 and p300/CBP [N. Dyson, *J. Cell Sci. Supple* 18:81–87 (1994); R. Eckner et al, *Genes Dev.*, 10:2478–2490 (1996);

W. Gu et al, *Science,* 264:251–254 (1994); M. Tiainen et al, cited above]. Similarly, BIN1 has been observed to inhibit cell transformation by a dominant inhibitory mutant of p53. Although the mechanism of this effect is not clear, the fact that p53 function is required for C2C12 differentiation [S. Soddu et al, *J. Cell Biol.,* 134:193–204 (1996)] raises the possibility that Bin1 could also exert its effects on differentiation via p53.

These studies demonstrate that BIN1 can regulate muscle differentiation. Since BIN1 is expressed ubiquitously, it may also contribute to the control of differentiation programs in other cell types. Consistent with this possibility, Bin1 expression and splicing patterns are altered in a manner similar to that observed in C2C12 cells during induction of the monocytic differentiation program in the promyelocytic cell line HL-60 [S. Collins et al, *Nature,* 270:347–349 (1977)]. Thus, BIN1 may have a general role in cell differentiation, contributing to the detrimental effects of its loss in cancer cells.

All documents cited above are incorporated herein by reference. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. An isolated anti-Bin1 antibody which specifically binds to a Box-dependent myc-interacting peptide (Bin1) selected from the group consisting of:
   (a) SEQ ID NO:2; and
   (b) SEQ ID NO:4.

2. An isolated anti-Bin1 specific antibody raised against a Box-dependent myc-interacting peptide (Bin1), said peptide selected from the group consisting of:
   (a) SEQ ID NO:2; and
   (b) SEQ ID NO:4.

3. The anti-Bin1 antibody according to claim 2, wherein said antibody binds to a Bin1 fragment selected from the group consisting of:
   (a) amino acids 190 to 250 of SEQ ID NO:4;
   (b) amino acids 270 to 383 of SEQ ID NO:4;
   (c) amino acids 378 to 451 of SEQ ID NO:4;
   (d) amino acids 252 to 265 of SEQ ID NO:4;
   (e) amino acids 224 to 251 of SEQ ID NO:4;
   (f) amino acids 1 to 250 of SEQ ID NO:4; and
   (g) amino acids 323 to 359 of SEQ ID NO:4.

4. The antibody according to claim 1, selected from the group consisting of a chimeric antibody, a humanized antibody, a monoclonal antibody and a polyclonal antibody.

5. The antibody according to claim 1 selected from the group of monoclonal antibodies consisting of 99D and 99I.

6. An anti-idiotype antibody specific for the antibody of claim 1.

7. A diagnostic reagent comprising the antibody according to claim 1 and a detectable label.

8. A method of detecting a cancer or a hyperplastic disease state associated with abnormal levels of Bin1 comprising the steps of:
   providing a sample from a patient suspected of having said cancer or disease;
   contacting said sample with an anti-Bin1 antibody which specifically binds to a Box-dependent myc-interacting peptide (Bin1) selected from the group consisting of:
      (a) SEQ ID NO:2;
      (b) SEQ ID NO:4, excluding exon 10; and
      (c) a fragment of (a) or (b) comprising 8 amino acids; and
   detecting binding of said anti-Bin1 antibody to said sample.

9. A method of detecting a deficiency in Box-dependent myc-interacting peptide in a patient comprising providing a sample from a patient suspected of having said deficiency and incubating said sample in the presence of a diagnostic reagent according to claim 7, wherein decreased binding of anti-Bin1 antibodies as compared to a sample from a non-diseased patient indicates the presence of a disorder characterized by a deficiency in Bin1.

10. The anti-Bin1 antibody according to claim 1, wherein said antibody binds to a Bin1 fragment selected from the group consisting of:
(a) amino acids 126 to 206 of SEQ ID NO:4;
(b) amino acids 143 to 148 of SEQ ID NO:4;
(c) amino acids 225 to 250 of SEQ ID NO:4;
(d) amino acids 323 to 356 of SEQ ID NO:4;
(e) amino acids 190 to 250 of SEQ ID NO:4;
(f) amino acids 270 to 383 of SEQ ID NO:4;
(g) amino acids 378 to 451 of SEQ ID NO:4;
(h) amino acids 252 to 265 of SEQ ID NO:4;
(i) amino acids 224 to 251 of SEQ ID NO:4;
(j) amino acids 1 to 250 of SEQ ID NO:4; and
(k) amino acids 323 to 389 of SEQ ID NO:4.

11. Anti-Bin1 monoclonal antibody 99D.

12. A method of generating an anti-Bin1 antibody comprising the step of using an antigen consisting of a Bin1 protein or peptide generate anti-Bin1 specific antibody, said protein or peptide selected from the group consisting of:
(a) SEQ ID NO:2;
(b) SEQ ID NO:4, and
(c) a fragment of (a) or (b) comprising 8 amino acids.

13. The method according to claim 8, wherein said cancer is selected from the group consisting of prostate cancer and liver cancer.

14. A method of detecting prostate cancer comprising the steps of:
providing a sample from a patient suspected of having prostate cancer,
contacting said sample with an anti-Bin1 antibody which binds to a Box-dependent myc-interacting peptide (Bin1) selected from the group consisting of:
(a) SEQ ID NO:2;
(b) SEQ ID NO:4, excluding exon 10; and
(c) a fragment of (a) or (b) comprising 8 amino acids, and
detecting binding of said anti-Bin1 antibody to said sample.

15. The method according to claim 14, wherein said anti-Bin1 antibody is 99D.

16. An antibody comprising the complementarity determining regions of an anti-Bin1 monoclonal antibody selected from the group consisting of 99D and 99I.

17. The antibody according to claim 16, wherein said antibody is a humanized antibody.

18. The antibody according to claim 16, wherein said antibody is a chimeric antibody.

19. Anti-Bin1 monoclonal antibody 99I.

20. The method according to claim 12, wherein said fragment is selected from the group consisting of:
amino acids 126 to 206 of SEQ ID NO: 4;
amino acids 143 to 148 of SEQ ID NO: 4;
amino acids 225 to 250 of SEQ ID NO: 4;
amino acids 323 to 356 of SEQ ID NO: 4;
amino acids 190 to 250 of SEQ ID NO: 4;
amino acids 270 to 383 of SEQ ID NO: 4;
amino acids 378 to 451 of SEQ ID NO: 4;
amino acids 224 to 251 of SEQ ID NO: 4;
amino acids 1 to 250 of SEQ ID NO: 4; and
amino acids 323 to 389 of SEQ ID NO: 4.

21. An anti-Bin1 antibody which specifically binds to a Bin1 peptide, said antibody generated according to the method of claim 12.

22. A chimeric anti-Bin1 antibody which specifically binds to a Box-dependent myc-interacting peptide (Bin1) selected from the group consisting of:
(a) SEQ ID NO:2; and
(b) SEQ ID NO:4.

23. A humanized anti-Bin1 antibody which specifically binds to a Box-dependent myc-interacting peptide (Bin1) selected from the group consisting of:
(a) SEQ ID NO:2; and
(b) SEQ ID NO:4.

24. A monoclonal anti-Bin1 antibody which specifically binds to a Box-dependent myc-interacting peptide (Bin1) selected from the group consisting of:
(a) SEQ ID NO:2; and
(b) SEQ ID NO:4.

* * * * *

```
                           SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 402 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..399

(xi) SEQUENCE DESCRIPTION: SEQ ID NO:1:

GAG ATC AGA GTG AAC CAT GAG CCA GAG CCG GCC AGT GGG GCC TCA CCC        48
Glu Ile Arg Val Asn His Glu Pro Glu Pro Ala Ser Gly Ala Ser Pro
  1               5                  10                  15

GGG GCT GCC ATC CCC AAG TCC CCA TCT CAG CCA GCA GAG GCC TCC GAG        96
Gly Ala Ala Ile Pro Lys Ser Pro Ser Gln Pro Ala Glu Ala Ser Glu
             20                  25                  30

GTG GTG GGT GGA GCC CAG GAG CCA GGG GAG ACA GCA GCC AGT GAA GCA       144
Val Val Gly Gly Ala Gln Glu Pro Gly Glu Thr Ala Ala Ser Glu Ala
         35                  40                  45

ACC TCC AGC TCT CTT CCG GCT GTG GTG GTG GAG ACC TTC TCC GCA ACT       192
Thr Ser Ser Ser Leu Pro Ala Val Val Val Glu Thr Phe Ser Ala Thr
     50                  55                  60

GTG AAT GGG GCG GTG GAG GGC AGC GCT GGG ACT GGA CGC TTG GAC CTG       240
Val Asn Gly Ala Val Glu Gly Ser Ala Gly Thr Gly Arg Leu Asp Leu
 65                  70                  75                  80

CCC CCG GGA TTC ATG TTC AAG GTT CAA GCC CAG CAT GAT TAC ACG GCC       288
Pro Pro Gly Phe Met Phe Lys Val Gln Ala Gln His Asp Tyr Thr Ala
                 85                  90                  95

ACT GAC ACT GAT GAG CTG CAA CTC AAA GCT GGC GAT GTG GTG TTG GTG       336
Thr Asp Thr Asp Glu Leu Gln Leu Lys Ala Gly Asp Val Val Leu Val
            100                 105                 110

ATT CCT TTC CAG AAC CCA GAG GAG CAG GAT GAA GGC TGG CTC ATG GGT       384
Ile Pro Phe Gln Asn Pro Glu Glu Gln Asp Glu Gly Trp Leu Met Gly
        115                 120                 125

GTG AAG GAG AGC GAC TGA                                                402
Val Lys Glu Ser Asp
    130

(2) INFORMATION FOR SEQ ID NO:2:
```

-continued (i) SEQUENCE CHARACTERISTICS:
    (A) LENGTH: 133 amino acids
    (B) TYPE: amino acid
    (D) TOPOLOGY: linear (ii) MOLECULE TYPE: protein (xi) SEQUENCE DESCRIPTION: SEQ ID NO:2:

```
Glu Ile Arg Val Asn His Glu Pro Glu Pro Ala Ser Gly Ala Ser Pro
 1               5                  10                  15

Gly Ala Ala Ile Pro Lys Ser Pro Ser Gln Pro Ala Glu Ala Ser Glu
            20                  25                  30

Val Val Gly Gly Ala Gln Glu Pro Gly Glu Thr Ala Ala Ser Glu Ala
        35                  40                  45

Thr Ser Ser Leu Pro Ala Val Val Glu Thr Phe Ser Ala Thr
    50                  55                  60

Val Asn Gly Ala Val Glu Gly Ser Ala Gly Thr Gly Arg Leu Asp Leu
65                  70                  75                  80

Pro Pro Gly Phe Met Phe Lys Val Gln Ala Gln His Asp Tyr Thr Ala
                85                  90                  95

Thr Asp Thr Asp Glu Leu Gln Leu Lys Ala Gly Asp Val Val Leu Val
                100                 105                 110

Ile Pro Phe Gln Asn Pro Glu Glu Gln Asp Glu Gly Trp Leu Met Gly
            115                 120                 125

Val Lys Glu Ser Asp
    130
```

(2) INFORMATION FOR SEQ ID NO:3:

(i) SEQUENCE CHARACTERISTICS:
        (A) LENGTH: 1925 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 60..1412

(xi) SEQUENCE DESCRIPTION: SEQ ID NO:3:

```
GAATTCCGTG CTGGTTGAGC TTGCTCATCT CCTTGTGGAA GTTTTCCTCC AGGCCCGCG      59

ATG CTC TGG AAC GTG GTG ACG GCG GGA AAG ATC GCC AGC AAC GTG CAG     107
Met Leu Trp Asn Val Val Thr Ala Gly Lys Ile Ala Ser Asn Val Gln
 1               5                  10                  15

AAG AAG CTC ACC CGC GCG CAG GAG AAG GTT CTC CAG AAG CTG GGG AAG     155
Lys Lys Leu Thr Arg Ala Gln Glu Lys Val Leu Gln Lys Leu Gly Lys
            20                  25                  30

GCA GAT GAG ACC AAG GAT GAG CAG TTT GAG CAG TGC GTC CAG AAT TTC     203
Ala Asp Glu Thr Lys Asp Glu Gln Phe Glu Gln Cys Val Gln Asn Phe
        35                  40                  45

AAC AAG CAG CTG ACG GAG GGC ACC CGG CTG CAG AAG GAT CTC CGG ACC     251
Asn Lys Gln Leu Thr Glu Gly Thr Arg Leu Gln Lys Asp Leu Arg Thr
    50                  55                  60

TAC CTG GCC TCC GTC AAA GCC ATG CAC GAG GCT TCC AAG AAG CTG AAT     299
Tyr Leu Ala Ser Val Lys Ala Met His Glu Ala Ser Lys Lys Leu Asn
65                  70                  75                  80

GAG TGT CTG CAG GAG GTG TAT GAG CCC GAT TGG CCC GGC AGG GAT GAG     347
Glu Cys Leu Gln Glu Val Tyr Glu Pro Asp Trp Pro Gly Arg Asp Glu
                85                  90                  95

GCA AAC AAG ATC GCA GAG AAC AAC GAC CTG CTG TGG ATG GAT TAC CAC     395
```

|     |     |     |     |     |     |     |     |     |     |     |     |     |     |      |
|-----|-----|-----|-----|-----|-----|-----|-----|-----|-----|-----|-----|-----|-----|------|
| Ala | Asn | Lys | Ile | Ala | Glu | Asn | Asn | Asp | Leu | Leu | Trp | Met | Asp | Tyr His |
|     |     |     | 100 |     |     |     | 105 |     |     |     |     | 110 |     |      |

| CAG | AAG | CTG | GTG | GAC | CAG | GCG | CTG | CTG | ACC | ATG | GAC | ACG | TAC | CTG | GGC | 443 |
|-----|-----|-----|-----|-----|-----|-----|-----|-----|-----|-----|-----|-----|-----|-----|-----|-----|
| Gln | Lys | Leu | Val | Asp | Gln | Ala | Leu | Leu | Thr | Met | Asp | Thr | Tyr | Leu | Gly |     |
|     |     | 115 |     |     |     | 120 |     |     |     |     | 125 |     |     |     |     |     |

| CAG | TTC | CCC | GAC | ATC | AAG | TCA | CGC | ATT | GCC | AAG | CGG | GGG | CGC | AAG | CTG | 491 |
|-----|-----|-----|-----|-----|-----|-----|-----|-----|-----|-----|-----|-----|-----|-----|-----|-----|
| Gln | Phe | Pro | Asp | Ile | Lys | Ser | Arg | Ile | Ala | Lys | Arg | Gly | Arg | Lys | Leu |     |
|     |     | 130 |     |     |     | 135 |     |     |     | 140 |     |     |     |     |     |     |

| GTG | GAC | TAC | GAC | AGT | GCC | CGG | CAC | CAC | TAC | GAG | TCC | CTT | CAA | ACT | GCC | 539 |
|-----|-----|-----|-----|-----|-----|-----|-----|-----|-----|-----|-----|-----|-----|-----|-----|-----|
| Val | Asp | Tyr | Asp | Ser | Ala | Arg | His | His | Tyr | Glu | Ser | Leu | Gln | Thr | Ala |     |
| 145 |     |     |     |     | 150 |     |     |     | 155 |     |     |     |     | 160 |     |     |

| AAA | AAG | AAG | GAT | GAA | GCC | AAA | ATT | GCC | AAG | GCC | GAG | GAG | GAG | CTC | ATC | 587 |
|-----|-----|-----|-----|-----|-----|-----|-----|-----|-----|-----|-----|-----|-----|-----|-----|-----|
| Lys | Lys | Lys | Asp | Glu | Ala | Lys | Ile | Ala | Lys | Ala | Glu | Glu | Glu | Leu | Ile |     |
|     |     |     |     | 165 |     |     |     | 170 |     |     |     |     | 175 |     |     |     |

| AAA | GCC | CAG | AAG | GTG | TTT | GAG | GAG | ATG | AAT | GTG | GAT | CTG | CAG | GAG | GAG | 635 |
|-----|-----|-----|-----|-----|-----|-----|-----|-----|-----|-----|-----|-----|-----|-----|-----|-----|
| Lys | Ala | Gln | Lys | Val | Phe | Glu | Glu | Met | Asn | Val | Asp | Leu | Gln | Glu | Glu |     |
|     |     |     | 180 |     |     |     |     | 185 |     |     |     |     | 190 |     |     |     |

| CTG | CCG | TCC | CTG | TGG | AAC | AGC | CGC | GTA | GGT | TTC | TAC | GTC | AAC | ACG | TTC | 683 |
|-----|-----|-----|-----|-----|-----|-----|-----|-----|-----|-----|-----|-----|-----|-----|-----|-----|
| Leu | Pro | Ser | Leu | Trp | Asn | Ser | Arg | Val | Gly | Phe | Tyr | Val | Asn | Thr | Phe |     |
|     |     |     | 195 |     |     |     | 200 |     |     |     |     | 205 |     |     |     |     |

| CAG | AGC | ATC | GCG | GGC | CTG | GAG | GAA | AAC | TTC | CAC | AAG | GAG | ATG | AGC | AAG | 731 |
|-----|-----|-----|-----|-----|-----|-----|-----|-----|-----|-----|-----|-----|-----|-----|-----|-----|
| Gln | Ser | Ile | Ala | Gly | Leu | Glu | Glu | Asn | Phe | His | Lys | Glu | Met | Ser | Lys |     |
|     |     | 210 |     |     |     |     | 215 |     |     |     |     | 220 |     |     |     |     |

| CTC | AAC | CAG | AAC | CTC | AAT | GAT | GTG | CTG | GTC | GGC | CTG | GAG | AAG | CAA | CAC | 779 |
|-----|-----|-----|-----|-----|-----|-----|-----|-----|-----|-----|-----|-----|-----|-----|-----|-----|
| Leu | Asn | Gln | Asn | Leu | Asn | Asp | Val | Leu | Val | Gly | Leu | Glu | Lys | Gln | His |     |
| 225 |     |     |     | 230 |     |     |     |     | 235 |     |     |     |     | 240 |     |     |

| GGG | AGC | AAC | ACC | TTC | ACG | GTC | AAG | GCC | CAG | CCC | AGA | AAG | AAA | AGT | AAA | 827 |
|-----|-----|-----|-----|-----|-----|-----|-----|-----|-----|-----|-----|-----|-----|-----|-----|-----|
| Gly | Ser | Asn | Thr | Phe | Thr | Val | Lys | Ala | Gln | Pro | Arg | Lys | Lys | Ser | Lys |     |
|     |     |     |     | 245 |     |     |     | 250 |     |     |     |     | 255 |     |     |     |

| CTG | TTT | TCG | CGG | CTG | CGC | AGA | AAG | AAG | AAC | AGT | GAC | AAC | GCG | CCT | GCA | 875 |
|-----|-----|-----|-----|-----|-----|-----|-----|-----|-----|-----|-----|-----|-----|-----|-----|-----|
| Leu | Phe | Ser | Arg | Leu | Arg | Arg | Lys | Lys | Asn | Ser | Asp | Asn | Ala | Pro | Ala |     |
|     |     |     | 260 |     |     |     |     | 265 |     |     |     |     | 270 |     |     |     |

| AAA | GGG | AAC | AAG | AGC | CCT | TCG | CCT | CCA | GAT | GGC | TCC | CCT | GCC | GCC | ACC | 923 |
|-----|-----|-----|-----|-----|-----|-----|-----|-----|-----|-----|-----|-----|-----|-----|-----|-----|
| Lys | Gly | Asn | Lys | Ser | Pro | Ser | Pro | Pro | Asp | Gly | Ser | Pro | Ala | Ala | Thr |     |
|     |     |     | 275 |     |     |     | 280 |     |     |     |     | 285 |     |     |     |     |

| CCC | GAG | ATC | AGA | GTC | AAC | CAC | GAG | CCA | GAG | CCG | GCC | GGC | GGG | GCC | ACG | 971 |
|-----|-----|-----|-----|-----|-----|-----|-----|-----|-----|-----|-----|-----|-----|-----|-----|-----|
| Pro | Glu | Ile | Arg | Val | Asn | His | Glu | Pro | Glu | Pro | Ala | Gly | Gly | Ala | Thr |     |
|     | 290 |     |     |     |     | 295 |     |     |     |     | 300 |     |     |     |     |     |

| CCC | GGG | GCC | ACC | CTC | CCC | AAG | TCC | CCA | TCT | CAG | CCA | GCA | GAG | GCC | TCG | 1019 |
|-----|-----|-----|-----|-----|-----|-----|-----|-----|-----|-----|-----|-----|-----|-----|-----|------|
| Pro | Gly | Ala | Thr | Leu | Pro | Lys | Ser | Pro | Ser | Gln | Pro | Ala | Glu | Ala | Ser |      |
| 305 |     |     |     |     | 310 |     |     |     |     | 315 |     |     |     |     | 320 |      |

| GAG | GTG | GCG | GGT | GGG | ACC | CAA | CCT | GCG | GCT | GGA | GCC | CAG | GAG | CCA | GGG | 1067 |
|-----|-----|-----|-----|-----|-----|-----|-----|-----|-----|-----|-----|-----|-----|-----|-----|------|
| Glu | Val | Ala | Gly | Gly | Thr | Gln | Pro | Ala | Ala | Gly | Ala | Gln | Glu | Pro | Gly |      |
|     |     |     |     | 325 |     |     |     |     | 330 |     |     |     |     | 335 |     |      |

| GAG | ACG | GCG | GCA | AGT | GAA | GCA | GCC | TCC | AGC | TCT | CTT | CCT | GCT | GTC | GTG | 1115 |
|-----|-----|-----|-----|-----|-----|-----|-----|-----|-----|-----|-----|-----|-----|-----|-----|------|
| Glu | Thr | Ala | Ala | Ser | Glu | Ala | Ala | Ser | Ser | Ser | Leu | Pro | Ala | Val | Val |      |
|     |     |     | 340 |     |     |     |     | 345 |     |     |     |     | 350 |     |     |      |

| GTG | GAG | ACC | TTC | CCA | GCA | ACT | GTG | AAT | GGC | ACC | GTG | GAG | GGC | GGC | AGT | 1163 |
|-----|-----|-----|-----|-----|-----|-----|-----|-----|-----|-----|-----|-----|-----|-----|-----|------|
| Val | Glu | Thr | Phe | Pro | Ala | Thr | Val | Asn | Gly | Thr | Val | Glu | Gly | Gly | Ser |      |
|     |     |     | 355 |     |     |     |     | 360 |     |     |     |     | 365 |     |     |      |

| GGG | GCC | GGG | CGC | TTG | GAC | CTG | CCC | CCA | GGT | TTC | ATG | TTC | AAG | GTA | CAG | 1211 |
|-----|-----|-----|-----|-----|-----|-----|-----|-----|-----|-----|-----|-----|-----|-----|-----|------|
| Gly | Ala | Gly | Arg | Leu | Asp | Leu | Pro | Pro | Gly | Phe | Met | Phe | Lys | Val | Gln |      |
|     | 370 |     |     |     |     | 375 |     |     |     |     | 380 |     |     |     |     |      |

| GCC | CAG | CAC | GAC | TAC | ACG | GCC | ACT | GAC | ACA | GAC | GAG | CTG | CAG | CTC | AAG | 1259 |
|-----|-----|-----|-----|-----|-----|-----|-----|-----|-----|-----|-----|-----|-----|-----|-----|------|
| Ala | Gln | His | Asp | Tyr | Thr | Ala | Thr | Asp | Thr | Asp | Glu | Leu | Gln | Leu | Lys |      |
| 385 |     |     |     |     | 390 |     |     |     |     | 395 |     |     |     |     | 400 |      |

| GCT | GGT | GAT | GTG | GTG | CTG | GTG | ATC | CCC | TTC | CAG | AAC | CCT | GAA | GAG | CAG | 1307 |
|-----|-----|-----|-----|-----|-----|-----|-----|-----|-----|-----|-----|-----|-----|-----|-----|------|
| Ala | Gly | Asp | Val | Val | Leu | Val | Ile | Pro | Phe | Gln | Asn | Pro | Glu | Glu | Gln |      |
|     |     |     |     | 405 |     |     |     | 410 |     |     |     |     | 415 |     |     |      |

| GAT | GAA | GGC | TGG | CTC | ATG | GGC | GTG | AAG | GAG | AGC | GAC | TGG | AAC | CAG | CAC | 1355 |

```
Asp Glu Gly Trp Leu Met Gly Val Lys Glu Ser Asp Trp Asn Gln His
            420                 425                 430

AAG AAG CTG GAG AAG TGC CGT GGC GTC TTC CCC GAG AAC TTC ACT GAG     1403
Lys Lys Leu Glu Lys Cys Arg Gly Val Phe Pro Glu Asn Phe Thr Glu
            435                 440                 445

AGG GTC CCA TGACGGCGGG GCCCAGGCAG CCTCCGGGCG TGTGAAGAAC             1452
Arg Val Pro
        450

ACCTCCTCCC GAAAAATGTG TGGTTCTTTT TTTTGTTTTG TTTTCGTTTT TCATCTTTTG   1512

AAGAGCAAAG GGAAATCAAG AGGAGACCCC CAGGCAGAGG GGCGTTCTCC CAAAGTTTAG   1572

GTCGTTTTCC AAAGAGCCGC GTCCCGGCAA GTCCGGCGGA ATTCACCAGT GTTCCTGAAG   1632

CTGCTGTGTC CTCTAGTTGA GTTTCTGGCG CCCCTGCCTG TGCCCGCATG TGTGCCTGGC   1692

CGCAGGGCGG GGCTGGGGGC TGCCGAGCCA CCATACTTAA CTGAAGCTTC GGCCGCACCA   1752

CCCGGGGAAG GGTCCTCTTT TCCTGGCAGC TGCTGTGGGT GGGGCCCAGA CACCAGCCTA   1812

GCCTGCTCTG CCCCGCAGAC GGTCTGTGTG CTGTTTGAAA ATAAATCTTA GTGTTCAAAA   1872

CAAAATGAAA CAAAAAAAAA AATGATAAAA ACTCTCAAAA AAACAAGGAA TTC          1925

(2) INFORMATION FOR SEQ ID NO:4:

(i) SEQUENCE CHARACTERISTICS:
        (A) LENGTH: 451 amino acids
        (B) TYPE: amino acid
        (D) TOPOLOGY: linear (ii) MOLECULE TYPE: protein (xi) SEQUENCE DESCRIPTION: SEQ ID NO:4:

Met Leu Trp Asn Val Val Thr Ala Gly Lys Ile Ala Ser Asn Val Gln
 1               5                  10                  15

Lys Lys Leu Thr Arg Ala Gln Glu Lys Val Leu Gln Lys Leu Gly Lys
                20                  25                  30

Ala Asp Glu Thr Lys Asp Glu Gln Phe Glu Gln Cys Val Gln Asn Phe
            35                  40                  45

Asn Lys Gln Leu Thr Glu Gly Thr Arg Leu Gln Lys Asp Leu Arg Thr
        50                  55                  60

Tyr Leu Ala Ser Val Lys Ala Met His Glu Ala Ser Lys Lys Leu Asn
 65                  70                  75                  80

Glu Cys Leu Gln Glu Val Tyr Glu Pro Asp Trp Pro Gly Arg Asp Glu
                85                  90                  95

Ala Asn Lys Ile Ala Glu Asn Asn Asp Leu Leu Trp Met Asp Tyr His
            100                 105                 110

Gln Lys Leu Val Asp Gln Ala Leu Leu Thr Met Asp Thr Tyr Leu Gly
        115                 120                 125

Gln Phe Pro Asp Ile Lys Ser Arg Ile Ala Lys Arg Gly Arg Lys Leu
    130                 135                 140

Val Asp Tyr Asp Ser Ala Arg His His Tyr Glu Ser Leu Gln Thr Ala
145                 150                 155                 160

Lys Lys Lys Asp Glu Ala Lys Ile Ala Lys Ala Glu Glu Glu Leu Ile
                165                 170                 175

Lys Ala Gln Lys Val Phe Glu Glu Met Asn Val Asp Leu Gln Glu Glu
            180                 185                 190

Leu Pro Ser Leu Trp Asn Ser Arg Val Gly Phe Tyr Val Asn Thr Phe
        195                 200                 205

Gln Ser Ile Ala Gly Leu Glu Glu Asn Phe His Lys Glu Met Ser Lys
    210                 215                 220
```

Leu Asn Gln Asn Leu Asn Asp Val Leu Val Gly Leu Glu Lys Gln His
225                 230                 235                 240

Gly Ser Asn Thr Phe Thr Val Lys Ala Gln Pro Arg Lys Lys Ser Lys
            245                 250                 255

Leu Phe Ser Arg Leu Arg Arg Lys Lys Asn Ser Asp Asn Ala Pro Ala
                260                 265                 270

Lys Gly Asn Lys Ser Pro Ser Pro Pro Asp Gly Ser Pro Ala Ala Thr
            275                 280                 285

Pro Glu Ile Arg Val Asn His Glu Pro Glu Pro Ala Gly Gly Ala Thr
290                 295                 300

Pro Gly Ala Thr Leu Pro Lys Ser Pro Ser Gln Pro Ala Glu Ala Ser
305                 310                 315                 320

Glu Val Ala Gly Gly Thr Gln Pro Ala Ala Gly Ala Gln Glu Pro Gly
                325                 330                 335

Glu Thr Ala Ala Ser Glu Ala Ala Ser Ser Ser Leu Pro Ala Val Val
            340                 345                 350

Val Glu Thr Phe Pro Ala Thr Val Asn Gly Thr Val Glu Gly Gly Ser
            355                 360                 365

Gly Ala Gly Arg Leu Asp Leu Pro Pro Gly Phe Met Phe Lys Val Gln
370                 375                 380

Ala Gln His Asp Tyr Thr Ala Thr Asp Thr Asp Glu Leu Gln Leu Lys
385                 390                 395                 400

Ala Gly Asp Val Val Leu Val Ile Pro Phe Gln Asn Pro Glu Glu Gln
                405                 410                 415

Asp Glu Gly Trp Leu Met Gly Val Lys Glu Ser Asp Trp Asn Gln His
                420                 425                 430

Lys Lys Leu Glu Lys Cys Arg Gly Val Phe Pro Glu Asn Phe Thr Glu
            435                 440                 445

Arg Val Pro
450

(2) INFORMATION FOR SEQ ID NO:5:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:5:

Glu Asp Ile Trp Lys Lys Phe Glu Leu Leu Pro Thr Pro Pro Leu Ser
1               5                  10                  15

(2) INFORMATION FOR SEQ ID NO:6:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:6:

Phe Thr Arg His Pro Pro Val Leu Thr Pro Pro Asp Gln Glu Val Ile
1               5                  10                  15

(2) INFORMATION FOR SEQ ID NO:7:

```
    (i) SEQUENCE CHARACTERISTICS:
        (A) LENGTH: 2808 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: exon
        (B) LOCATION: 2051..2294
        (D) OTHER INFORMATION: /note= "exon 1"

(ix) FEATURE:
        (A) NAME/KEY: CDS
        (B) LOCATION: 2211..2213
        (D) OTHER INFORMATION: /note= "start site for translation
            initiation"

(xi) SEQUENCE DESCRIPTION: SEQ ID NO:7:

GCACATGGGA CGTCGACCTG AGGTAATTAT AACCCGGGCC CTATATATGG ATCCAACCAA      60

CTGTGGACTG AAAATATTTG GAAAAATACA ATAAAAAGTA AGACTACAAC AATAAAATAA     120

TATAAATAAA AAACAAGGCC GGGCACGGTG GCTCACACCT ATAATCCCAG CACTTTGGGA     180

GGCCAAGGCG GGAGGATCAC GAGGTCAGGA GATGGAGACC ATCTTGGCCA ACATGGTGAA     240

ACTCCGTCTC TACTAAAAAT ACAAAAATTA GCTGGGCATG GTGGCACGTG CCTGTAGTCC     300

CAGCTGCTCG GGGGGCTGAG GCAGGAGAAT CACTTGAACC CGGGAGGCAG GAAGTTGCAG     360

TGAGCCCAGA TTGTGCCACT GCACCCCAGA CTGGCGACAG AGTGAGACTC TGTCTAAAAA     420

TAAATAAATA AATAAATAAA AAATACAGCG TTAACAACTA TTTACATAGT ATTTAAATTG     480

TATTAGCTAT TACAAGAATC TAGAGATAAT TTAAAGTATT TTGGAAGATT TGTTTTACGC     540

TATATGCCGA TACTGTTTTC CATTCCTATT GAAGGACTTG AGCATCCCCT GGATTTTGGG     600

TATCCCCCGA TGTNCTGGAA CCATCCCCCC GGGGAAACC CAAGGGAACT NCTTGAATAN     660

TAGGCCCGGA AAAGNACAAA CAACCCCCNT GGGCCNTGGG GCACCNCTAA CCGGTGNTGA     720

AAAANCCCCA ATTACCCGAA AAAAAACCAG NAGGGCCTCC CAGGGAAAAA GGNANNGGCC     780

TGTGTGAACC CAGGTGAACT TTTCATTCNT GGGANTCGAT TTCTCCATTT GTACAAACTG     840

CTTGGTTTGT GGTCTGCAAG AGCCCTTCCT GTTCCTCCAG GAAGCTTCTC AGGGACNTCT     900

GTCCCTGGCC AGCTCTGCTC CTCTGACCGC TGCGGGTCCT GCAGGCCATA GCCCTGGCTC     960

CTGTGTGTGC ACCAGACACG TCTAGGCTCT TCAGCGGGAC CTATCTCTCT GCTCAACTCA    1020

ATCAACAGTT CTTTAGAAAT TTCCAGGGGC AGCAAAGTGC TGTAGCCCCT GACATGTTTT    1080

AGGGCTGAAT GGGGGTGGGT ATCAGCAGAC TCAATACGTA TTTATTAACT TAAAAGAAGT    1140

GTCATTGGTC TATTGGCAAA GCTGGTTAGC AATAACCTTA TCTTCTCCAG GAATAATGAT    1200

CACTAATCAT TCCTTCCTGC TGGGGGTAGG AGACAACCCG GCGTATGGTG GTGGAGCACC    1260

TGGGAGACAG AGGCAGAGAT CTCGTTCCTC GATCCCGGCG CGTTGGTTGT AAAGTAGGAA    1320

CAGTAATAGC ACCTACCTCT AGGGCCACGG AGACCGAATG AAATAATGCC TGTCAAGTCA    1380

CTTAGTACAC AGTAAGCACT CAGTAATGCT AGGTTGTTGT TATTATAATA AATTTTTAGC    1440

GAACGGGGAA GACCAAGCAC CGGTTGGTAC TGGGTTAGGC GCCGTAGGGC AAAGATGTGG    1500

AGATGTCCCG GAGGCGCCTA GGGTATCCGG GCGAAAACCC GAGGGCCGAA GGCTGGGAGG    1560

AGGCGGAGCG TCGGGCACCG GGCACCGGGC GGGAGGTGAG CCCCTGGAAA AGGAGGGGAC    1620

TCCGGGCGCG TTCTCCCAGC AGCCGCGGCT CCTCTGTTCA GGGCCGCGCC CCCTTCGCCG    1680

CACTTTTTCT TTGATTTCGA AAGCACTCCT CTCCTCCACC TAGTCTCCTT TCCTGGGTTG    1740
```

```
CAGGAGAGTT ACTGCTTTGC GGGGAAAGAA CAAGACGCCA GGCCGGCGGA TTAGTCCCCG    1800

CCCCGGGGCG GTGCAGCTGG AGCGTCAGGG GAGTCCCGCT CGCCGCAGCC CCAGCGCCGC    1860

GCGCGCCCAT CCATCCTAGA AGGACCTGGC GGTGCCGGCG CCCGGAGTGG CCCTTTAAAA    1920

GGCAGCTTAT TGTCCGGAGG GGGCGGGCGG GGGGCGCCGA CCGCGGCCTG AGGCCCGGCC    1980

CCTCCCCTCT CCCTCCCTCT GTCCCCGCGT CGCTCGCTGG CTAGCTCGCT GGCTCGCTCG    2040

CCCGTCCGGC GCACGCTCCG CCTCCGTCAG TTGGCTCCGC TGTCGGGTTG CGCGGCGTGG    2100

AGCGGCAGCC GGTCTGGACG CGCGGCCGGG GCTGGGGGCT GGGAGCGCGG CGCGCAAGAT    2160

CTCTCCCCGC GCGAGAGCGG CCCTTGCCAC CGGGCGAGGC CTGCGCCGCG ATGGCAGAGA    2220

TGGGCAGTAA AGGGGTGACG GCGGGAAAGA TCGCCAGCAA CGTGCAGAAG AAGCTCACCC    2280

GCGCGCAGGA GAAGGTGAGC GAGCCGGAGC CCCAGCAGCC GCGGAGTCCC AGCCGCCGCG    2340

GAGCCCCGGC CACCTGTCCC CCTATCCTCC GACCCCGGGG CCTGGTCCTT CGCCAGGATC    2400

TGGTGCTGTC ACCTCTAGAG GAGCGCTTTC GAGGGGCTTC GAGGTCCCCA GGCTGCGTTC    2460

CCCGGCGCTC TGGGTGCCCT CTTAGGTTTG CGTCCTCTGT CTCCCCACAC CCGGCCGGGG    2520

CAGGACAGGG CCCCGCTTTG CACCTTCGTG GCTCGGCTGC ACAGCAGTGG CCGGCCCTGC    2580

TCCAGGGCTC TTCTCAGGCG CGCGCTCCAA GCTACCCCCT TTGGAAGCCA AGGGCCNGGA    2640

AGCTTGGGAA GCCAGTTGGT GACCTCNACT CTCCCAGCCC CATGCANGCA ACCTANGCTN    2700

GGCCNGCCTC CGGGCGANCA NGGAATNTCT TCCTTNTTCC CCCTGNGGGA TTTTTTTNCC    2760

CCTTNCANTC NCCTTGGNTN CCTCTCTATT CTNGTTTCTT TTCTTCCN               2808
```

(2) INFORMATION FOR SEQ ID NO:8:

(i) SEQUENCE CHARACTERISTICS:
        (A) LENGTH: 704 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:8:

```
ACATAGTTCC CCAGGAACAN AACCCTTCTT CCAAGCCCAT NTNTCAAAAN GNGAGNTGTC      60

CNTGCAACCA GACACACAGG ACCCTTCTCC CGGGTGNTGT NAACACCTCC CCATCCCCAC    120

TCGGACAGTG GAGCCACCTA AGCCTGCTCC CCACCTCTGG GTGGAGAGTC TCGGTGGCCT    180

CCAACAATNT AGGNGCCANG CAGGAGGCCA CAGCAGCCCT GACGAGAGAG CAGAGGGAGG    240

AAAAGAGGTT TTAAGCCCAC CACTCACCTC CACATTTCAT GTGGCCCTCT CACCTCCTTA    300

TTTTCAAAGT ATAAACCTCA AGAAAGTGG AAAGGATACT ACAGGGACTA TCATTTACCC    360

TTCACCCAGA TTCACCAATC AACTGTTACC ACTTGGCCAC ANTCATTTGC TTTTTTCTTT    420

TTTTTTTTTT TCTTTTTTTT TGCTNTTCTC TTTTCTTGCT ATGTCGTCCA AGCTAGAATA    480

CATGGCGCAA TCATGGCTCA CAGTAGCCTA GACTTTCTGA GNTTAAACGA TCCGCCCACC    540

TCAGCGTCCC GAGTAGCTGG GANTACAGGC CACTGCACCT AGTTAGTATT TTTACTTTTT    600

GTAGAGACAG GGCCTCGCTA TGTTGCCCAG GTTTGTCTGG AACTCCTAGC CTCAAGTGAT    660

CGAGTCGACT CTAGAGGATC CCCGGTACCG AGCTCGAATC GCCT                    704
```

(2) INFORMATION FOR SEQ ID NO:9:

(i) SEQUENCE CHARACTERISTICS:
        (A) LENGTH: 551 base pairs
        (B) TYPE: nucleic acid
        (C) STRANDEDNESS: double (D) TOPOLOGY: unknown (ii) MOLECULE TYPE: DNA (genomic)

(ix) FEATURE:
        (A) NAME/KEY: exon
        (B) LOCATION: 132..209
        (D) OTHER INFORMATION: /note= "exon 2"

(xi) SEQUENCE DESCRIPTION: SEQ ID NO:9:

```
ACCATGGGCT GGGTGATGTT GGATAGAGAC TTCCCAGCCC ATGGTCTGTG NTGTTGGTGA      60

CTGAGCACTG ATTGGTTTGA CCACTNTCCT TTCCAAGGTA ACACTCTCCC CTTCTCTNTN     120

GGNTTCGGCA GGTTCTCCAG CAGCTGGGGA AGGCAGATGA GACCAAGGAT GAGCAGTTTG     180

AGCAGTGCGT CCAGAATTTC AACAAGCAGN TNGTGAGTGT GGGTGGCCCT TGGCCTTAGG     240

GAGTTTGTGA AAATTCGGCT GCCAGGTGAA AAATGGCACG AGCTGAATTT GTGGAGTACG     300

AGAGCTTGGA GGAGGGTAAT CAGTGTGGGC TGACAAGATC ATGTAAGACT TCCTNGAGGA     360

GGGAGCACTG GCAATGCATT GAAGGGANGG AAGAGGGATG GGGTATGTAT GCTTTAGGTT     420

CTTGGTAGGA GACATAGAAA CGGTAGTTGG GGGAGGGGGA GGGGGAGGGT GGGATAGGAG     480

CAGGCAATAG ATTGTGGCCA GACTTGGGGA AACTTTGCAT GTCAGGGGCA AGTGGAGCTA     540

TTAGANTTTG T                                                          551
```

(2) INFORMATION FOR SEQ ID NO:10:

(i) SEQUENCE CHARACTERISTICS:
        (A) LENGTH: 3226 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: exon
        (B) LOCATION: 677..734
        (D) OTHER INFORMATION: /note= "exon 3"

(ix) FEATURE:
        (A) NAME/KEY: exon
        (B) LOCATION: 851..945
        (D) OTHER INFORMATION: /note= "exon 4"

(ix) FEATURE:
        (A) NAME/KEY: exon
        (B) LOCATION: 1408..1503
        (D) OTHER INFORMATION: /note= "exon 5"

(ix) FEATURE:
        (A) NAME/KEY: exon
        (B) LOCATION: 2473..2579
        (D) OTHER INFORMATION: /note= "exon 6"

(xi) SEQUENCE DESCRIPTION: SEQ ID NO:10:

```
ATTTCCTGTT CAGGAGTTNA CAACCAGCCC CANTTTCCCT TCAGCCTTTT CCTTACATCC      60

TATGTCCCTG CTGTCAGCTG GGCCAGTGAT CTTGGCCATG ACCACCGCAT TCTGCACCCT     120

GCTGTAGTGC GTTTCTTCCG CAGTTCTTCT GTCCCTATAC AGGCTCGCAC CGGGCCNTCT     180

TTTCNTAGTA CGAGGCAGTG GGAGCTCTCT GTCCTTGGGC ACCACCTGAG CTTGTGGAGC     240

AGGGGGCCTG GTGGTCACCA CACCTGCCTT GCCCATACTC CTGTGCTCAT TGGTCACTTG     300

TCTGCAGGTG TCTGAGGGCA GGTCTGTGAG TGCCGGGGCT GCTGCACACT GGTGCTGTGC     360

TGTTTGTGTG TCATTCAGCC GTACCTCCAG CACGTCATCT CGGAGGGGGG TCTTTGTCTT     420

CCTGCCTTCC TTCCTGGGCT GAGAATGGCA TCTGGAAGAT GGCAGGTGCC CACAAGCATG     480
```

```
                                            -continued
GGCAAGGGTG CCTATGGACG CAGGGCTTCT GAGGCAGGGG TGGTGACCGT AGCTGCTGTC      540

CTGTTGGGAG GTCAGCTGAT CAGTGGCTGC TGTCAGGAGA GCAGCCTGGT TCATTCACGT      600

GAGGGTGGCA GGAAGGAGAG GGTCAGGGAC TGGGTGTGCC ACCAGTCCCT GACCTGGTCC      660

TTGTCCTTCT CTTTGCCTGA CGGAGGGCAC CCGGCTGCAG AAGGATCTCC GGACCTACCT      720

GGCCTCCGTC AAAGGTAGGG AGGCAGGCAG AAGCGCACCT GGCCCGTGTA GAGCTGGTGG      780

GTGCAGAGCT GGGGAGGGTG GGACAAGCGC TATCAGTGGG AGGCCCACAT ACTTCCTTTC      840

TGCCCCACAG CCATGCACGA GGCTTCCAAG AAGCTGAATG AGTGTCTGCA GGAGGTGTAT      900

GAGCCCGATT GGCCCGGCAG GGATGAGGCA AACAAGATCG CAGAGGTGAG CATGGGACAG      960

GTGGGCCTGC CCTTCTCAGA GGGCCCTCTG GTCTCAGCTC CTGTCCCACT CTGCCGTGCC     1020

CTCTGGGACA AGCCTCTCTG GTTCTCGGGC ATTCGCGTGC TGTGTGCCCT GGGGCAAGCT     1080

GCCCTCCCTC TCTGAGGGCC TTTCTCCTGA CACGCCCTCA CACCAAGGTG GGTCAGATGG     1140

TGGGTCGTGG TCGTCCTTAT TTGTGTGTTA TGGCTCACAA CTCACAAAGC CTCCCTGGCT     1200

GACCCCAGTC CTCAGCGTAT CTGATCCTCA CAGTCACCCC AATAGGGCAG GAACATTTGC     1260

CCCCATCTTA CAGATGGGGA AACTGAGGCT CTGAGAAGCC ACTGAGCTGT GAAGAGATGG     1320

GGCTGGGGCT GGTCCCTGCG AAGTGAGCGC TGGGGCGGGT GTGGCCCAGC CCTCCTGGTG     1380

GCACTGTCGT GCTCTTGCCT GTCTCAGAAC AACGACCTGC TGTGGATGGA TTACCACCAG     1440

AAGCTGGTGG ACCAGGCGCT GCTGACCATG GACACGTACC TGGGCCAGTT CCCCGACATC     1500

AAGGTGAGAG ACCCACTTGC AGATCTGCCC TGCTCTGGCC TGGAGGGAAC TGGAGAGAGG     1560

ACAGGGCCTA GGACCTTGCG GCTCAGGCCA AGAAGAAGCT GTCCTTGGAG GCAGGAAGCG     1620

CCTGGCCCGG TGTTTCACCC CTCCGGGGTT GCTCCCTCTG CCACCAGCCC ACGGCCCCCC     1680

ATTCCTTTCC TGTCCCTTTG GGTCTCAGGG CTATGGGAGG AAGCCTCACG GCACGTGTGT     1740

GTGTGTGTGT GTGTGTGTGT GTGTGTGTTG CNGCGGAGTG GCTGGCTATA TGATTGTGGA     1800

AGGTGTATAA GAGGGAGTAG GGCCAAAAAC ATGTGTGTGC CTGCAGGTCC CCTGTGTTTA     1860

CACCATGGGT GCTTGGAAGG GTATGTGTGC ATGTCACCTG TTGTCTGGGT CTACATGTGT     1920

GGGTGTGTGC GTGTGGTTGT GTGCATTCGC AAAGCCTGTT GTTTCTGCCA GGCCTGGGTT     1980

GGTGCTCGGA GCTGGCAGTG TCTCTGGTAT CCACCGAGGC GAGTGGTCCC CGGTAACGTG     2040

CACATGGAAG CCTGGGTTGA CCATTGGGTT GGACGAGATC CCCCTTGGTG GGCAGGATGG     2100

GGGTGTCATG CTCCATGCTA GCCTCAGGGG TCCCCAGTTG CAGATGCCTC AAGCTCCCTG     2160

AGTCTGATGT TGGTGGCTGT GGAGATGAGA AGCCAGGGGC CAGGCCAAGG AAAAGACTTG     2220

GCTGACACGT CACCAGCTGG TGGACACGGA CACATGGGCT CATGTGCAAG GAAGTGGTTT     2280

CACACAGTGG GGCTGGACGG CCAGGAGGGG GTGAGCTCTC TGCCACGAGG AGGGTTCCAG     2340

CAACAAGGGC TCAAGGGTTC CTGTGGAGCT GGGGTCTCCT GCCCGCCCTG CGGGTCCCTC     2400

CAGGATCCAC TGGACCTGGA GTCTCAGCAG GGGTGCCAGG CCCCGCTTAG TGCCCTCCTC     2460

TGTCTGCCCC AGTCACGCAT TGCCAAGCGG GGGCGCAAGC TGGTGGATAC GACAGTGCCC     2520

GGCACCACTA CGAGTCCCTT CAAACTGCCA AAAAGAAGGA TGAAGCCAAA ATTGCCAAGG     2580

TAAGGGCTGG AGGCGGGTCG GGGCAGCGTC TGCAGGGGGC TGAGAGAGGG CGGGTGTCTA     2640

GGACCCCGAG GGTGGAGGCT TCCTCCTGCC TGGCCCCAGG TGGCTGAACT GGGGGTGGGG     2700

ACNATACAGG GCCCAGGCCG GTGAGTGAGA GGCCCTTGTG GGTGCCTGGG TGAGGTCCAC     2760

CCTAGGCCCA TTCCTGCCCC CCGTGCCACC CTGGCCCCTC AGCCCTGATC CAGGCCACCT     2820

GCCAGCCTGA GAATGGGCCT CCTGGGTTTC CCTGGAACGG CGCCGCCCTG CCTGGCGAGC     2880
```

-continued

```
CGGGTGGAAT TCGTCACGCG ATCCCAGGCG ACCTGTCCCT GGCTGGAGCG AGCCAGTAGG      2940

TGCAGAGCTG GCCCCACTCA TCCTTTGGTG AGGGGCTGGG GTGGCCCCGT CCTCCGGGCA      3000

GGGCCGTGCT TGCTGGGCCC CCTGTGCTGC TAACCACGCT CACCTTTTGC CTCTGCAGTT      3060

GGAGTTCACC CCCTTTCCTT ACCCCCCGGG CTCCCCCTAA TTCTCTCGGC CTCAAGGGCC      3120

CATATCTGCT TGGGGTGGCC CCCCGCNCGT GGGGCGTTGT GGACCTGCAT TTAATCTGTG      3180

TGTCTCTGTT TCTCTCTCCC CACTCCCTGG TCTCTCCCAC CTTCCT                    3226

(2) INFORMATION FOR SEQ ID NO:11:

(i) SEQUENCE CHARACTERISTICS:
        (A) LENGTH: 8310 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: exon
        (B) LOCATION: 680..765
        (D) OTHER INFORMATION: /note= "exon 7"

(ix) FEATURE:
        (A) NAME/KEY: exon
        (B) LOCATION: 1052..1127
        (D) OTHER INFORMATION: /note= "exon 8"

(ix) FEATURE:
        (A) NAME/KEY: exon
        (B) LOCATION: 2503..2585
        (D) OTHER INFORMATION: /note= "exon 9"

(ix) FEATURE:
        (A) NAME/KEY: exon
        (B) LOCATION: 4059..4103
        (D) OTHER INFORMATION: /note= "exon 10"

(ix) FEATURE:
        (A) NAME/KEY: exon
        (B) LOCATION: 5543..5687
        (D) OTHER INFORMATION: /note= "exon 11"

(ix) FEATURE:
        (A) NAME/KEY: exon
        (B) LOCATION: 5688..5929
        (D) OTHER INFORMATION: /note= "putative.alt.exon"

(ix) FEATURE:
        (A) NAME/KEY: exon
        (B) LOCATION: 7094..7221
        (D) OTHER INFORMATION: /note= "exon 12"

(xi) SEQUENCE DESCRIPTION: SEQ ID NO:11:

CCAGNTGCNT GGNTGCNTCT CCCTGGCCCT GCACCTTCTT NTAGGGTCCC CCTGACATTC        60

CTAGAGGTGC CTGAGTGNCT GCNTCTGGTC TCCCTCTGGT GGGACAGGTC CCAGGAGAGG      120

GCTTTGTGGG AAGGACCATC CCTGGGAGGT GAAGTGAAGG CTGGTGGCTG AGGCTGCCAG      180

GAGCTGGCCC TCAGAAATGG GGAGGGAGCA CTCAGGGGCG GGGGCAATTG GGGGCAGCGA      240

CAGATGCTGC CCTGAGAGCC AGAAGGCAGT GGCAGGGCTG GCACCTAGCC TGAGGAGGTT      300

CATTGTGGAA GTGGGCAGGG TCCCCACTTG GCTGGGTCTG GGGTNTGCCT CTGTGCATGT      360

CCCGTGTCCA GCTCGCCAAG CCCCAGGCTT GCCCCTCTTG TTGTGCCCTA CTCCACGCTC      420

ACTGCCCTCC CGGCCACGTG GGCCTCTCTT TGGCAACGGC TGCTCAGCCC TCCCTTTCCC      480

AGATGTCCTC AGGGTCCTGG AGGGCTGCAG GGGGAGGTCG CCAGCATGGG TGTCCACATC      540

CAGTTCAGCC TCTGTCTTGC CCGGAGCCCT GGTCCCAGCG CACTGGCCAA GAGGGGTGGG      600
```

```
CAGGAGGTGG GAGGACTGGC CATGGGCTG  GGCTGGCTGG GACGCCCAAC AGAGGGGAAT      660

GACCCGTGCT GCCCCCCAGG CCGAGGAGGA GCTCATCAAA GCCCAGAAGG TGTTTGAGGA      720

GATGAATGTG GATCTGCAGG ATGAGCTGCC GTCCCTGTGG AACAGGTGAG GCCCGGCACG      780

GTGCCCAGCC TGCGTGGGGC AGTGTCCAGT CTGCGTGCTG CAGTGCCCAG TCTGCGTGCT      840

GTGGTGCCCA GCCTGCGTGC TGCGGTGTCC AGTCTGCGTG CTGCGGTGCC CAGCCTGTGT      900

GCTGCAGTGT CCAGCCTGAG TGCTGCGGTG CCTGGGCCCT CTCTGGTTTG TGCCTCTGAT      960

GAGCGTGTGT GGTCGCTCGT GGGTGGGTAT TTCTGAGTTG CTGTCCTGAC CTGCCTGTTC     1020

ACCTGGCCCC CATCCTTCCG CCCTTCTGTA GCCGCGTAGG TTTCTACGTC AACACGTTCC     1080

AGAGCATCGC GGGCCTGGAG GAAAACTTCC ACAAGGAGAT GAGCAAGGTA GGCCATGGGG     1140

ACCCCTCTGA GGGGCCACAC CCCACCCTGG CCGAGGGTCA GAGTCAGAAT CGTGGGAGGG     1200

GCAGCCTGAA CTCCTCCTTC CCTGCCAGGT TCAGCACACA CCGGTGACCA CAGGGCTCCC     1260

TCCCGGCCCT GGTGGAACAG CCCCCTTCAG GAGTGCCTGG GCCCCAGGAA GGGCACCAGG     1320

GCATGCTGGG GAGGCTTTGA GAGTGTCCTG GGTCCTTGCC TGGGTAGACC ACCTGAGAAT     1380

GTAGACCAGG CCCTCTCAAA CTGTGAATGT GTTCTCTAGC AACCTTGGCC CAGGGAGTGC     1440

AGTGTTAGAC AATGGTGGCA GTTTCTCAAT TTGTAGGAAA AAATTACTAG CATTTTCTCA     1500

ATTTTAATTT TTCTCCCATG CTTTTGAGAC ATTTAAATAG GCCTGTTTCG TCTGCGTGAA     1560

TCCACTGTGC GACAGGGTCT GGTCTGATTA GCGTACCTTT CTCTCTTGTG TTATTTTCAT     1620

TTTAACCTAT CTGGCAACTA AAACGCAAAG CTGTTGAACT TTGCAGTTGG AGAGACCCAG     1680

GGCTGGCACC CCCGCCCCCA GTGGTGGGTC TGACTTTGTC TCTTGGGCCC AGATGGATGA     1740

AGTGATGATG GTGGATTCCA GGCCCAGGGT CGGAGGAGGA AAAGCAGCTT GGGGCCTCCC     1800

CTGACTCACA CTTCTAAGTA CGGTTTCCTG CCTTTTAGAC TTTCTCTTTC CTTCTTAACT     1860

TTTCCTTTTT CCCTTCGAAG ATTGGAGACA ACTTACGAAA AGTTTAAAAA ATAGAGAAAG     1920

GTGTTTCAGA GAAGGAACAT TTATATAAAA TTAGTCTGTA AAAATATATG CCACAGAACA     1980

TAGTTGTTTA TAAATAGGAT GAAGATTCGG CCTGAGCTCC TATGGGCCAA TCCAAAAAAA     2040

GAATATTCNC CNTNATGAAA ATCCCCNTGT NTTANGAATA AACCCCCCCC CCTGCCTGTG     2100

CTTTCNNTGA AATATCTGGN ANTTGTTGTG TGGTCNGAAA ACNTCNTGGG NAAATGACCN     2160

TTACAATTNA NANTNATGGN CNGCCCAAAC NAATTTTAAN AAAAAAATNT TTAAACAGTG     2220

CCAGCTCNNT GTTGGATTTT AGGANATCCC CNTNAGTTNG AGGGGGAAAN ATNGGTTCCC     2280

AAAANAGCAG GGGTTTTTNA TNTTCCCCCC TTCCCCCTTT TGTGTTGCCC CCTGGTTTTT     2340

CCGGGTTTGG TGTTCTAATT CCCTGCCCTC TCACAGATGG GGAAAGAGGA GCTTGTTCCT     2400

GGCAGGGGCT GGGGGTGGTG GGGAGAAGCA GAGGTGTTTG GGGAAGGTGG GGCCGTTTGG     2460

TGGCCTTGGA GGCCCCCCAC CTCCTCACTG TCTCTCCTGC AGCTCAACCA GAACCTCAAT     2520

GATGTGCTGG TCGGCCTGGA GAAGCAACAC GGGAGCAACA CCTTCACGGT CAAGGCCCAG     2580

CCCAGGTGCG TGCGGGGAGA GCCCTGGCGC CCCTGACTGT GTGCACGGCA GGGGCAGGGC     2640

TCCTTCCTGT GACCCTGTTG GTGCCCTCCC CTGGTCCCCC ATGGGTTTGG CCTTGGGGGT     2700

CTAGGGACCT TCCTGTCTTG GCCTCTCTGT GCTCAGGGAG GCAGGTGAGG GCAGGTCTCT     2760

GTCTCGAATG TCCCTGCCCC TCTGGCTGTG TTCGTCGAGG AAGGAGCACT CTGGGGAGTC     2820

CGCGGGTACC CTGAGCCGGC TGACCCCCTC ATTGTGGAGC ACGAGCATCC AGGGTTGGGG     2880

TGGGCAGCCT GCTCAGCTTT GGGGACTGGG GGGTGTGAAC AGGACTGAAA GACTCCGGGG     2940

TGTGCAGTCC TCTCAGAGCA GGGAGATAGC ACCGCCCTTC CTCTCCTGCT NGTGGNAAAA     3000
```

```
GATCATGTCC CTGGATGGCA GCATTGTGCT CAACCACANG AGCATCCTCT TCCTGTCCTC    3060

AGCCTCAGCC CCTCCGGGAA TCCCAGCTGC AAGGAGGCCT CTGTTTCCTG AGGGGAAACC    3120

ATGAGGGAGG AGGGAAATGC CTTGCTTTCC TGGCTGTGGA TCAGAGGAAG CAGCGAGCCT    3180

GGGACTTCCC CTCCCTTNTG GCCATGTGTG CATGTGTGTG TGTGAGGGGG ACTGTGTGTG    3240

ACAGGTGTAA GTGTGTGCAT ACCCACACAC ATATCACAGC AGAACGCAGA GAACACCGAT    3300

GGACTCTGTA AAACAGGGCG ACTGTCTGCT TCTTGGGGTA TTGCCTGGGA TGATGAGGGT    3360

ATCGGGTGGT GGTGATTGCC CCCTCCTTCC CTGAACATAA AATAGTTGTG GCTGAGAGAG    3420

GGGCCATGGT GACCTGAGGC TGGGAGTGGG GAGGTTAGGA CGGTGGCGTT GTGGTGGTGG    3480

TTGGGGGGGT GGGTAGGGGG GTGGGGGTTG GGATAAAGCC AAAAGGTGAA TTCAAGGTCG    3540

GGCAGGGAGG GACAGCTGCC TGGCCTGTAG GCACAGGTGG GAACANTGGG ATGGATCAGC    3600

AGGGGGTAAG TGGGGCCGTC CTGGCCAGAA CCATGGCTCC CCTCAGGAAG GAGGTGGAGG    3660

GAAGAGAGAG GGGCAGTAGA GGCCCAGGAG TCTCCCTTCC AGCAGAGAGG CCTCTTGTGC    3720

ACTNTGTGCT CGCCTGGGGG CCTTTTCTGG CACTNTGGGC ACACCTGGAG CTCCTGGGGA    3780

CTGGGACCAC AGGCAGGGTG ACTATCCACT GCCCCGAGCC TCCTGCCCCT CACCAGGCCC    3840

TGTTAGCATC ACCTCGGGCA CCTGGCCACA GCAGGGGCCA GTCAGGGCAC CCCGGGATAG    3900

CACGCCCAGG CCCTGTGCAA GGCCTCTGGC ACTTAGGAGA GGCTTTTGCC CCTTTGTCCT    3960

CTGAGCAGAA GGGTTGGCAA AGAGGGAAGG GGACAGGCCA GTTCTGCACC TGGCCTTTCT    4020

CCAGAATGAA GGCCTCCACC TCCCGTCCGT CCCCACAGAA AGAAAAGTAA ACTGTTTTCG    4080

CGGCTGCGCA GAAAGAAGAA CAGGTACCGG CAGTGAGTGC TGCGGGAGGG GCGCAGAGGC    4140

CCGCGCCCTG GCTGGCCCTG TGCATGCGCC TTGCGCCCTG CTCCCAGGTG CCACTAACCC    4200

GTAATCTGGC TCTGTGTGCA GTGCTGCCCG GCAGGGCTGT CGTGTGCGTG TTGGGTGGGA    4260

AGGCGGAGGC GGCGCGGGGC GGGCTGGCCT CTGAGCATCT GGCTGCATTT AGCACGTTCC    4320

TCTGGGCGCC CCACACTTGT CTAGCCCTGG TGGTGCCCGG GCCACCAGCG CACTTAGCAA    4380

TGGAGGACGT GGCTGGGAAG GAGGCCTGGG GAGGGCCAGG GAGGTGACAC TGCAGCACTG    4440

TGGGGTTTTT TGTTTTTTAA ACAATTCTAT GTGTATACCA TATACTTATA CATATATTCT    4500

TTAAGGAGAA TACATTCCCA TAAAACACAA NTCCAGAAGG AAAGATGGTG TCAGCGACAT    4560

CTCTTACGNT GTTCCACTGT TTGCCCTCAG GTGANTCGGT CACTGGTTCC TGCTGGATGN    4620

TTGTAGATGT GCACTGTCCA GCACAGGAGC CAGTTACCCC ATGGGCTAT TGAGCACTTG    4680

AAACTGGCCA GTGTGACCGG GCAGCGGAAC TTTTCATTTG AATTACACAT AAATTTCATT    4740

GCTTTGAGTT TGCATTGCCG CCTGTGGCTA GTGGCAACCG TACTGGGCAG CACTTTTCTA    4800

GGCGTCTCTG TGCAGGTTCT GGTAGAGAAT TTTCTCCCTG CACCTTCGCC CCTGTGCCTG    4860

GGGTGCACAG CATCACACCA CCTCCGCCTT GGGTTCTGGC ACTGAACGCC ATGGCTCAGG    4920

ACCTGTCCCC TCCATCGCCA GCTGCCCACT CCTCTGTGAT GAGGACGCCT CTCTTAGTTT    4980

GTCCAGGCCC TGCTTGTGGC CTCCAGCAGC CGAGAGGACA GGAGAGCCCA AGGTCTAGAG    5040

ACATGTACCA GGGTGCTGTG ATGGACAGGC AGGGAGGGCA GCAGGCTGGG GAGCAGACCC    5100

CAGAACAGAG GGGCTGCTGC GTGTGGTGTG GGAGACTCAC TGTGCCTCTA GGATGTCTGG    5160

CTTTCTCCTG CTGTGGATCT TGGGCTGTCA GCATGGGCCC TGGTGGACCC CATGGAGCCT    5220

GTGGGTGGT TGGTCTGGTC TCTGCGACAG ATGGTTCCAA GGGACCTGCC TGCACTCCTG    5280

GGGACCATAG ACCTCCAGCC TGGAGTCCCA CCTTGTGCTG TTCCTGTTTC TGAGGCAGGC    5340

TTCCCACTTC CAGCCCCCCA AGCCCAGGTC CCTTGGCTCC CCCCACCCTC CTGCTCTCTC    5400
```

```
TCACATACAC ACACACACAC ACACACAGTT TCACACCTCC ATATGCACAC ACCTCTTCAC    5460

ACAGACGTCA ATACATTTGC CCCTCCGTCT CCTGTGCCTT GGCCCCCCAA CACTGGGCTC    5520

CCTTTCTTGT CCTCCCCCAC AGTGACAACG CGCCTGCAAA AGGGAACAAG AACCCTTCCG    5580

CCTCCAGATG GCTCCCCTGC CGCCACCCCC GAGATCAGAG TCAACCACGA CCAGAGCCGG    5640

CCGGCGGGGC CACGCCCGGG GCCACCCTCC CCAAGTCCCC ATCTCAGGTA GGGAGNGAAG    5700

TTTTGGTAGA AGGTCCCAAG CCNTCCATCN ATNTCGTCNG GGATNGGCTG TTGTCCTCCA    5760

TCCTCCCACT CCCTGTCCCC TTTCTGGCCT GGGCAGCTAT GGACCCGATG CTTTGCCCAG    5820

TGGGGGTTGG GCCTGGACCT GGGTGTCCTT TCCCCCATCC AGCTGGCATG CTTCCGGGAG    5880

GCATCTGTGA CTTGCTCGTT CCTCCCCAGC CCCCACCCCC ACTGCAGCGC CCTCCCCTTC    5940

CCTCTCCNTG GTGTTTTGTG ATGNTNGANT CTTTNTCCAT NTTNTTTTCC TCCCTAGCAG    6000

AGGGTATGGG CCCTCAGCCC ACAGAGCATC CAGATNTCCA GAGTGGGCTG CCTGTCCCTN    6060

TTNNTGGCCT CTCTCTTTTA AAGGGGCCTG AGGGAGGAGC CCAAGCCAGG TGGCCATGCA    6120

GGACCTTTAA AGGGACAGAG AGAGGAAGGG GTCAGAGGAG GGTGTGGGGT GGCTAAGGGG    6180

GCAGGTCNTG GGNTTGTGGA NTGTCCTTGT GTCCACCCCG CCTGCCCCCA GCGGGCCCTC    6240

CAGGTGTANG CAGGNCCCTA GGTGCTGGCT GGCCAGGNGG GGGAGTTTTC ATAGCCGGGA    6300

TCCTGCAGCT CCCGTTTTCT GCTGCCGCCC TGCTCTGCTG CTGACTAGGA TAGCAGGGCT    6360

AAGGACATGG TGGGAGCCTG TCCCAAACAG CACTTCCCCC GGCCTGGACA TGGTGCCAGT    6420

GCCTTCTGTG TATTCGTTCA CTGAGTCCCC ACAACACCCC TGTGAAGCAG GCGCTGTCAT    6480

CACCTGATGC ATGAGGAAGC CCANCGTCAT GGGTGTGTGA CCTGCCTGAG GTCCCCCACC    6540

TGGTGGGCAG GGGTGTGGCC TCTGCCCCAT CCTGGTGCCA CGCTGGCTTC CTCTGGGATA    6600

CACTCGTCTG AGCTGGGCTC CCTGTGGGCA GCCCTGTGCC CTGGGAGGTG GAAAGAGGGG    6660

CCTGCGGGAA NGGAGAGGTG GGCAGGGGGA GGCTGGGGCC CGGCTGTCTC TCAACGACTG    6720

TTTGCTTCCC CAGTCTTCTC ACCAGGCCAG TGGGAGCCAG CCCCTCCCAC AGTTGGCCAG    6780

TGGGCAGCCT GGGGCCTCTC TCTTCTTCGC TCTCCTTCCT CCTCTCCCCT CACTTCTCTA    6840

TCTCTTCTCT CTCCACACAG CGTTTCTGGA CCGCCTGCCT CAGTGTCCCT CTCGGGGGTG    6900

GCCTGGGGTC TNGGTGTCTA TGTTGGGGGG CTGGGAAGGC ANTNACTCTT CATTTGCTGC    6960

GTCCTGCTCA NTGGCCTGGG TGGGATGTGG CTGAGGTGTG ACTAACCGTG GCTTTGTCTC    7020

TGTCTGTCTC CCCCAAACCC CGTGCTCTGC TGTGCCTTCC CGCGCGGCCC CTCACCCGCC    7080

GCCGACCCAC AGCTCCGGAA AGGCCCACCA GTCCCTCCGC CTCCCAAACA CACCCCGTCC    7140

AAGGAAGTCA AGCAGGAGCA GATCCTCAGC CTGTTTGAGG ACACGTTTGT CCCTGAGATC    7200

AGCGTGACCA CCCCCTCCCA GGTCAGCCGC GGCCGCCGCG GCCCAGCTCT CCTCTCTTCC    7260

TGCCCTCTCA GGGCGTGCAT GGCCTTCATC CTCTATGCTT CTGTCTCAAG AGCCAGGAAT    7320

CTGGCCAGAG AGAGTGTCAG TTTCCCTCTC TCACCCTTTG TTCCCTCCAT CCATCATCCT    7380

CCATCATCCT CCATCACCCA TCTCTGAGCA TGTACTAAGG CCAGATGCAG GGCCGCAGAG    7440

GGGAAGGTGC CGCCTCTCCC GGCGCAGCAG TTACATCAGC AGCGCCCTCG CGATGCAGTG    7500

GGTGCTATGG CAGAGGGGAT CGGGGAGTGT GGAGGACTGT GGCTGTCAGG GAAGGCTTCC    7560

AGGGCCAGGG AGAGTTGGAA GGTCCTGGAA TGGCTGAAGC ACCTGGACTT CAGCTCCCAC    7620

AGCTGCTGTC AGCCCCTCGA GGGCGGGGGC AGCGGCCAGG CTGCAGGGCA NAACTGCCGG    7680

TGTGCAACAC TCCCTAAGAG GCGTGGAATG CCCAGATACA GCAGGGAGCC ACCCAGGGGG    7740

GCTTGGGTCT CTCCCGACGG GCCCTTGGCT CAGCAAGGAG CCACGCAGAG GGTCTTGGGT    7800
```

```
CTCTCCCAGT GGGCTCTTGG CTCAGCCGTG GAGGTGCCTC TGGGGAGCCC GGCCCACAGC    7860

CCCAGGTCTT ACGTCCTTCA TGGTGGAGGT CGGGCTGGAG TACCTGTGCT GGAAGCGCAT    7920

CTTGCCAGTG CTGGAGTGGG CTGACGTGTT GTCAGATTTG CCCAGAGGTG GCCGGCCTTC    7980

CCCGCACTCC CCGAGAGCTG ACTGCCTCCT CAAGGTCCAG CCCTCAAGGC CTCACCTTCC    8040

TCCTGTGGGT TAGCCAAGAA CCTTCCCACA CAAACCTCCC CTGTTAGGAA AGCTGTCCAT    8100

CCAAGCTTGT GGTGGCCTCC AACAAACAC CTTCCACACA CTCAAAAACC CTANTGGGGA     8160

NTAGTTTGGA AGGTTTTAAT TTTNGGGAAT TTGCCCNCTG GGAACTTGCA AACANTGGTC    8220

CCCTGCTAAG AAAGGTTTGG GANTGGTGGG CCTCCAACCC CCTNTGCNAA AANNTAGGAA    8280

ATTAAAACTN AGGAACCNAA GGCNNCCGCC                                    8310

(2) INFORMATION FOR SEQ ID NO:12:

(i) SEQUENCE CHARACTERISTICS:
        (A) LENGTH: 8078 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: exon
        (B) LOCATION: 1841..1948
        (D) OTHER INFORMATION: /note= "putative.alt.exon"

(ix) FEATURE:
        (A) NAME/KEY: exon
        (B) LOCATION: 2409..2432
        (D) OTHER INFORMATION: /note= "putative.alt.exon"

(ix) FEATURE:
        (A) NAME/KEY: exon
        (B) LOCATION: 3308..3601
        (D) OTHER INFORMATION: /note= "putative.alt.exon"

(ix) FEATURE:
        (A) NAME/KEY: exon
        (B) LOCATION: 4613..4702
        (D) OTHER INFORMATION: /note= "exon 13"

(ix) FEATURE:
        (A) NAME/KEY: exon
        (B) LOCATION: 4944..5054
        (D) OTHER INFORMATION: /note= "exon 14"

(ix) FEATURE:
        (A) NAME/KEY: exon
        (B) LOCATION: 5334..5435
        (D) OTHER INFORMATION: /note= "exon 15"

(ix) FEATURE:
        (A) NAME/KEY: exon
        (B) LOCATION: 7223..7783
        (D) OTHER INFORMATION: /note= "exon 16"

(xi) SEQUENCE DESCRIPTION: SEQ ID NO:12:

CTTGCNTTTG TCCATGAAAN NNNNNGCCCA CGGGCTTACC CGGNTGTGGG GTGGTGNGTA     60

GCGTGTGTCC NTGACATGGA GGGACNGTCC CGGGCCTGCA TGGCGGGGTG CCACCTGCCG    120

GGGCAGCACA GCGAAGGGAT GGTCAGCTTT TTGGCGGATG ACCCTCCCCT CAGCACATGA    180

CGGATATTGC TGCGTGGGTT GGCTGACTTT TATGAGACAG GAGGGAGGGG TGTTGCTGGG    240

GCAGGGTGGG GGCCACTGGG GAGAGATGCT GGCCGCCCGC TGGTGGGAGG CACCTCGAGG    300

CTGTGCACCG GCGTCCTCAG GGCTCCTTCA GAGACGGCCG GTTATGGGGC AGAGCAGTGA    360

CCTCCCGACC CTGGGTTCCC CAGACAGGGC TGGACCTAAA GGAAAGTCAG CTGCTGGGAT    420
```

```
TGGCCCAGGG CAGGGCTTGG GGCCTAGGGC CCCTGGTTCT AGGAAGTGAG TCCACTTGGC      480

CTGAGCTGTC TGACACCTTG GCTTGGCCAT GTGGANTGCT CCACGCTTGT CCCCTGAGTG      540

CAGGACAGCT GGTCTTCTTA GGACTGAGGA CCTTGGTNTC TCCCAATGGG CCTTCGGTTC      600

AGNTATGGAG TGCTTNTGGG GAGCCCGGCC CACAGCCCCA GGTCTCACAT CCTTCATGGT      660

GGAGGCCGGG TGGGAGGGCG CCCCTGTCAG TGTCCGGTGC CTGTCAAGAG TGTGTAGAGC      720

CGGGAAGCCG CTGGCCTGGG CTGCGGGGCT GGAGTTCTTC CAGCACTGCC TGAGGGCCCC      780

GGAGGGGAGC ACCCCGGCCA CGTCCCTCTC CTTTTAAACC TGGGCAAAGT TCTCTCTGGC      840

CCCCAAAGGG AAGCCCCAGG TACAAGATGG AGACCGCAGC CGAGCCAGTC CCTGCTCCTC      900

AGAAGGCAGC TTGTGCCCTG GCATGGATG CTGCCCCAGG GCTCACCGGA GTCATTGTCC       960

CCGCCTGTGC CGGGGGCTCT AAGGAAGCCC CTTCCTCCCA TGCTAGTCTG GCCCAGCTTA     1020

TGGGGAGGCT TGTCCCTGTG TGGCCAGGGC CACCGTGTCC CATCCCTGGG GCCATGCCTG     1080

TCACATGCCT ATTCCTGGGC TCACTGGAAG GAGATCTTGG CGAGGGGCTG CTGGGAGGGG     1140

TCAGGGGCCT GCAGTTTTAA CCCAAGTGCC CCGGGTGGTT CTGAAGCCCC CGAATGTTGA     1200

AGACCCCACT TTGAAGCTTG GCTGTTGGGC TTTGTGGCTG GCTCCACTCT TTCTCCGTCC     1260

CTGGAGCTGA CGGCTGGTGG TGTCGCCAGA GAGTGACCTG CCTGTCTGGG GTGGAGGAAA     1320

AGCCAGTGTG AAGTCTCTGC CTTTGGAACT TTCCCAGTCG GGAGCACTGA GGGTGGCTGT     1380

GGCATGGTGT TACTCTCGCC ACTGGGGGGT AGCAAGATCA GCAGAACTCT TGGCGCAGGG     1440

AGCGGAGAGG AGGTTCGGGC ATTGGTAGGG AGGGGCCCAC CAGTCTGTGG ATGGTGGCGG     1500

AAGAGAGCTG GGGCCTGGTG CTGGCCCTGC GGGGTGGCGG CCACGGGCGG ACCTATGACT     1560

GGGAGTTTGA GGCGGGCACT GGGGTCGTCC TCCTGGTGTG GGCGGGAGCC TGTGCCGGGG     1620

CGCGTGGCTT TGGGCAGTGC TCCCGTGTGT GAGGTGGATG AGTTGGTGCC TGGGCTGTGT     1680

GCCAGCGTGT GTGCGTGTAT GTGCGCTTGC TCTGTGCATG CGTGGTGTGT GTATGTGTGT     1740

GTGTCCACGC GTGTGCCTGT GCCTGCAGTG TCTGCCTGGG GTGAGGGCTC CCAGCTTAAC     1800

ACTAACTGCT TCCTCCTCTG CTGCTGCTGC TGCTGCCAAG TTTGAGGCCC CGGGGCTTAT     1860

CTCGGAGCAG GCCAGTCTGC TGGACCTGGA CTTTGACCCC CTCCCGCCCG TGACGAGCCC     1920

TGTGAAGGCA CCCACGCCCT CTGGTCAGGT TGGTTGTGCC CACCACTGCC CATGGGCCCA     1980

CCAGCTTCCA GGTGCCCAAC CCTGGGCTCA TGTTGCCTAT TGGCCACGTG ACCCCAGCTA     2040

GGCCTGGGTC ACTGCCCTTC CCCTGGCACC TCAGCCTTCA GCCCTCATCA CCTCCTGGTT     2100

GTAGGGCAGG AAGCAGCCCC TGATCAGCTG GGAGAACTCT CAGTAGGGGG TTACTGAACA     2160

CTTCCTGGCA ACTTTGTGCT CATCGCTTGG GGCAGAAGCA TCCTGGCTTG GGTCTTGAA      2220

GCTCCCTGAG AGGTGTCGGG AGCTCGGCCA CCTGCAAATC TTGGAGTCTA CCTGGCTCCG     2280

AGCCACTCCT GTGCCTGCTG GGCTGGATGG CCTGGGGCGA GCGGGGGTAG GGTCCCCTGG     2340

GGACTGCTTG CCGCCCTGTC TCTAACCTCT GTGCTAACTG TCCTTCTCGC CCTCACTGCT     2400

GCGCTCAGTC AATTCCATGG GACCTCTGGG AGGTTAAGCT GCACTCTGCT CTTTGTCCAC     2460

CCCCTGGGGG AACCACTCTT TCCCGTATGT GTCCAGGCCC ACATGATCAT AGCCTGTTCA     2520

CAGGTGCATG CACCCCACAC ACCCCCCACA AGCAGGACAC ACAGGCACGT GCTCACGCAC     2580

AGGGAGNTGG TGAAGCCACC CGCCTCCAGC CATTNTGNTG CTTCTCCCTC TGGCAGGCCC     2640

TTGGAAAAGG GGATCTTCGG TTTAGCTTGA GACAGGGGTC CCCTGAGATC TGGTCCTGTT     2700

TTCACAGCCT GTGAGTGTTT GCCTCCAGAC AGAAATGGGC CGGTCACCCA GGATGGACGA    2760

GTGTCCTCAG GGTGTGGGGC AGGAGGGCCT CAGGGTAGAA GGTTCTTGCC TTCTCTGAGC     2820
```

```
TTTTTGGCAG TGGGGAGCTG TTTGCGAGGA AGGGGAGAGG GGAGGAATGG ATGGTTTGAG      2880

AGAATCAGGG AAGACAGGGT GTGGCTGAGT GCCTTCTGAG AGCAGGGCCT GCAGGCAGGT      2940

GCGAGGCCAT CTCACACAGC ACCATGTCAC TGTCACCTGA TAGCTCAGGA CACAGAGGCT      3000

CAGGGAAGGC TCAGTACTTG CCCAAGAACT GGTCATGGTA GAGCCAGAAT TCCAACAGGG      3060

TCTCCTGGGC TCTGTCCCTG AGACCCCCTG ATACAGGCAG AGATGCTGGG AGGGGCAGGC      3120

GGGTGTGCAG GCGCCCTTGG GGCATGCGCT GGCAGCCCAG GCTCCTGGGA GCTCTGGAGG      3180

CTCCACCGCA GGATTTCCCT CTGGAGGAAG CCAGAAAGAG CCAGCCTGGT GCGAGCTGGT      3240

AGGGCCATTT TGACAAGTGG ATTTCGGTAG GTGCTGAGCT TGGGCAGCAC AGTCACACCT      3300

GCCTGTCCCT TTGACAGTGG TAGGAGAGAG GATGTGGGAG GCGGGTGGCT GGCCGGGCTC      3360

CGCTGGTACC CACCCTGCCC CCACCAACCC CAGCCGCTGG TGACATTTTC TCTTGTCTTG      3420

TGATCCTGCC CATTGCCTTT CCACCCCGGC CTCCCCGCCC CCTCCCTGTT CTCTCCTCGT      3480

GGCCTGTTAC CAGCCCACAG AGAGTCCAGC CGGCAGCCTG CCTTCGGGG AGCCCAGCGC       3540

TGCCGAGGGC ACCTTTGCTG TGTCCTGGCC CAGCCAGACG GCCGAGCCGG GGCCTGCCCA      3600

AGTAAGTGCC CACCTCCAGC CCCTGTCTGG CTTGTCCCCA GTCTCTAGGG GTGCAGCATG      3660

GAAGGAGAGC CCCGAGGAGG GGTTGCAGGA GGGACCAGGC CACCATGGAT GTGAGGGTGA      3720

GGACAGGGTC CTGAGCTAGG CTGCCCCAGC ACGGGCTTGT CACCAAGGCT GCCAAGGATG      3780

AATGAGCGCA CTGGGCGCAT CAGCCCCTCC TGCTTGCCCA CCCCAGCCCA GCCTCCCACG      3840

CAGGAAGACA TTTAGGACAC CTACTGGTTT ATGCCAGGCA CTTTCCAGAA TCTTCTCATT      3900

TAATCTTCGT CATCACCTTT ACAGCCAGAC ACTTCCTCCT TTTACAGATG AGGAGATGGG      3960

GGCTAGGAGG GTTGAGTAAC TTGGTTCCAG CACTCAGAAG TGGCCAAGTC TGAGTGTCGG      4020

CCCAGGTCAG CCCAGCTCTG GGGTTCCTGC AGGGCCTGCC GTGGTGCCCG TGCTGCGGTG      4080

CCCGTGCTGC GGTGCCCATT TCTGTGCCAC ACCCTTTCTT GGATTTGGGC TGCGCACAGG      4140

CTTGCACCGC ACCACCTGCG GTGGGTTGTT GTTCAGGCTG GGANAGANGT GTGTTGNTGT      4200

CCCCTGCCAT GGAATATTTA TAGGTGCAGC AAGATCCTGC CACCTGCCGG GTTAAGCAGG      4260

GTGGGCGGGC GGTGGCTGTG GTGGGCGAGG TCTTGGTGCC GAGAGAGCAG GGCCTGTGAG      4320

GCGGGGTTGG GGGTGGCACT ATGGGGCTTG CACTGGGTTC TTCACAGCAT TGTCACTCAC      4380

ATCCTTGGGC NTGCCAGCGC NTACTATTCA GCTGCTTCCC CGGCCCAGGG CCCAGCTTGT      4440

CCAGCAGAGG CTCCCNTGGA TTNTTCGAGG CACTGGGCAG CTCTAGACCN TGCTGCCAGC      4500

CAGGCGATGC CCCCGGCCCT GTTGCTTGGG TGCTGCCCTC CTGTGGCCTG TTTCCTGTGT      4560

CCTGGCTGTG TCCTGTCCTG TGTCTGACCC CAAGCCGGCA TTTATGTTGC AGCCAGCAGA      4620

GGCCTCGGAG GTGGCGGGTG GGACCCAACC TGCGGCTGGA GCCCAGGAGC CAGGGGAGAC      4680

GGCGGCAAGT GAAGCAGCCT CCGTAAGACA GCAGGGACAA AGCCCTGCCT TTTCCTCCCT      4740

GCCGCCCGCC TGCCTGTCCG GGGCTCCCCT GTGGCCCCTG ATGGTGCTGG TCCAGGCCTG      4800

GCTCCTGTTG AGGAAGCTGG AGGCGGGCCG GTCTGGCACC AGGCGCAGAC ACCTTTCTCC      4860

CCTCCCCGCC CCTCTTCTCC TCGGTGGCCC TGGCTGTCCT TGGACCACCT TCCCTGCTCA      4920

GCTGACCCGT ACCTCTGCCA CCAAGCTCTC TTCCTGCTGT CGTGGTGGAG ACCTTCCCAG      4980

CAACTGTGAA TGGCACCGTG GAGGGCGGCT GTGGGGCCGG GCGCTTGGAC CTGCCCCAG       5040

GTTTCATGTT CAAGGTGAGC CCACAGCCTC TGACTGCTGC AGTCCCTCGG TGCCCTGGTG      5100

GGCAGATGAC AACCCTGAGC CTCAGGAGAC TCTGTGGTTT GCCCAAAGTT GTGCAGGCGC      5160

TACTAGGTCA CTCCCAGCCA GCAAGGTGGC ATCTGANCCC CATACAGTCC TGCTGCTTTT      5220
```

```
GAGCACTCCT GGTCTCCATA CTGCCACCTG CACCTCCCAC ACGCAAGGCC CGTGCTCTGT    5280

GCAGGGCTGG AGGTGGGACG GAAGGTCTGA CTTGCGATCC GCATCCTCTG CAGGTACAGG    5340

CCCACCACGA CTACACGGCC ACTGACACAG ACGAGCTGCA GCTCAAGGCT GGTGATGTGG    5400

TGCTGGTGAT CCCCTTCCAC AACCCTGAAG AGCAGGTGAG GGCTGGGTGG GGCCCCACA    5460

CCNCANGGGG ACCACCNNGC ATCCTGGCTG CGGCTGGCAC CNCCGTNGCG GATACNCGCC    5520

ATTCAGGGGG CAGCAGAGGC CCGCGAGCAC CAGGGCTCCC GCGCCAACTG CTCCTCCCCG    5580

CCCTCCACGT CGGGCTTTTT CCTCTCTCCC TCTCCTCTCC CTTCCCTTGG CCCCTCTCCT    5640

GTTAGGCCTC TCTCTCTCCC TGTCCCCATA CCCGCTTCTT CCTGTAGCCT CTGCTTTCTT    5700

CTCCCCACGT CCCCCCTTTG CTCAGGCGCT CTCAGCTCTG CCTCTGTCTC TCCCCTTCTC    5760

CTCTCCTGGC AGCTGTGCCT GAGGCCTGCC TCCCTCCTGG GACAGGATGC TTGACCCCTC    5820

CTGCCCCGCC CACAAGGTGC CCACCCTGCA GCCAGCCGGA GCACTGGTTG GGCTCATGAA    5880

GCCCCGTGTG CCGTCCCTCG AGGCGGGCCC TGCCCTGTGC ACNCAGGGCC ATGGGCTTCC    5940

CAGCTGTGTC CCCGGCTGAG GCTCACCCAC GATGCCTTCC AGACCCTTCT CCTCCTGCTG    6000

TGGCTTCATG TTAATCTCCT GGAAGTGAGG GCTCCTGTTG AGCCTGGGTG GGTGCTAAGT    6060

GTGTCCCTCC TAAGTCTTGG GACCTCCTGG ATCTGGGTCA GTTTGCCCCT CCCCAGGGGG    6120

CCTTGGAATN ATNGGCAAGG AGCTTCCCCG NTGTGTAGAA CCNAGCTTTG NTTGTGGGGG    6180

GTCGGTGGTG CCATGTGGGC ATCTGGTTCT TCCACGGTTC AGCCCCTGAG CACNTCGGGC    6240

TGTGCACAGA GGGCCTGGCC GGTTATTCCT GCTTCCAGAG AACATGTTTA GCCATCAACG    6300

CTTCTGTGTG AATAGGTTAT CAGAGCGGCT GAGGGTGACA GTGGGTCTGC CTGGGTCTTG    6360

GATGAGGCCG ACCNTACTGG GGGTCCTGGG CTGGGATGTA GGGGTACCAA GTACTTACTG    6420

AGGTCCGGGG CAGGAGGCCT GAGTGATGAG GACCTTGTGG GCCTGGCACT GATTTGGCCC    6480

TTTCTCNTAA GCCCCCAGGT CTTCATGGAC CTCCTAGTGG GCCAGCCCTG GCTGGGTAGG    6540

ATTTCAAGCA GACTGCTACC CAGAGCCCAC AGTGAGAATT GGCCTGGGGN TGCTGGAGGG    6600

GGCTCAGGGC ATGAGTAGGG TCTGTGACCA GGCTGACAAT GACACAGAGG GAAATAACAA    6660

AGACCCAGGT AGGCCCCAGG CACAGCCCAG CTGCAGGGGC AGCCTCGGCC CAGCCACTGG    6720

CAGGAGTGGA TGGCCATACG GCTCCCCGTG ACCCACCTGG GGCCAGGGGC CTGTCAGCAC    6780

TCCCAGAGAA GGCCCTGCGG GTGTCAGGAT TGAAGCAAAG GGCAAGTGGA AGTTGGAGGG    6840

ACTGGTGGGA TGGCCCCAAT CCCTCTAGAA TTGTAACTTG TTGTCACTCC CAAAACTTCG    6900

TGGGGTTGTT TGANAAGCCT GNAATCCTGG AAGGGCTGAT GTGCACATCA TGCATGCAGT    6960

GGGACTCATC AAAACCAGCC ACGAATGGTT AGATCCACCT GCGGACTCAC AGGCTGGCTC    7020

CTGTGGTGCC TCTGGGCAGG AGCCTCAGCC AGCANCATCA GGGAGTGCTG CCTGGAGGAG    7080

GTGTTCTCAA GGTGGGCTTG GCAGGCTGAG GCACCAACAG CAGGAGGAGG GGCCGTCTTC    7140

CCAGCAGGTT GGAGTGGGAT GCGTGCCCTG TGGGGTGGAN CCCCTTGCTC ATCCCTGTGC    7200

GACCTGNTGC TCTGCCCCTC AGGATGAAGG CTGGCTCATG GGCGTGAAGG AGAGCGACTG    7260

GAACCAGCAC AAGAAGCTGG AGAAGTGCCG TGGCGTCTTC CCCGAGAACT TCACTGAGAG    7320

GGTCCCATGA CGGCGGGGCC CAGGCAGCCT CCGGGCGTGT GAAGAACACC TCCTCCCGAA    7380

AAATGTGTGG TTCTTTTTTT TGTTTTGTTT TCGTTTTTCA TCTTTTGAAG AGCAAAGGGA    7440

AATCAAGAGG AGACCCCCAG GCAGAGGGGC GTTCTCCCAA AGTTTAGGTC GTTTTCCAAA    7500

GAGCCGCGTC CCGGCAAGTC CGGCGGAATT CACCAGTGTT CCTGAAGCTG CTGTGTCCTC    7560

TAGTTGAGTT TCTGGCGCCC CTGCCTGTGC CCGCATGTGT GCCTGGCCGC AGGGCGGGGC    7620
```

-continued

```
TGGGGGCTGC CGAGCCACCA TACTTAACTG AAGCTTCGGC CGCACCACCC GGGGAAGGGT    7680

CCTCTTTTCC TGGCAGCTGC TGTGGGTGGG GCCCAGACAC CAGCCTAGCC TGCTCTGCCC    7740

CGCAGACGGT CTGTGTGCTG TTTGAAAATA AATCTTAGTG TTCAAAACAA AATGAAACAA    7800

AAAAAAAATG ATAAAAACTC TCAGAAAACG TGTGTGTATT TGTTCTCCCT CTTCTTGTCC    7860

GTGAGTGCGG ATGGAACCGT GTNATCTGTG GCTTTCTTAC TGAGATGGTC TGCCCCCGAA    7920

GGCCCGCTGC CCTGNCGCTG GTGCACCACA GGGCTTCACC CCCTGTCCCC TGGGGTTCTT    7980

AGGGGTGGTC ACCTGGANGT CANGGACTGG GGGCTTGGGT TAAGGGGCTT GGCCACCCAT    8040

CTCTTGTCCC ANAAATCTTG CTNACTGCCC CCCTAACT                            8078
```

(2) INFORMATION FOR SEQ ID NO:13:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

```
Met Ala Glu Met Gly Ser Lys Gly
1               5
```

(2) INFORMATION FOR SEQ ID NO:14:

(i) SEQUENCE CHARACTERISTICS:
        (A) LENGTH: 31 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "oligonucleotide probe"

(xi) SEQUENCE DESCRIPTION: SEQ ID NO:14:

```
GGAGAATTCG TTGTCACTGT TCTTCTTTCT G                                     31
```